(12) United States Patent
Lepilleur et al.

(10) Patent No.: US 8,450,294 B2
(45) Date of Patent: May 28, 2013

(54) SHAMPOO COMPOSITIONS

(75) Inventors: Carole A. Lepilleur, Akron, OH (US); Jeffrey A. Fruscella, Mentor, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 820 days.

(21) Appl. No.: 12/350,590

(22) Filed: Jan. 8, 2009

(65) Prior Publication Data

US 2009/0137438 A1   May 28, 2009

Related U.S. Application Data

(63) Continuation-in-part of application No. 11/014,424, filed on Dec. 16, 2004, now abandoned.

(51) Int. Cl.
- *A61K 31/715* (2006.01)
- *A61K 31/695* (2006.01)
- *A61K 8/18* (2006.01)
- *A61Q 5/00* (2006.01)
- *C08B 37/00* (2006.01)
- *C12P 19/04* (2006.01)

(52) U.S. Cl.
USPC .............. 514/54; 514/63; 424/70.1; 536/114; 536/123

(58) Field of Classification Search
USPC .............. 514/54, 63; 536/114, 123; 424/70.1
See application file for complete search history.

(56) References Cited

U.S. PATENT DOCUMENTS

| | | |
|---|---|---|
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,798,053 A | 7/1957 | Brown |
| 2,826,551 A | 3/1958 | Geen |
| 2,891,050 A | 6/1959 | Elverum et al. |
| 3,208,823 A | 9/1965 | Baker et al. |
| 3,332,880 A | 7/1967 | Kessler et al. |
| 3,711,604 A | 1/1973 | Colodney et al. |
| 3,840,657 A | 10/1974 | Norfleet |
| 3,925,456 A | 12/1975 | Ploger et al. |
| 3,929,678 A | 12/1975 | Laughlin et al. |
| 3,932,606 A | 1/1976 | Barth et al. |
| 3,934,002 A | 1/1976 | Haefele |
| 3,937,807 A | 2/1976 | Haefele |
| 3,939,261 A | 2/1976 | Barth |
| 3,941,772 A | 3/1976 | Ploger et al. |
| 3,959,458 A | 5/1976 | Agricola et al. |
| 3,960,888 A | 6/1976 | Ploger et al. |
| 3,964,500 A | 6/1976 | Drakoff |
| 3,988,443 A | 10/1976 | Ploger et al. |
| 4,025,616 A | 5/1977 | Haefele |
| 4,034,086 A | 7/1977 | Ploger et al. |
| 4,042,679 A | 8/1977 | Gaffar |
| 4,064,164 A | 12/1977 | Blum et al. |
| 4,098,880 A | 7/1978 | Gaffar |
| 4,100,270 A | 7/1978 | Gaffar |
| 4,108,961 A | 8/1978 | Ploger et al. |
| 4,108,962 A | 8/1978 | Ploger et al. |
| 4,123,512 A | 10/1978 | Gaffar |
| 4,137,303 A | 1/1979 | Gaffar et al. |
| 4,143,128 A | 3/1979 | Kim et al. |
| 4,144,324 A | 3/1979 | Crutchfield et al. |
| 4,152,416 A | 5/1979 | Spitzer et al. |
| 4,177,258 A | 12/1979 | Gaffar et al. |
| 4,183,915 A | 1/1980 | Gaffar et al. |
| 4,215,105 A | 7/1980 | Gaffar et al. |
| 4,224,308 A | 9/1980 | Gaffar et al. |
| 4,224,309 A | 9/1980 | Gaffar et al. |
| 4,348,381 A | 9/1982 | Gaffar et al. |
| 4,364,837 A | 12/1982 | Pader |
| 4,386,213 A | 5/1983 | Giesecke et al. |
| 4,427,707 A | 1/1984 | Heine et al. |
| 4,645,833 A | 2/1987 | Bayerlein et al. |
| 4,661,475 A | 4/1987 | Bayerlein et al. |
| 4,686,254 A | 8/1987 | Lochhead et al. |
| 4,704,272 A | 11/1987 | Oh et al. |
| 4,741,855 A | 5/1988 | Grote et al. |
| 4,753,659 A | 6/1988 | Bayerlein et al. |
| 4,788,006 A | 11/1988 | Bolich, Jr. et al. |
| 4,826,700 A | 5/1989 | Bayerlein et al. |
| 4,840,811 A | 6/1989 | Bayerlein et al. |
| 5,047,177 A | 9/1991 | Varco |
| 5,104,646 A | 4/1992 | Bolich, Jr. et al. |
| 5,106,609 A | 4/1992 | Bolich, Jr. et al. |
| 5,153,294 A | 10/1992 | O'Lenick, Jr. |
| 5,275,761 A | 1/1994 | Bergmann |
| 5,296,625 A | 3/1994 | O'Lenick, Jr. et al. |
| RE34,584 E | 4/1994 | Grote et al. |
| 5,656,257 A | 8/1997 | Fealy et al. |
| 5,733,854 A | 3/1998 | Chowdhary et al. |
| 5,801,116 A | 9/1998 | Cottrell et al. |

(Continued)

FOREIGN PATENT DOCUMENTS

| | | |
|---|---|---|
| DE | 3114783 | 10/1982 |
| DE | 3335593 | 4/1985 |
| DE | 3347469 | 7/1985 |
| DE | 10047278 | 4/2002 |
| EP | 0582152 | 2/1994 |
| GB | 849433 | 9/1960 |
| WO | 9323009 | 11/1993 |

OTHER PUBLICATIONS

Meuller, S.O. et al., Occurrence of Emodin, Chrysophanol and Physcion in Vegetables, Herbs and Liquors. Genotoxicity and Antigenotoxicity of the Anthraquinones and of the Whole Plants, Food and Chemical Toxicology, vol. 37, 1999, pp. 481-491.

Kapoor, Virendra P. et al., *Cassia spectabilis* DC Seed Galactomannan: Structural, Crystallographical and Rheological Studies, Carbohydrate Research, vol. 306, 1998, pp. 231-241.

Ward, Florian M., GuarNT Bland, a Reduced Odor Stabilizer and Soluble Dietary Fiber, Macromol. Symp., vol. 140, 1999, pp. 97-105.

*Primary Examiner* — Patrick Lewis
*Assistant Examiner* — Everett White
(74) *Attorney, Agent, or Firm* — Thoburn T. Dunlap

(57) ABSTRACT

The present invention relates to a shampoo composition comprising a minced polygalactomannan hydrocolloid(s) in combination with a water soluble silicone compound.

25 Claims, 5 Drawing Sheets

U.S. PATENT DOCUMENTS

| | | |
|---|---|---|
| 6,410,005 B1 | 6/2002 | Galleguillos et al. |
| 7,262,157 B2 * | 8/2007 | Utz et al. .................. 510/121 |
| 7,439,214 B2 * | 10/2008 | Utz et al. .................. 510/121 |
| 7,704,934 B2 * | 4/2010 | Lepilleur .................. 510/121 |
| 7,759,296 B2 * | 7/2010 | Lepilleur et al. ............ 510/121 |
| 7,923,422 B2 * | 4/2011 | Lepilleur .................. 510/121 |
| 8,003,585 B2 * | 8/2011 | Lepilleur et al. ............ 510/121 |
| 2005/0075497 A1 * | 4/2005 | Utz et al. .................. 536/114 |

\* cited by examiner

SHAMPOO COMPOSITIONS

CROSS REFERENCE TO RELATED APPLICATION

This application is a continuation in part of copending U.S. patent application Ser. No. 11/014,424, filed on Dec. 16, 2004 which is a continuation in part of 10/871,472 filed on Jun. 19, 2004 which claims the benefit of priority under 35 U.S.C. §119 of European Patent Application No. 03013933.1, filed on Jun. 20, 2003.

FIELD OF THE INVENTION

The present invention relates to substantially pure hydrocolloids obtained from the endosperm of seeds (hereinafter "hydrocolloids"), a method of obtaining said hydrocolloids, and compositions comprising said hydrocolloids. More specifically, the present invention relates to a method for obtaining galactomannan hydrocolloids wherein the hydrocolloids are colorless, odorless, tasteless, and substantially free of anthraquinones and exhibit improved performance parameters such as increased viscosity, gel strength and break strength properties. The invention further relates to hydrocolloids obtained by the process of the invention that have been derivatized by anionic, cationic, nonionic and/or amphoteric substituents. The hydrocolloids and derivatized hydrocolloids of the invention can be employed as gelling and binding agents thickeners, stabilizers, emulsifiers, spreading and deposition aids and carriers for enhancing the rheology, efficacy, deposition, psychosensory, aesthetic and delivery of chemically and physiologically active ingredients in food and fodder, personal care, health care, pharmaceutical, household, institutional and industrial compositions in which they are included.

BACKGROUND OF THE INVENTION

Hydrocolloids are derived from polysaccharides that can be extracted from the endosperm of seeds from plants, shrubs and trees of the families Leguminosae and Fabraceae. The seeds of the tamarind tree, *Tamarindus indica* L. (tamarind gum); Greek hay, *Trigonella foenum-graecum* L. (fenugreek gum); wild senna and sicklepod plants, *Cassia tora* and *Cassia obtusifolia* (cassia gum); the carob tree *Ceratonia siliqua* L. (locust bean gum); the tara bush *Caesalpinia spinosa* L. (tara gum), and the guar plant *Cyamopsis tetragonoloba* L. (guar gum) are common sources for endosperm material. The polysaccharides obtained from these seeds are known to act as thickening and gelling agents in aqueous systems. The polysaccharides obtained from fenugreek gum, cassia gum, locust bean gum, tara gum, and guar gum are known as polygalactomannans. A polygalactomannan is composed of 1→4-linked β-D-mannopyranosyl units with recurring 1→6-linked α-D-galactosyl side groups branching from the number 6 carbon of a mannopyranose residue in the backbone. The galactomannan polymers of the different species of the Leguminosae and Fabraceae families defer from one another in the frequency of the occurrence of the galactosyl side units branching from the polymannopyranose backbone. The average ratio of D-mannosyl to D-galactosyl units in the polygalactomannan contained in fenugreek gum is approximately 1:1, in guar gum approximately 2:1, for tara gum approximately 3:1, for locust bean gum approximately 4:1, and approximately 5:1 for cassia gum. For illustrative purposes, the polygalactomannan obtained from cassia gum is schematically represented in the structure below.

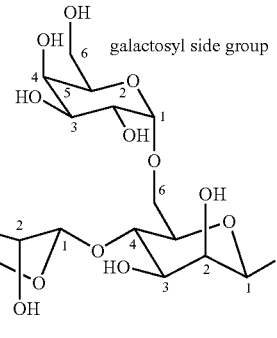

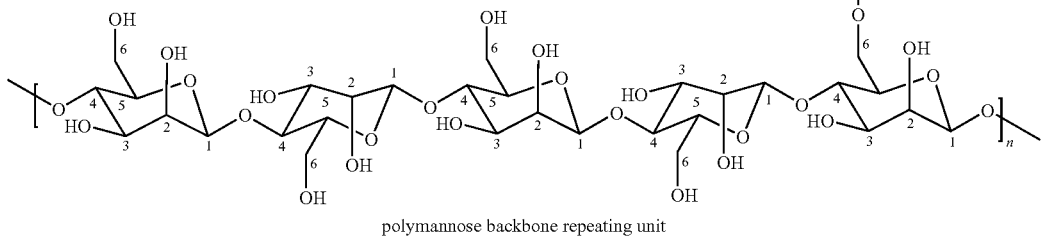

polymannose backbone repeating unit wherein n represents the number of repeating units in the galactomannan polymer. In one embodiment, n represents an integer from about 10 to about 50. In another embodiment, n represents and integer from about 15 to about 35, and in still another embodiment from about 20 to about 30. In still another embodiment of the invention, the polygalactomannan of the invention has a number average molecular weight of at least 100,000. In another embodiment, the number average molecular weight ranges from about from about 150,000 to about 500,000, and in still another embodiment from about 200,000 to about 300,000 (molecular weights determined by GPC method using a polystyrene standard). In a further embodiment of the invention, the number average molecular weight can range from 500,000 to over 1,000,000.

Typically, the endosperm flour extracted from the seeds of *cassia*, locust bean, tara and guar contains 3 to 12% water, up to 2% fat, up to 7% raw protein, up to 4% raw fiber, up to 2% ash, and at least 75% residual polysaccharide. It has always been a desire to prepare a purer galactomannan with improved its properties to broaden the spectrum of its use such as, for instance, for use in food products for human and animal consumption, as well as in personal care, pharmaceutical, homecare, and industrial compositions. For example, in prior processes, *cassia* flour was extracted from the seeds of *Cassia tora* or from *Cassia obtusifolia* by heating the ripe seeds followed by subjecting them to mechanical stress such as crushing or grinding. This treatment resulted in the pulverization of the germ and the endosperm hull. The intact seed endosperm was isolated from the seedling and hull fragments by sifting and then was subjected to a pulverization process such as described in. U.S. Pat. No. 2,891,050. Although the *cassia* endosperm flour isolated in this way had the desired gelling properties, it nonetheless retained a specific fruity aroma and a slightly bitter taste. Moreover, the flour had a yellow to slight-brown color so that its use in the production of products requiring high clarity was limited.

In German published patent application DE 3335593, gelling and thickening agents based on a mixture of *cassia* galactomannans and carrageenan, agar and/or xanthan are disclosed.

German published patent application DE 3347469 describes substituted alkyl ethers of the polysaccharides that appear in the endosperm of *cassia tora* and their use as a thickening agent in printing pastes for textile printing.

German published patent application DE 3114783 discloses the production of carob pod, carob kernel or guar flour with an improved taste. In the disclosed process, the dried (and where applicable, toasted and ground) base material is subjected to high-pressure extraction with supercritical carbon dioxide. However, the application of this process to *cassia* flour yields inadequate results.

Heretofor, it has not been possible either through selective pulverization and other mechanical purification processes to successfully produce galactomannan flour such as *cassia* flour which is substantially colorless, odorless and tasteless and which is largely free of anthraquinones while maintaining gelling properties. For this reason, the *cassia* flour produced by the prior methods is unsuitable as an additive for high purity, sensorily sophisticated food products.

U.S. Pat. No. 4,840,811 discloses a process for producing *cassia* endosperm flour from the endosperm of *Cassia tora*. The obtained product is colorless, odorless and tasteless. In the disclosed method, the endosperm is solvent extracted at least once to reduce impurities such as derivatives of anthraquinones. The extraction solvent comprises a mixture of water and an alkanol and/or acetone. Following drying, the endosperm is converted to a desired degree of fineness.

Independent from the fact that the gelling agent should provide food products with a gelatinous consistency while not affecting the product in terms of taste, odor and color properties, it has been found that the final hydrocolloid resulting from prior art processes still contains certain phytochemicals, in particular, derivatives of anthraquinones. This class of compounds has been identified as potentially hazardous to human health (S. O. Mueller, et al., "Food and Chemical Toxicology" 37 (1999), pages 481 to 491).

Typical anthraquinone derivatives suspected of causing undesirable health effects are 1,8-hydroxy anthraquinones such as physcion, chrysophanol, aloe-emodin and rhein as represented by the following formula:

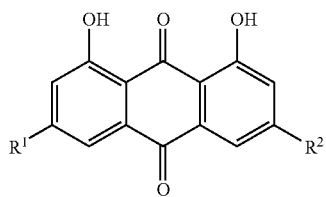

| | | |
|---|---|---|
| Physcion | $R^1 = OCH_3$ | $R^2 = CH_3$ |
| Aloe-emodin | $R^1 = H$ | $R^2 = CH_2OH$ |
| Rhein | $R^1 = H$ | $R^2 = COOH$ |
| Chrysophanol | $R^1 = H$ | $R^2 = CH_3$ |

As discussed above, U.S. Pat. No. 4,840,811 is directed to a method for reducing the level of anthraquinones in *cassia* gums because of anthraquinones deleteriously affect odor, taste and color. The '811 disclosure does not recognize the toxicity problem inherent in the presence of anthraquinones in the gum. However, in order to provide a *cassia* hydrocolloid which can be safely used for food, fodder, pharmaceutical and personal care purposes, it is imperative that the hydrocolloid it is substantially free of potentially hazardous anthraquinones.

U.S. Pat. No. 5,801,116 discloses a process for the treatment of guar splits with water to hydrate the splits and then grinding the hydrated split in a laboratory grinder. The ground split is then dried in a bed drier.

V. P. Kapoor, et al. (Carbohydrate Research, 306 (1998), pages 231 to 241) discloses separating endosperm from the seeds of *Cassia* spectabilis by dry and wet milling processes using various mixers, sieves and grinders. The crude gum, isolated through the dry/wet milling process is subsequently purified by dispersing the gum in water and precipitating the product with ethanol.

U.S. Pat. No. 2,891,050 discloses a process for the production of mucilaginous material from leguminous seeds such as guar, tara and locust bean comprising the steps of tempering the endosperm obtained to a moisture content of 30 to 60% water and flattening the moisturized endosperm by passing it between rollers. In a subsequent step the flattened endosperm is dried and ground. This process is known In the art as the "flaking/grinding" process. The galactomannans prepared according to this process are used as additives in the manufacture of paper, salad dressing, ice cream, bakery products and other foodstuffs.

German published patent application DE 10047278 discloses that endosperm flour of *Cassia* seeds can be obtained by subjecting the seeds to simple milling processes to separate the endosperm from the husks, followed by grinding the endosperm to yield a desired particle size. It is further disclosed that blending the ground endosperm of *Cassia obtusifolia/tora* with other hydrocolloids such as carrageenan, xanthan, agar or polyacrylates results in improved gelling and thickening properties.

DESCRIPTION OF EXEMPLARY EMBODIMENTS

Figure 1:
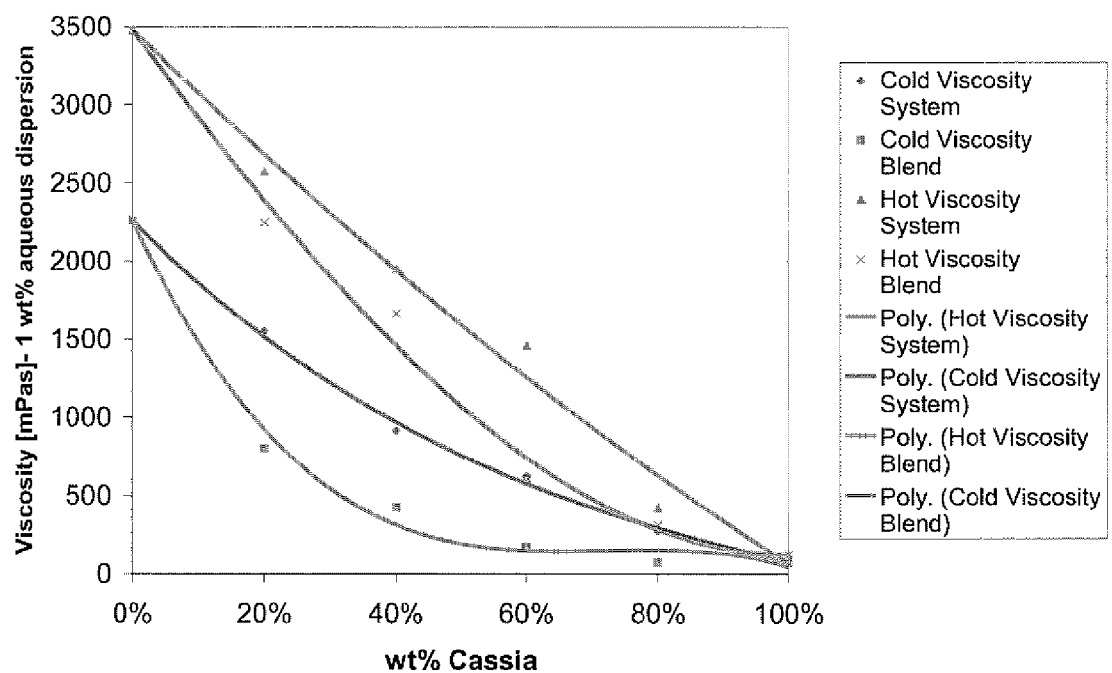
FIG. 1 is a plot comparing the hot and cold viscosity values of a co-minced *cassia*/guar hydrocolloid prepared by the process of the invention with a conventional blend of individually minced *cassia* and guar.

Exemplary embodiments in accordance with the present invention will be described. Various modifications, adaptations or variations of such exemplary embodiments described herein may become apparent to those skilled in the art as such are disclosed. It will be understood that all such modifications, adaptations or variations that rely upon the teachings of the present invention, and through which these teachings have advanced the art, are considered to be within the scope and spirit of the present invention.

In one aspect, embodiments of the present invention relate to a process for obtaining hydrocolloids from the endosperm of seeds. Some exemplary embodiments in accordance with the present invention relate to a process for obtaining galactomannan hydrocolloids of *cassia*, locust bean, tara and guar that exhibit improved properties compared to the respective state of the art hydrocolloids.

Other aspects of the invention relate to derivatizing the hydrocolloids obtained by the process of the invention with cationic, amphoteric and/or nonionic groups. Still other exemplary embodiments of the invention relate to a process for providing high purity galactomannan hydrocolloids such as *cassia* hydrocolloids that are substantially free of potentially hazardous anthraquinones. Other embodiments relate to methods for processing hydrocolloids of the invention in presence of one or more polysaccharides of differing composition. Yet other such embodiments relate to the use of hydrocolloids prepared by the processes of the invention as gelling and binding agents thickeners, stabilizers, emulsifiers, spreading and deposition aids and carriers for enhancing the rheology, efficacy, deposition, psychosensory, aesthetic and delivery of chemically and physiologically active ingredients in food and fodder, personal care, health care, pharmaceutical, household, institutional and industrial compositions.

In one exemplary embodiment, the present invention relates to a method for making hydrocolloids comprising the steps of:

(i) swelling at least one split selected from tamarind, fenugreek, *cassia*, locust bean, tara or guar with water to form a swollen split composition; optionally followed by dispersing the swollen split composition in a water/organic solvent mixture, and (ii) at least one step of wet-mincing the composition obtained under (i).

In another exemplary embodiment of the invention, the method further comprises the steps of:

(iii) adding the minced and swollen split composition obtained in step (ii) to a mixture of water and an organic solvent; and (iv) separating the water/organic solvent mixture from the minced split composition to obtain a galactomannan hydrocolloid.

Typically, in step (i) the swollen split is in the form of particles which are dispersed (suspended) in the water or water/organic solvent mixture. In one alternative embodiment of the invention, the swelling step (i) can be carried out in the water/organic solvent mixture described below for the optional dispersion step set forth under step (i).

In one embodiment of the invention, the water used for swelling the split in step (i) comprises a derivatizing agent capable of reacting with at least one hydroxyl group on the polysaccharide backbone. In another embodiment, the hydroxyl group is located on the C-6 carbon atom of the mannosyl and/or galactosyl residues of the polygalactomannan backbone of the split. The derivatizing agent is capable of appending a nonionic, cationic, anionic or amphoteric substituent, and combinations thereof on the backbone.

In the optional embodiment referred to above, the amount of organic solvent in said water/organic solvent mixture of step (i) is at least about 30 percent by weight.

In an alternative embodiment in the method described above at least two different endosperm splits, such as, for instance, splits of *cassia* and guar are utilized as the endosperm source. In a further embodiment of the invention, at least one galactomannan split and at least one other polysaccharide source are processed together in the method of the invention.

Another aspect of the invention relates to a method for reducing the amount of impurities in hydrocolloids, in particular, polygalactomannan hydrocolloids. Impurities include, for example, fiber and various chemical compounds that are naturally present in the seed endosperm of hydrocolloid source material. As discussed above, anthraquinone derivatives, particularly, hydroxyl substituted anthraquinone derivatives (physcion, chrysophanol, aloe-emodin, and rhein), are undesirable components in polygalactomannan hydrocolloids. Accordingly, it is desirable to remove these components from the hydrocolloid product. An additional embodiment of the invention is directed to a method of removing impurities from galactomannan hydrocolloids comprising the steps of:

(i) swelling at least one split of a polygalactomannan with water;

(ii) at least one step of wet-mincing the swollen split;

(iii) introducing the minced and swollen split into a mixture of water and an organic solvent;

(iv) separating the water/organic solvent mixture from the split to obtain a purified galactomannan hydrocolloid.

In step (iii) above impurities in the minced and swollen split composition are extracted into the water/organic solvent phase of water.

In an alternative embodiment, steps (ii) and (iii) can be carried out at the same time, resulting in the following alternative method:

(i) swelling at least one split of a polygalactomannan with water;

(ii) introducing the swollen split into a mixture of water and an organic solvent and wet-mincing the swollen split; and (iii) separating the water/organic solvent mixture from the split to obtain a purified polygalactomannan hydrocolloid.

The processes of the present invention yield hydrocolloid compositions with improved aesthetic properties such as transparency (clarity), turbidity, odor, taste and color, as well as improved physical properties such as viscosity, break strength (also referred to as outer gel strength), gel strength (often referred to as inner gel strength) and purity.

In one embodiment of the invention, the hydrocolloids obtained by the method of the present invention are derived from the endosperm of seeds of the family Leguminosae and Fabraceae. In another embodiment of the invention, the seeds of *Tamarindus Indica, Trigonella foenumgraecum, Cassia tora, Cassia obtusifolia, Ceratonia siliqua, Caesalpinia spinos, Cyamopsis tetragonoloba*, and mixtures thereof can be utilized as sources for endosperm material for the process.

As used here and throughout the specification, the term "split" denotes the crude (raw or unprocessed) endosperm flour of tamarind, fenugreek, *cassia*, locust bean, tara or guar that has not undergone any further treatment. As known in the art, the term split is often used interchangeably with the term "endosperm". The splits of tamarid, fenugreek, *cassia*, locust bean, tara and guar are commercially available on the market. Typically, *cassia* is selected from *Cassia tora, Cassia obtusifolia* or combinations thereof. In nature *Cassia tora* and *Cassia obtusifolia* coexist in the same field and are typically co-harvested.

As used here and throughout the specification, the term "galactomannan" is used interchangeably with the term "polygalactomannan".

As used here and throughout the specification, the terms modified, functionalized, derivatized, molecularly substituted and molecular substitution are used interchangeably and mean appending a substituent selected from nonionic, anionic, cationic, and amphoteric containing moieties, and combinations thereof, to one or more hydroxyl groups contained on the polysaccharide backbone. In one embodiment of the invention, the hydroxyl group is situated on the C-6 carbon atom of the galactosyl and/or the mannosyl repeating units of the polygalactomannan.

The water used for swelling the endosperm may contain additives selected from the group consisting of an alkalinity source, such as sodium hydroxide, potassium hydroxide; an acidity source, such as citric acid, acetic acid and ascorbic acid; buffers and buffering systems; enzymes such as proteases, neutrases, alkalases, pepsin; alkali metal salts, such as sodium or potassium chloride; or alkaline earth metal salts, such as calcium chloride, or combinations of said additives.

Additionally and independently, agents to derivatize the galactomannan can be contained in the water used for swelling alone or in combination with the additives mentioned above. Functionalization reagents containing these moieties are reacted with a hydroxyl group that is bonded to one or more of the hydroxyl groups of the galactose and mannose residues that make up the polygalactomannan. An exemplary derivation reaction utilizing a *cassia* derived galactomannan is schematically represented below:

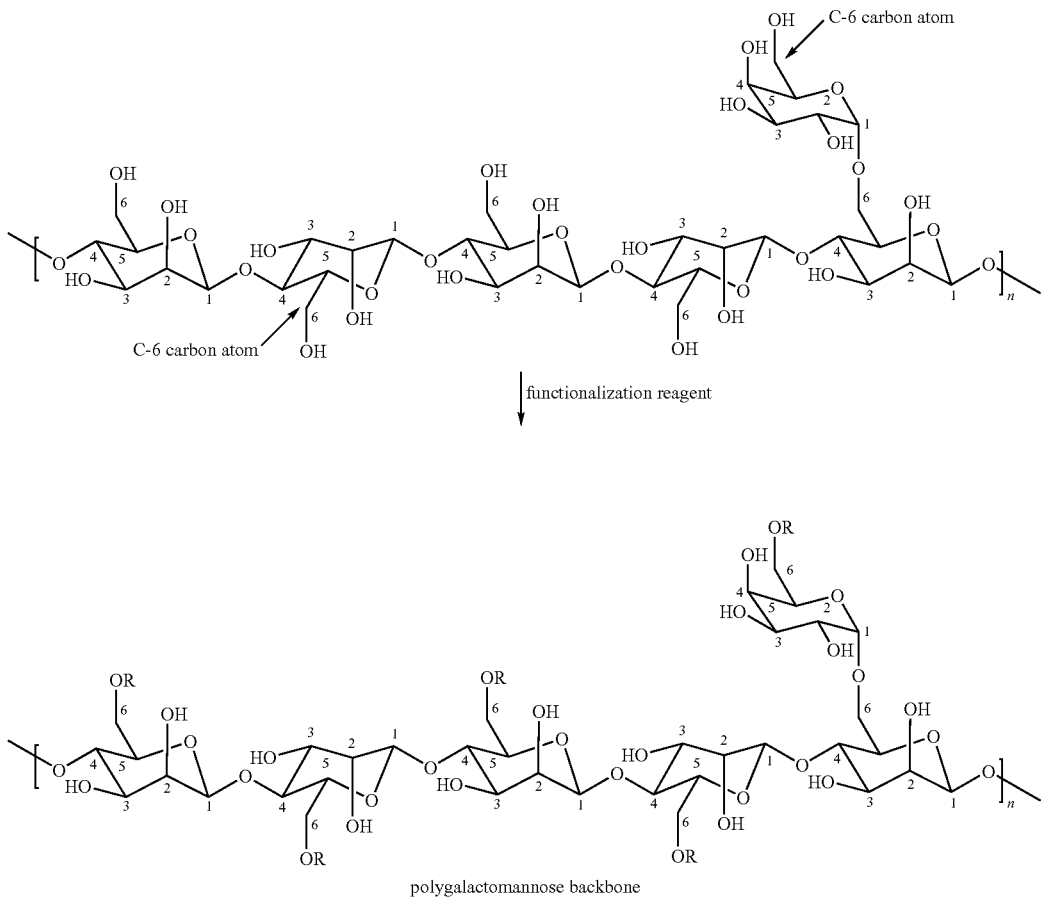

polygalactomannose backbone

In some embodiments of the invention, R independently represents a hydrogen, a nonionic group, an anionic group, a cationic group, and an amphoteric group. In another embodiment, R is a cationic group. In other embodiments, R independently is selected from the formula:

—$AR^1$ wherein A is an alkylene spacer group containing 1 to 6 carbon atoms and $R^1$ represents a nonionic substituent, an anionic substituent, a cationic substituent, and an amphoteric substituent. In another embodiment, the alkylene group contains 2, 3, 4, or, 5 carbon atoms. The alkylene spacer is optionally mono-substituted or multi-substituted with a group selected from $C_1$ to $C_3$ alkyl, $C_1$ to $C_3$ haloalkyl, $C_1$ to $C_3$ hydroxyalkyl, hydroxyl, halogen (bromine, chlorine, fluorine, and iodine), and combinations thereof. An exemplary nonionic $R^1$ substituent is —OH. Illustrative nonionic groups defined under —$AR^1$ can be represented by the formula:

-alkylene-OH wherein the alkylene spacer is defined above. Representative nonionic groups include but are not limited to hydroxymethyl, hydroxyethyl, hydroxypropyl, and hydroxybutyl, wherein the alkylene spacer is as defined above. Another exemplary nonionic substituent under $R^1$ is the alkyl ether group:

-alkylene-O-alkyl wherein alkylene spacer is as defined above, and the alkyl group can be linear or branched and contains 1 to 6 carbon atoms. In another embodiment, the alkyl group contains 1 to 4 carbon atoms. The ethers can be prepared from the respective alkyl halides or the diazo compounds in a known manner.

Exemplary anionic $R^1$ substituents are —COOH, —$SO_3H$, —OP(O)(OH)(OH), and —P(O)(OH)(OH). Illustrative anionic groups defined under —$AR^1$ can be represented by the formulae:

-alkylene-COOH

-alkylene-$SO_3H$

-alkylene-OP(O)(OH)(OH)

-alkylene-P(O)(OH)(OH)

wherein the alkylene spacer is as defined previously. Representative anionic groups include but are not limited to carboxymethyl, carboxyethyl, carboxypropyl, and the like.

Exemplary cationic substituents under $R^1$ include primary, secondary, and tertiary amines represented by the radical: —$N(R^2)_2$, and quaternary ammonium, sulfonium and phosphonium derivatives represented by the radicals: —$N(R^3)_3{}^+X^-$, —$S(R^3)_2{}^+X^-$, —$P(R^3)_3{}^+X^-$, wherein $R^2$ independently represents hydrogen, linear and branched $C_1$ to $C_5$ alkyl, phenyl and benzyl; $R^3$ independently represents $C_1$ to $C_{24}$ alkyl, preferably $C_1$ to $C_{12}$ alkyl, $C_1$ to $C_8$ alkyl, benzyl and phenyl; and X is any suitable anion that balances the charge on the onium cation. In one preferred embodiment, X is a halide anion selected from bromine, chlorine, fluorine and iodine. The alkyl, benzyl and phenyl substituents defined under $R^2$ and $R^3$ can optionally be mono-substituted or multi-substituted with a group selected from $C_1$ to $C_3$ alkyl, hydroxyl, halogen (bromine, chlorine, fluorine, and iodine), and combinations thereof. Illustrative cationic groups defined under —AR[1] can be represented by the formulae:

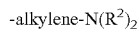

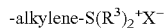

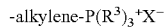

wherein alkylene, $R^2$, $R^3$, and X are as previously defined. Representative cationic groups under —AR[1] are quaternary ammonium groups that include but are not limited to the formula:

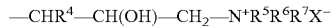

wherein $R^4$ is selected from hydrogen and chlorine; $R^5$, $R^6$, and $R^7$ are independently selected from hydrogen and linear and branched $C_1$ to $C_{20}$ alkyl groups; and $X^-$ represents halide. In one embodiment of the invention, at least one of $R^5$ and $R^6$ is hydrogen or methyl. In another embodiment both of $R^5$ and $R^6$ are hydrogen, and in a further embodiment $R^5$ and $R^6$ are methyl. In a still further aspect of the invention $R^7$ is selected from $C_{10}$ to $C_{20}$ alkyl groups. Representative alkyl groups are decyl, dodecyl, butadecyl, cocoalkyl, dodecyl, and octadecyl. Representative halogen groups are chloride and bromide. Typical cationizing agents are 3-chloro-2-hydroxypropyl-trimethylammonium chloride and 2,3-epoxypropyl-trimethylammonium chloride.

The amphoteric substituents can be selected from any radical or residue that contains both a positive and negative charge. Representative amphoteric substituents include betaine, amino acids, dipeptides, tripeptide and polypeptide residues.

Similarly, the hydroxyl groups on the polysaccharide or polygalactomannan backbone can be non-ionically derivatized by reacting the hydroxyl groups with ethylene oxide (EO) and/or propylene oxide (PO) to form the respective hydroxyethyl and/or hydroxypropyl ether substituents.

The derivatization of the polygalactomannan such as at the C-6 hydroxyl group can be accomplished by methods well known to those skilled in the art. Generally speaking, the C-6 hydroxyl group can be reacted with any functionalization reagent that is reactive therewith. For example, to functionalize the C-6 hydroxyl group with the nonionic, anionic, cationic and amphoteric substituents of the invention, the C-6 hydroxyl group(s) on the polygalactomannan is/are reacted with a functionalization reagent that contains the respective nonionic, anionic, cationic and amphoteric substituent and a functional moiety that is reactive with the C-6 hydroxyl group. The functionalization reaction is conducted in an appropriate solvent and at an appropriate temperature. The amount of functional group substitution (degree of substitution) on the polygalactomannan C-6 hydroxyl atom(s) can be controlled by adjusting the stoichiometric amount of functionalization reagent added to the polygalactomannan. Functionalization methods for galactomannans (e.g., *cassia*) are disclosed, for example, in U.S. Pat. No. 4,753,659, the disclosure of which is hereby incorporated by reference. Additional methods for derivatizing polygalactomannans are set forth in U.S. Pat. No. 5,733,854, the disclosure which is also incorporated herein by reference.

Generally, the modification of the galactomannans can be accomplished by reacting the galactomannan with the respective polyethers, alcohols, carboxylic, sulfonic, phosphoric, phosphonic acids, the primary, secondary, or tertiary ammonium compounds, the sulfonium or phosphonium compounds or an amphoteric compound selected from Z-A-R[1] wherein A and R[1] are as defined previously and Z represents a leaving group selected from epoxy or epoxyalkyl, halohydrin group, halogen (e.g., chloro, bromo, iodo), $C_1$ to $C_6$-alkyl, $C_6$ to $C_8$ aryl sulfonyloxy, $C_1$ to $C_6$-alkyl, $C_6$ to $C_8$-aryl sulfate, and $C_1$ to $C_6$-alkoxy. In one embodiment of the invention, Z can be benzenesulfonyloxy, trifluoromethanesulfonyl, p-toluenesulfonyloxy, methanesulfonyloxy, or t-butoxy.

In an exemplary reaction, *cassia* gum polygalactomannan can be functionalized with co-reactive quaternary ammonium compounds which contain an epoxy group or a halohydrin group. In one such embodiment *cassia* polygalactomannan can be reacted with glycidyltrimethylammonium chloride (75% aqueous solution) in an alkaline aqueous medium at a temperature of about 52° C. to yield the desired 2-hydroxy-3-(trimethylammonium)propyl *cassia* galactomannan chloride product. The reaction is schematically represented below:

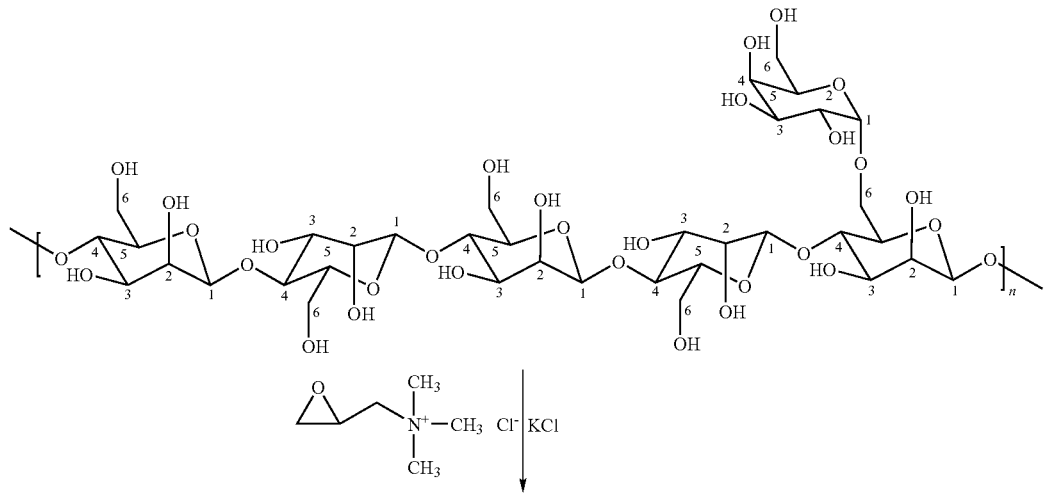

-continued

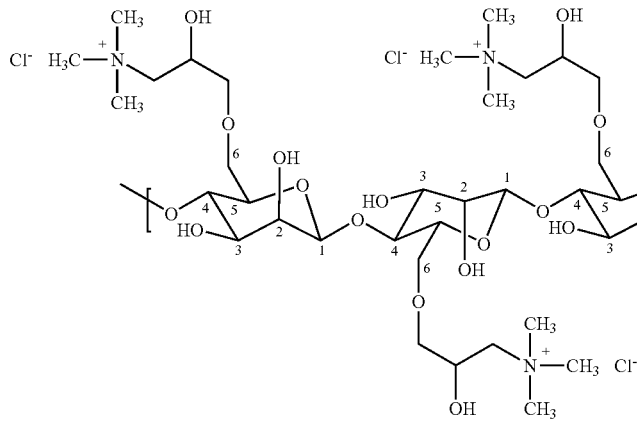
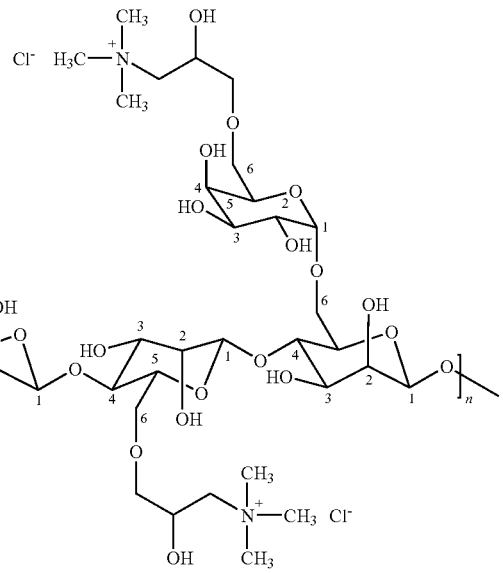

Chemical modification of the polygalactomannans leads to incorporation of nonionic, anionic, cationic, and amphoteric moieties, and combinations thereof onto the backbone. The chemical modification leads to various physical properties changes. For instance, derivatized *cassia* gums exhibit cold water or improved cold water solubility. It is able to hydrate in cold water and build viscosity by forming a colloidal thixotropic dispersion in cold water. A typical example for a polygalactomannan hydrocolloid which has been derivatized by a cationic substituent is *cassia* hydroxypropyl trimethylammonium chloride resulting from the reaction of *cassia* galactomannan with 2,3-epoxypropyltrimethyl ammonium chloride by the method according to the invention. Contrary derivatized galactomannans obtained according to the methods of the prior art the raw material of the invention is soluble in cold water. Depending on the degree of substitution the performance characteristics can be tailor-made. Thus a cationic *cassia* with a degree of substitution such as 1.0 or less is easily soluble in cold water and, in addition, has high transparency.

In one embodiment of the invention, the degree of substitution can range between about 0.05 and about 3.0. In another embodiment the degree of substitution can range between about 0.1 and about 1.5, and in a further embodiment between about 0.3 and about 1.0. The term "degree of substitution" is defined as the average number of functional substituents appended on a residue in the polysaccharide backbone, e.g., on the mannosyl and galactosyl residues in galactomannan polymer. The maximum available degree of substitution is 3 because each residue in the backbone contains 3 potentially derivatizable hydroxyl groups.

In an embodiment of the present invention, the weight ratio of water (optionally containing the additives and/or the derivatizing agents mentioned above) to flour (split) is at least about 1.5 to 1, and in another embodiment at least about 2 to 1. The weight ratio of water to flour should not exceed about 5 to 1 in one embodiment and about 4 to 1 in another embodiment (the weight ratios utilized In this description refer to the weight ratio of water to dry flour).

The pH-value of the aqueous phase in the swelling step ranges between about 5 and up to about 13, and in another aspect between about 6 and up to about 8.

The swelling step takes between about 5 and 120 minutes in one aspect of the invention, and between about 10 and 80 minutes in another aspect. In a further aspect of the invention, the swelling step ranges between about 20 and 60 minutes. The water used to swell the split has a temperature range of between about 15 and 100° C., preferably up to about 50° C., most preferably between about 20 and 40° C. The mass can be stirred while swelling, the water used to swell the split can be added in total at the beginning of the step or metered in while stirring. Ideally, the water is added until no further swelling takes place.

According to one embodiment of the invention, the swollen endosperm obtained in step (i) is not dried but is subjected to a wet-mincing step (ii) as is. In an alternative embodiment of the invention, the swollen endosperm is dispersed in a water/organic solvent mixture to form a dispersion. The amount of organic solvent in said water/organic solvent mixture is at least about 30, 35, 40, 45, 50, 55, 60, percent by weight. In another embodiment, the amount of solvent in the water/organic solvent mixture can range from 70 to 95 percent by weight based on the water/organic solvent mixture, and in a further embodiment can be 80 percent by weight.

The weight ratio of swollen endosperm (split) to water/organic solvent mixture is between about 1:3 to about 1:10 in one aspect, and between about 1:5 and about 1:8 in another aspect of the invention.

The organic solvent present in the water/organic solvent mixture used in the optional dispersion step (iii) is selected from the group of solvents that are miscible with water and that are not deleterious to health and safety. Acetone, methanol, ethanol, n-propanol, iso-propanol and mixtures thereof can be employed as the solvent. An ideal organic solvent for food, fodder, personal care and health care applications such as pharmaceutical purposes is iso-propanol or ethanol. A suitable ratio of water:iso-propanol is between about 15:85 and about 85:15 in one aspect of the invention, and between about 25:75 and about 50:50 in another aspect (all ratios are on a wt. to wt. basis). In a further aspect, the ratio of water to isopropanol can be about 30:70 (wt./wt.).

As used here and throughout the specification, the term "swollen split" is meant to encompass the swollen split itself or the swollen split that has been dispersed in the water/organic solvent mixture which is described above as an alternative embodiment of this invention.

For wet-mincing the swollen endosperm or, alternatively, the dispersion of the swollen endosperm in the water/organic solvent mixture, any mincing apparatus can be used which is suitable for mincing gummy or viscous materials. Exemplary mincing apparatuses are mincers or masticators, and cutting mills. Conventional meat mincers can be employed to mince or wet mince the swollen split. These devices are well known the meat processing industry. In one embodiment of the invention, a Jupiter Model 885 meat mincer (Jupiter Kuechenmaschinenfabrik GmbH & Co.) is utilized to mince the swollen split. The impact exerted by these machines on the product to be processed is low due to the low shear developed by these apparatuses. Generally, the temperature of the product processed by mincing does not raise significantly, typically not more than by about 5° C. This distinguishes meatmincers from conventional extruders exerting high pressures and shear upon the processed product, resulting in a significant raise of the temperature of the processed product. Thus, for the purpose of this invention "mincing" refers to an activity which is carried out under the mincing conditions described above in a mincing apparatus which can be represented by, in its simplest form, a meat-mincer. Of course, similar types of apparatus of any size and capacity providing for the mincing conditions described above are likewise suitable.

As used here and throughout the specification, term "mincing" and not "grinding" or "pulverizing" is employed. The term "grinding" is defined to denote a forceful tearing action exerted on the endosperm flour. Thus, by definition of this invention and the generally accepted definition in the lexicon, for instance, *The American Heritage Dictionary* (1985, Houghton Mifflin Company) "mincing" is defined to denote an action of cutting or chopping into very small pieces. This is in sharp contrast to "grinding" or "pulverizing" which are employed in conjunction with the prior art processes. Grinding denotes an action of crushing, pulverizing or powdering by friction, especially by rubbing between two hard surfaces. Furthermore, "mincing" also is to be distinguished over "milling" which denotes an act of grinding, for example, grain into flour or meal. Thus, methods involving milling and grinding steps on the swollen split are specifically excluded from the scope of this invention.

Employing a mincing apparatus the swollen split, or a dispersion of the swollen split, is forced through a disk (cutting disk) which has a multiplicity of perforations. In one embodiment, the perforations have a diameter of about 5 mm or less and in different embodiments can be about 4 mm or less, about 3.5 mm or less, about 3 mm or less, about 2.5 mm or less, and about 2 mm or less. For the initial mincing step using perforation diameters of less than about 2 mm have been proven to be inefficient. This is due to the high viscosity of the initial swollen mass. Smaller diameters may, however, be advantageous for an optional second, third or fourth or additional mincing step. The perforated disk can comprise a rotating cutting blade that cuts the split material as it passes through the perforated disk. The mincing step can be a multistep mincing process with or without intermediate additional swelling steps in between the individual mincing steps.

In one embodiment, the present invention relates to a method comprising at least two consecutive wet-mincing steps wherein the diameter of the perforations decreases with the succession of mincing steps. For instance, the diameter of the perforations in the disk is reduced by about 1 mm or 0.5 mm per successive mincing step. In one embodiment, the diameter of the perforation employed in the initial mincing steps is decreased with each successive mincing step in the following order 5, 4 and 3 mm. The diameter of the perforation in the final mincing steps is again decreased in the following order 2.5, 2, 1.5, 1, and 0.5 mm. In alternative embodiments, successive mincing steps can be carried out in conjunction with the same diameter perforated disk dimensions before proceeding to a mincing step utilizing a smaller diameter perforated disk. In alternative embodiments, the dispersion of the swollen splits as described above can be formed before the first, second, or any successive mincing step. If the dispersion option is employed, the dispersion is ideally formed prior to the first mincing step.

Step (iii) of the process can also be referred to as the extraction step. The minced and swollen split is added to the water/organic solvent mixture while stirring. The amount of organic solvent utilized in the water/organic solvent mixture in step (iii) (if employed for the first time directly after wetmincing) can range from about 30 to about 60 percent by weight based on the total weight of the water/organic solvent mixture. In varying embodiments, the amount of solvent present in the water/organic solvent mixture is at least about 30, 35, 40, 45, 50, 55, or 60 percent by weight, based on the total weight of the water/organic solvent mixture.

In one embodiment of the invention steps (iii) to (iv) are repeated at least twice, i.e., the semi-refined hydrocolloid which has been separated from the water/organic solvent mixture (for instance by filtration), is introduced (suspended) again into a water/organic solvent mixture under agitation. In one embodiment, the amount of the organic solvent in the water/organic solvent mixture is increased in each successive step. For example, in the second extraction step, the amount of organic solvent present in the water/organic solvent mixture is increased by about 10 to 30 percent by weight. Thus, in an exemplary embodiment of the invention the amount of organic solvent in the water/organic solvent mixture in the first soaking/washing step (extraction step (iii)) is about 50% by weight, and in a succeeding extraction step the amount of the organic solvent is about 70% by weight, and in the succeeding extraction steps the amount of solvent is increased to about 80, 85, or even 90% by weight. In an embodiment of the invention steps (iii) and (iv) are repeated three times.

If multiple successive extraction steps are employed, the organic solvent in the water/solvent mixture of the final extraction step can range from about 80 to about 95% by weight based on the weight of the water/solvent mixture.

In an alternative embodiment, small quantities of up to about 1% by weight of a reducing agent may be added to the extraction liquid. Exemplary reducing agents are dithionites, sulfites, ascorbic acid, cysteine and cysteine derivates, and the like.

In still another embodiment, small quantities of a soluble alkaline material can be added to the extraction liquid. Exemplary alkaline materials include alkali carbonates, sodium hydroxide, potassium hydroxide, and ammonia.

These additives, i.e., reducing agents and/or alkaline substances allow for a better separation of the undesirable substances from the split material. Thus, the desired hydrocolloid can be obtained in a highly pure form.

The swollen split is kept in the water/organic solvent for a time sufficient to extract the undesirable components from the split, typically from about 1 minute to about 60 minutes.

The extraction can be conducted in batch or continuously. In one embodiment, countercurrent extraction can be employed. Exemplary extraction equipment can be selected from percolators, band extractors, rotation extractors and similar devices.

The separation step (iv) can be carried out by using any conventional method suitable for separating a solid from a liquid, such as, for instance a conventional gravity filter arrangement with optional pressure or suction. In an alternative embodiment, the water/organic solvent mixture can be removed by centrifugation.

Typically, after removing the water/organic solvent mixture from the hydrocolloid obtained either in step (ii) or (Iv) of the method of the invention, the solids content of the hydrocolloid is between about 20 and 70% in one embodiment and about 40 to 60% in another embodiment. Generally, the level of solids in the hydrocolloid can be adjusted according to the end use of the product. As will be described below, the hydrocolloid can also be dried following the separation step.

In an optional embodiment of the method of the present invention, step (i) can be preceded by a washing step. Typically, the washing is carried out by rinsing the endosperm flour with water. The washing step can be carried out in a container or by rinsing the flour on a retention screen.

In an alternative embodiment, step (ii) and/or step (iv) can be followed by a drying step. Drying the moist hydrocolloid can be carried out in any state of the art drying apparatus. Exemplary dryers include thermic fluid dryers, pipe dryers and vacuum dryers. For ease of handling and packaging, subsequent to wet-mincing step and the drying step, the galactomannan can be ground to yield a fine powder without deleteriously affecting the properties of the obtained product. In this optional embodiment, the maximum particle size can be less than about 500 µm in one aspect, and less than about 250 µm in another aspect. As referred to here and throughout the specification, the term "dry galactomannan hydrocolloid" or "dry galactomannan" means that the water content is less than about 15% by weight in one embodiment, and less than about 12% by weight in another embodiment. Typically, in the art the definition of "dry" can vary depending on the respective galactomannan hydrocolloid.

The methods according to the present invention can be carried out as a continuous or batch process.

In one embodiment, a polygalactomannan obtainable by the method according to the present invention is cassia and guar gum. In an alternative embodiment, the cassia and guar processed in accordance with the method of the present invention can be cationically modified by the cationic substituents discussed previously. Polygalactomannans prepared by the method of the invention, such as cassia and guar, are modified by 2,3-epoxypropyl-trimethylammoniumchloride or 3-chloro-2-hydroxypropyl-trimethylammonium chloride. Typically, the average degree of substitution for such cationically modified polygalactomannans ranges from about 0.1 to 2 in one embodiment, and from about 0.5 to about 1.5 in another embodiment. In a further embodiment, the degree of substitution ranges from about 0.6 to about 1.

A specific embodiment of this invention relates to semi-refined cassia and guar gums which are highly purified polygalactomannans obtained by successively extracting the minced split material with a water/solvent mixture. In sharp contrast to the seed and split raw material, they are basically free of undesired low molecular weight molecules such as sennosides, anthraquinone derivatives and fibrous materials. Referring to cassia, the split raw material has a bright yellow color and the semi-refined cassia gum is off-white to slightly beige in color. Colloidal solutions of semi-refined guar and cassia products are colorless. These products are superior to traditionally milled guar and cassia gums in terms of viscosity and heat stability properties. In addition, semi-refined cassia has exhibited synergistic effects with anionic polymers.

Cationic cassia is a white to off-white powder. The product forms colloidal solutions in cold water. A typical product with a degree of substitution of about 1 shows a 1% viscosity of about 400 mPas with a haze value of below 10.

A still further aspect the present invention pertains to a method of purifying galactomannan hydrocolloids comprising the steps of:

(i) swelling at least one split of the group consisting of fenugreek, cassia, locust bean, tara or guar with water to form a swollen split, optionally followed by dispersing the swollen split in a water/organic solvent mixture, and (ii) at least one step of wet-mincing the product obtained under (i);

(iii) introducing the minced and swollen split into a mixture of water and an organic solvent while stirring; and (iv) separating the water/organic solvent mixture from the minced split composition to obtain a galactomannan hydrocolloid.

In accordance with this aspect of the Invention, undesired contaminants of the galactomannans such as fats, protein, ashes, fibers and anthraquinones can effectively be removed.

In another aspect, this method reduces the level of anthraquinones, in particular 1,8-hydroxy anthraquinones, such as physcion, aloe-emodin, rhein and chrysophanol, in grains. This aspect of the invention is carried out by the method described above for the preparation of the galactomannan hydrocolloids (steps (i) to (iv) and optional steps.) In a further embodiment, the present invention is directed to a method of reducing the level of said anthraquinones in cassia hydrocolloid from cassia endosperm flour, for instance, from cassia tora and cassia obtusifolia.

Accordingly, a particular embodiment of the invention is directed to a method for the purification of cassia which method comprises:

(i) swelling at least one split of cassia with water;
(ii) at least one step of wet-mincing the swollen split;
(iii) introducing the minced and swollen split into a mixture of water and an organic solvent while stirring; and
(iv) separating the water/organic solvent mixture from the swollen split composition to obtain cassia hydrocolloid.

According to the method disclosed in U.S. Pat. No. 4,840, 811, the powderous endosperm flour (the cassia flour) is extracted using a mixture of water and organic solvent. The particles are mainly purified only on the surface. Although according to the method of the U.S. '811 higher amounts of water improve the washing effect, the slow swelling of the powder results in significant problems during filtration. Furthermore, due to the penetration of humidity into the core of particles undesired compounds to accumulate in the particle core. According to the method of the '811 patent the increased amount of water does not appear to dissolve the compounds that need to be extracted and removed from the endosperm.

The deficiencies of the prior art processes have been overcome by the method of the present invention which comprises, as an essential step, the step of (pre) swelling the endosperm in water. Obviously, a certain amount of water in the crude endosperm flour particles has to be adjusted in order to dissolve undesired compounds, such as, for instance, the anthraquinones mentioned above. The endosperm splits only swell in water but do not swell in organic solvents such as alkanols or ketones (acetone). If an organic solvent is added to the swollen splits, the size of the split particles decreases. In order to facilitate separation, it is advantageous that the particles shrink again. Due to the addition of adequate portions of the organic solvent the hydrocolloid particles start to shrink. By the addition of the organic solvents in an increasing amount relative to the swollen particles, compounds which are not desirable in the galactomannan hydrocolloids, such as, for instance, fats, proteins, fibers, ashes and phytochemicals are removed from the hydrocolloids together with the water. Increasing the ratio of organic solvent to water facilitates the removal of water and undesirable compounds from the galactomannan hydrocolloid. The galactomannan hydrocolloid obtainable by the method of the invention is decolorized, odorless and tasteless. Most importantly, however, the undesired compounds, such as anthraquinones, are substantially absent from the obtained cassia hydrocolloid. In terms of the present invention by "substantially absent", it is meant that the total amount of anthraquinones such as physcion, chrysophanol, emodine, aloe-emodin and rhein in the cassia hydrocolloid is, with increased preference in the order given, below about 10 ppm or less in one aspect, less than 2 ppm in another aspect, less than 1 ppm in a further aspect and less than 0.7 ppm in a still further aspect based on the cassia hydrocolloid dry solid. The presence of and the amount of the anthraquinones in hydrocolloids can be determined by conventional analytical methods such as HPLC or GC/MS. For details, it is referred to S. O. Mueller, et al., in Food and Chemical Toxicology, 37 (1999), pages 481 to 491, the disclosure of which is incorporated herein by reference.

Most importantly, however, the method according to the present invention leads to galactomannan hydrocolloids which possess, in addition to being of high purity, improved properties in terms of viscosity, and gelation, such as gel strength and break strength, and heat stability compared to galactomannans which have been prepared in the traditional manner.

The above-mentioned properties of the hydrocolloids and, in particular in case of *cassia*, the significantly reduced level or even substantially absence of phytochemicals such as anthraquinones, make the hydrocolloids of the present invention particularly suitable as gelling and thickening agents for aqueous systems, for instance, in the field of food, fodder, cosmetic and pharmaceutical compositions. Typical aqueous systems are, for instance, emulsions, such as water-in-oil or oil-in water emulsions, or aqueous dispersions. Gelling and thickening agents are understood to be substances that are added to water or aqueous processing fluids, or to solid or liquid food, fodder or pharmaceuticals, for example, during the production and processing stage, in order to achieve a desired consistency or viscosity. In the field of food in particular, the hydrocolloids of the present invention obtained from the respective endosperm is characterized by its gelatinizing interaction with other hydrocolloids, by a high degree of efficiency and by the particularly low concentration needed.

A still further aspect this invention provides galactomannan hydrocolloids having a tailored performance profile, i.e., predictable performance properties such as a predetermined viscosity, gel strength and break strength, or any combination of these properties. This aspect of the invention is addressed by co-processing two or more different splits. By "co-processing", it is meant that at least two different swollen splits are combined and are co-minced, i.e., kneaded and homogenized by the process described above. In the first step of the method of this embodiment, the different splits can be swollen together or separately. Whether the splits are swollen together or separately depends on the swelling rate of the individual split. If the swelling rates of the individual splits are similar, it is advantageous to swell them together. In the case where the swelling rates of two different splits are dissimilar, the splits will be swollen separately. For instance, it is possible by co-processing *cassia* with guar to design a final hydrocolloid that has properties which are in between those typically related to the individual hydrocolloid of *cassia* and guar. Likewise, it is possible, due to the improved properties of a co-processed *cassia*/guar to simulate the properties or locust bean and/or tara hydrocolloids. This is advantageous because the market price of both tara and locust bean gum is much higher compared to the cassias and guar. In particular, this aspect is provided for by carrying out the above-described method for making the individual hydrocolloid in the presence of two different endosperms, i.e., a mixture of two different endosperms selected from fenugreek, *cassia*, locust bean, tara and guar. The (dry) weight ratio of the endosperms can generally be selected to be between about 95:5 to about 5:95, preferably between about 80:20 and about 20:80 depending on the desired properties of the final hydrocolloid blend. The co-processed galactomannans have a significantly higher (cold and hot) viscosity compared to mixtures of the individual galactomannans having the same quantitative composition (see FIG. 1). This results in the effect that the galactomannans locust bean gum ("LBG") and tara gum can be replaced by co-processed *cassia*/guar systems according to the invention.

The hydrocolloids of the invention efficiently thicken water, i.e., they increase the viscosity of water considerably if added in small amounts. The thickened aqueous compositions thus formed typically comprise about 0.1% to about 10% by weight in one aspect, about 0.2% to about 7% by weight in another aspect, about 0.2% to about 5% by weight In a further aspect, based on the composition comprising the inventive galactomannan hydrocolloid(s) and water.

Galactomannans of the present invention can be co-minced with polysaccharides derived from various natural and synthetic sources to significantly improve thickening and gelling efficiencies. In this case, the galactomannans of the present invention act as gelling agents or promoters. The co-processing of one or more of the galactomannans of the present invention with one or more polysaccharides obtained from tree and shrub exudates, such as gum arabic, gum gahatti, and gum tragacanth, as well as pectin; seaweed extracts, such as alginates and carrageenans; algae extracts, such as agar; microbiological polysaccharides, such as xanthan, gellan, and wellan; cellulose ethers, such as ethylhexylethylcellulose (EHEC), hydroxybutylmethylcellulose (HBMC), hydroxyethylmethylcellulose (HEMC), hydroxypropylmethylcellulose (HPMC), methyl cellulose (MC), carboxymethylcellulose (CMC), hydroxyethylcellulose (HEC), and hydroxypropylcellulose (HPC); starches, such as corn starch, tapioca starch, rice starch, wheat starch, potato starch and sorghum starch yield compositions with improved properties.

Generally, the compositions comprise the galactomannan hydrocolloid(s) and the above mentioned polysaccharides in a weight ratio of between about 10 to 90 weight percent and about 90 to 10 in one aspect, between about 20 to 80 in another aspect, and about 80 to 20 in a further aspect. For the individual galactomannan hydrocolloids optimum gels may be achieved if the ratio of *cassia* hydrocolloid to the above polysaccharides is between about 80 to 20 and about 50 to 50 in one aspect, between about 70 to 30 and about 55 to 45 in another aspect; the ratio of locust bean gum hydrocolloid and the above polysaccharide is between about 10 to 90 and about 40 to 60 in one aspect, between about 15 to 85 and about 30 to 70 in another aspect. The ratio of the guar hydrocolloid to the above polysaccharides is as above generally specified.

In one embodiment of the invention, compositions comprising a hydrocolloid selected from a *cassia* hydrocolloid, a locust bean gum hydrocolloid and tara hydrocolloid in combination with cellulose and its derivatives, carrageenan, or xanthan in the ratios as specified above. The galactomannan hydrocolloid may be derivatized as describe above.

The compositions may form gels if added to water. The aqueous gels formed typically comprise about 0.1% to about 10% by weight in one aspect, about 0.2% to about 7% by weight in another aspect, about 0.2% to about 5% by weight, based on the composition comprising the inventive galactomannans and the above polysaccharides, based on the total weight of hydrocolloid, polysaccharide and water.

Gels with particular advantageous properties in terms of gel strength, break strength and heat stability, syneresis and gel-setting temperature are obtainable by co-processing at least one split of the group consisting of fenugreek, *cassia*, locust bean, tara or guar with at least one polysaccharide selected mentioned above by the method for making galactomannan hydrocolloids comprising steps (i) and (ii) and optionally steps (iii) and (iv) specified above. When co-processing a split together with a gelling polysaccharide the weight ratio of the split to the polysaccharide generally is between about 95:5 and about 5:95 in one aspect, and between about 80:20 and about 20:80 in a further aspect of the invention.

The gels of the present invention are of significant commercial interest in the field of food, fodder, pharmaceuticals and cosmetics. The galactomannan hydrocolloids obtained according to the method of the present invention are particularly useful in the pharmaceutical field, such as in the galenic field for making controlled release agents and capsules. They can further be used for home care and personal care ("PC") products, such as cosmetics in ointments, emulsions, creams and as thickener for toothpastes. A further field of application for the hydrocolloids of the present invention is air-freshening compositions in which the hydrocolloids/gels form the perfume containing matrix.

Thus, the present invention also pertains to food, fodder, pharmaceutical, cosmetic, textile, industrial and home and personal care compositions comprising the galactomannan hydrocolloids of this invention.

Generally, the hydrocolloids or hydrocolloid co-gums of the present invention may be used as stabilizer, texturizer, soluble fiber source, emulsifier, carrier, controlled active release for flavors and drugs, and as a water retention agent either as a single hydrocolloid or in combination with other hydrocolloids in various food applications as specified in the FDA Food Categories, Code of Federal Regulations 21 C.F.R. §170.3, which is incorporated herein by reference.

Semi-refined *cassia* gum was found to be superior to the related galactomannans locust bean gum, tara gum and guar gum in terms of gelling performance by utilizing synergistic effects with anionic hydrocolloids. Co-gums of *cassia* gum and guar gum of the present invention may be a replacement of any usage of locust bean gum or tara gum by covering the whole area of about 2:1 galactomannans through about 5:1 galactomannans.

As an example for new food applications, blends or co-gums of *cassia* gum with carrageenan or other hydrocolloids have been tested at the German Institute of Meat Technology in meat products and sausages. It was found that they have the potential to replace phosphates. Independently, the meat content could be reduced by about 20 wt. % without loss of taste and mouth feel. This is of special interest in view of the osteoporosis risk through intake of phosphates and the production of low-calorie products.

Further examples are initial tests of semi-refined *cassia* gum of the present invention in ice cream applications. It was found that *cassia* gum of this invention is superior to LBG. In replacing LBG, the resulting ice cream provides higher volume and improves mouth feel and taste.

Some embodiments of the invention relate to the use of the polygalactomannan hydrocolloids as multi-functional polymer ingredients in personal care, health care, household, institutional and industrial product applications and the like. The polygalactomannan hydrocolloids can be employed as emulsifiers, spreading aids and carriers for enhancing the efficacy, deposition and delivery of chemically and physiologically active ingredients and cosmetic materials, and as a vehicle for improving the psychosensory and aesthetic properties of a formulation in which they are included. The term "personal care products" as used herein Includes, without limitation, cosmetics, toiletries, cosmeceuticals, beauty aids, personal hygiene and cleansing products that are applied to the skin, hair, scalp, and nails of humans and animals. The term "health care products" as used herein includes, without limitation, pharmaceuticals, pharmacosmetics, oral care products (mouth, teeth), eye care products, ear care products and over-the-counter products and appliances, such as patches, plasters, dressings and the like. The term also includes medical devices that are externally applied to or into the body of humans and animals for ameliorating a health related or medical condition. The term "body" includes the keratinous (hair, nails) and non-keratinous skin areas of the entire body (face, trunk, limbs, hands and feet), the tissues of body openings and the eyes. The term "skin" includes the scalp and mucous membranes. The term "household care products" as used herein includes, without limitation, products being employed in a household for surface protection and/or cleaning including biocidal cleaning products for maintaining sanitary conditions in the kitchen and bathroom and laundry products for fabric cleaning and the like. The term "institutional and industrial products" as used herein includes, without limitation, products employed for protection and/or cleaning or maintaining sanitary conditions in industrial and institutional environments, including hospitals and health care facilities, and the like.

In a given composition or application, the polygalactomannan hydrocolloids of this invention can, but need not, serve more than one function, such as a thickener and conditioner, film former and carrier or deposition aid, and the like. The amount of polygalactomannan hydrocolloids that can be employed depends upon the purpose for which they are included in the formulation and can be determined by person skilled in the formulation arts. Thus, as long as the physicochemical and functional properties are achieved, a useful amount of polygalactomannan hydrocolloids on a total composition weight basis, typically can vary in the range of about 0.01% to about 25%, but is not limited thereto.

Compositions containing polygalactomannan hydrocolloids can be packaged and dispensed from containers such as jars, tubes, sprays, wipes, roll-ons, sticks and the like, without limitation. There is no limitation as to the form of the product in which these derivatives can be incorporated, so long as the purpose for which the product is used is achieved. For example, personal and health care products containing polygalactomannan hydrocolloids can be applied to the skin, hair, scalp, and nails, or to hard surfaces or laundry fabrics, without limitation in the form of gels, sprays (liquid or foams), emulsions (creams, lotions, pastes), liquids (rinses, shampoos), bars, ointments, suppositories, and the like.

The polygalactomannan hydrocolloids of this invention are suitable for preparation of personal care (cosmetics, toiletries, cosmeceuticals) and topical health care products, including, without limitation, hair care products (shampoos, combination shampoos, such as "two-in-one" conditioning shampoos), post-shampoo rinses, setting and style maintenance agents (including setting aids, such as gels and sprays, grooming aids such as pomades, conditioners, perms, relaxers, hair smoothing products, and the like), skin care products (facial, body, hands, scalp and feet), such as creams, lotions and cleansing products, antiacne products, antiaging products (exfoliant, keratolytic, anticellulite, antiwrinkle, and the like), skin protectants (sun care products, such as sunscreens, sunblock, barrier creams, oils, silicones and the like), skin color products (whiteners, lighteners, sunless tanning accelerators and the like), hair colorants (hair dyes, hair color rinses, highlighters, bleaches and the like), pigmented skin colorants (face and body make-ups, foundation creams, mascara, rouge, lip products, and the like) bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softness, and the like).

Toiletries and health and beauty aids containing polygalactomannan hydrocolloids of the invention can include, without limitation, hair-removal products (shaving creams and lotions, epilators, after-shaving skin conditioner, and the like); deodorants and antiperspirants; oral care products (mouth, teeth, gums), such as mouth wash, dentifrice, such as toothpaste, tooth powder, tooth polishes, tooth whiteners, breath fresheners, denture adhesives, and the like; facial and body hair bleach and the like. Other health and beauty aids can contain the polygalactomannan hydrocolloids and derivatized polygalactomannan hydrocolloids of the invention and include, without limitation, sunless tanning applications containing artificial tanning accelerators, such as dihydroxyacetone (DHA), tyrosine, tyrosine esters and the like: skin depigmenting, whitening and lightening, formulations containing such active ingredients as kojic acid, hydroquinone, arbutin, fruit, vegetable or plant extracts, (lemon peel extract, chamomile, green tea, paper mulberry extract, and the like), ascorbyl acid derivatives ascorbyl palmitate, ascorbyl stearate, magnesium ascorbyl phosphate and the like); foot care products, such as keratolytic corn and callous removers, foot soaks, foot powders (medicated such as antifungal athlete's foot powder, ointments, sprays, and the like, antiperspirant powders, or non-medicated moisture absorbent powder), liquid foot sprays (non-medicated, such as cooling, and deodorants sprays, and the like), and foot and toenail conditioners (lotions, creams, nails softeners, and the like).

Topical health and beauty aids can include the polygalactomannan hydrocolloids of the invention as spreading aids and film formers include, without being limited thereto, skin protective sprays, cream, lotion, gels, stick, powder products such as insect repellants, itch relief, antiseptics, disinfectants, sun blocks, sun screens, skin tightening and toning milk and lotions, wart removal compositions, and the like.

The polygalactomannan hydrocolloids of the invention are particularly useful as suspending agents for particulates making them suitable for dermal products containing particulates, microabrasives, and abrasives, such as shower gels, masks and skin cleansers containing exfoliative scrubs agents. Typical particulates include, but are not limited thereto, shell, seed, and stone granules, such as almonds, apricot (seed, kernel powder, shell), avocado, coconut, corn cob, olive, peach, rose hip seed, walnut shell, and the like, aluminum silicate, jojoba (wax, seed powder), oyster shell powder, evening primrose seed, milled adzuki beans, and the like, polyethylene (granules, spheres), polyethylene (and) hydroxycellulose granules, microcrystalline cellulose, polystyrene, polystyrene (and) talc granules, ground pumice, ground loofah, ground seaweed, rice, oat bran, silica (hydrated, colloidal, and the like), ground eggshell, ground blue poppy seed, salt, such as sodium chloride, dead sea salt, and the like, and mixtures thereof.

The polygalactomannan hydrocolloids of the invention are useful as thickeners and film formers in a variety of dermatological, cosmeceutical compositions employed for topically ameliorating skin conditions caused by aging, drying, photodamage, acne, and the like, containing conditioners, moisturizers, antioxidants, exfoliants, keratolytic agents, vitamins, and the like. The polygalactomannan hydrocolloids of the invention can be employed as a thickener for active skin treatment lotions and creams, containing as such active ingredients, acidic anti-aging agents, anti-cellulite, and anti-acne agents, such as alpha-hydroxy acid (AHA), beta-hydroxy acid (BHA), alpha amino-acid, alpha-keto acids (AKAs), and mixtures thereof. In such cosmeceuticals, AHAs can include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, azelaic acid, acetic acid, alpha-lopioc acid, salicylic acid, AHA salts and derivatives, such as arginine glycolate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. BHAs can include, but are not limited to, 3-hydroxypropanoic acid, beta-hydroxybutyric acid, beta-phenyl lactic acid, beta-phenylpyruvic acid, and the like. Alpha-amino acids include, without being limited to, alpha-amino dicarboxylic acids, such as aspartic acid, glutamic acid, and mixtures thereof, sometimes employed in combination with fruit acids. AKAs include pyruvic acid. In some antiaging compositions, the acidic active agent may be retinoic acid, a halocarboxylic acid, such as trichloroacetic acid, an acidic antioxidant, such as ascorbic acid (vitamin C), a mineral acid, phytic acid, lysophosphatidic acid, and the like. Some antiacne agents, for example, can include salicylic acid, derivatives of salicylic acid, such as 5-octanoylsalicylic acid, retinoic acid and its derivatives.

Other health care products in which the polygalactomannan hydrocolloids of the invention can be included are medical products, such as topical and non-topical pharmaceuticals and devices. In the formulation of pharmaceuticals, a polygalactomannan hydrocolloids of the invention can be used as a thickener and/or lubricant in such products as binders, coatings, controlled release agents, creams, pomades, gels, pastes, ointments, tablets, gel capsules, purgative fluids (enemas, emetics, colonics, and the like), suppositories, antifungal foams, eye products (ophthalmic products such as eyedrops, artificial tears, glaucoma drug delivery drops, contact lens cleaner, and the like), ear products (wax softeners, wax removers, otitis drug delivery drops, and the like), nasal products (drops, ointments, sprays, and the like), wound care (liquid bandages, wound dressings, antibiotic creams, ointments and the like), without limitation thereto.

The polygalactomannan hydrocolloids of the invention can be used in home care, institutional and industrial applications (I&I), as a rheology modifier, fabric conditioning agent, especially to improve efficiency through "cling-on surface" or improving efficacy of disinfectants, and biocidal formulations, and to synergistically improve fabric softening efficacy in combination with traditional fabric softeners. Typical household and I&I products that may contain the polygalactomannan hydrocolloids of the invention, include, without limitation, laundry and fabric care products, such as detergents, fabric softeners (liquid or sheet), ironing sprays, dry cleaning aids, anti-wrinkle sprays, spot removers and the like; hard surface cleaners for the kitchen and bathroom and utilities and appliances employed or located herein, such as toilet bowl gel, tub and shower cleaners, hard water deposit removers, floor and tile cleansers, wall cleansers, floor and chrome fixture polishes, alkali-strippable vinyl floor cleaners, marble and ceramic cleaners, air freshener gels, liquid cleansers for dishes, and the like; disinfectant cleaners, such as toilet bowl and bidet cleaners, disinfectant hand soap, room deodorizers, and the like.

The polygalactomannan hydrocolloids of the invention can be used as rheology modifiers, dispersants, stabilizers, promoters, and the like, in industrial product applications, such as, without limitation, textiles processing, finishing, printing, and dyeing aids, protective washable surface coatings, manufacture of synthetic leather by saturation of non-woven fabrics, and the like, of woven or non-woven fabrics and natural or synthetic fibers); water treatment (waste water, cooling water, potable water purification, and the like): chemical spills containment (acid-spill absorbent, and the like); leather and hides (processing aids, finishing, embossing and the like); paper and papermaking (surface coating, such as pigmented coatings, antistatic coatings and the like, pulp binders, surface sizing, dry and wet strength enhancers, manufacture of synthetic fibers, such as non-woven fabrics, wet-laid felts, and the like): printing (inks, anti-wicking ink-jet printer inks, thickeners for ink formulations containing cationic dyes for printing acrylic fabrics, and the like); paints (pigments and grinding additives, crosslinking agents for epoxy latex emulsions, particulate-suspending aids for clays, pigments and the like); industrial plant effluent treatment (flocculants for phenolics in paper mill effluent, and the like); metal working (acid etch cleaners, low pH metal coatings, pickling agents in cold rolled steel processing, and the like); wood preservation: and industrial construction products for buildings and roads (cement plasticizers, asphalt emulsions stabilizers at low pH, acid etch for cement, consistency modifiers of concrete, mortar, putty and the like). The polygalactomannan hydrocolloids of the invention are also useful as thickeners for rust removers, acid truck cleaners, scale removers, and the like, and as dispersion stabilizers of products containing particulates, such as clay, pigments (titanium dioxide, calcium carbonate, and other minerals), abrasives, and the like, employed in a variety of foregoing industrial applications and in drilling muds and oil well fracturing fluids.

The foregoing products typically contain various conventional additives and adjuvants known in the art, some of which can serve more than one function. The amounts employed will vary with the purpose and character of the product and can be readily determined by one skilled in the formulation arts and from the literature.

It is known that formulated compositions for personal care and topical, dermatological, health care, which are applied to the skin and mucous membranes for cleansing or soothing, are compounded with many of the same or similar physiologically tolerable ingredients and formulated in the same or similar product forms, differing primarily in the purity grade of ingredients selected, by the presence of medicaments or pharmaceutically accepted compounds, and by the controlled conditions under which products may be manufactured. Likewise, many of the ingredients employed in the products for household and I&I are same or similar to the foregoing, differing primarily in the amounts and material grades employed. It is also known that the selection and permitted amount of ingredients also may subject to governmental regulations, on a national, regional, local, and international level. Thus, discussions herein of various useful ingredients for personal care and health care products may apply to household and I&I products and Industrial applications.

The choice and amount of ingredients in formulated compositions containing the polygalactomannan hydrocolloids of the invention will vary depending on the product and its function, as is well known to those skilled in the art. Formulation ingredients for personal care and topical health care products can typically include, but are not limited to, solvents, surfactants (as cleansing agents, emulsifying agents, foam boosters, hydrotropes, solubilizing agents, and suspending agents), non-surfactant suspending agents, emulsifiers, skin conditioning agents (emollients, moisturizers, and the like), hair conditioning agents, hair fixatives, film-formers, skin protectants, binders, chelating agents, antimicrobial agents, antifungal agents, antidandruff agents, abrasives, adhesives, absorbents, colorants, deodorants agents, antiperspirant agents, humectants, opacifying and pearlescing agents, antioxidants, preservatives, propellants, spreading agents, sunscreen agents, sunless skin tanning accelerators, ultraviolet light absorbers, pH adjusting agents, botanicals, hair colorants, oxidizing agents, reducing agents, skin bleaching agents, pigments, physiologically active agents, anti-inflammatory agents, topical anesthetics, fragrance and fragrance solubilizers, and the like, in addition to ingredients previously described that may not appear herein. Oral care products, for instance, can contain anticaries, antitartar and/or antiplaque agents in addition to surfactants, abrasives, humectants and flavorants. An extensive listing of substances and their conventional functions and product categories appears in the CFTA Dictionary, generally, and in Vol. 2, Section 4 and 5, in particular.

Due to its water swelling properties, the polygalactomannan hydrocolloids of the invention are often used as a gelling agent for water-based systems. For instance, the polygalactomannan hydrocolloids of the invention can be used as gelling agents for air treatment gels that are designed to release continuously volatile air treatment agents from the gel. The volatile air treatment components can include air freshening ingredients such as disinfectants, bactericides, insecticides, fungicides, deodorants, pest repellants, odoriferous materials and mixtures thereof. Odoriferous materials include oil of rose, oil of lime, oil of lemon, oil of spearmint, oil of wintergreen, oil of cedar wood, oil of fir Canadian, and the like. These oils may be used in combination with fragrances such as aromatic esters, aldehydes, ketones, and other compounds known to those skilled in the art of blending fragrances. The level of the gelling agent ranges from about 0.5 to about 25 wt. % in one embodiment, from about 0.75 to about 15 wt. % in another embodiment, and from about 1 to 5 wt. % in a further embodiment, wherein the weight percents are based on the total weight of the composition.

The polygalactomannan hydrocolloids of the invention can also be used to form hydrocolloid gels for wound dressing and medical devices. The healing of wounds such as wounds resulting from injury, surgery etc. is greatly dependent upon the dressing used. Conventional bandages often do not provide optimum results. Special pressure relieving or reducing measures should also be taken. A moist dressing is also often beneficial, providing rehydration of dehydrated tissue, increased angiogenesis (proliferation of new blood vessels), minimal bacterial growth, physical protection, and the maintenance of the proper pH for stimulating the release of oxygen and for allowing proteolytic enzymes to work more efficiently.

Pourable water based natural or synthetic water-soluble or water swellable gel forming hydrocolloidal gels can be used for wound dressing. They are initially sufficiently fluid to be poured or spread onto the wound, but, which after application can form a moist solid elastic protective gel that remains in the polymeric hydrocolloid hydrated state.

Medical devices adapted for implanting into the body to facilitate the flow of bodily fluids, to serve as vascular grafts or for other purposes have been developed. Typically, these devices include stents, catheters, or cannulas, plugs, constrictors, tissue or biological encapsulants and the like. Many of these devices that are used as implants are made from durable, non-degradable plastic materials such as polyurethanes, polyacrylates, and silicone polymers, and the like. In some instances, they are made from biodegradable polymers, which remain stable in-vivo for a period of time, but eventually biodegrade into small molecules that are easily excreted form the body. Crosslinked hydrogels made from the polygalactomannan hydrocolloids of the invention are contemplated for use for such medical devices. They offer excellent biocompatibility and have been shown to reduce tendency for inducing thrombosis, encrustation and inflammation. In these applications, the hydrocolloidal polymeric gel can be used for wound healing or implant applications. The polygalactomannan hydrocolloids of the invention, mixed with water, will form a solid temperature irreversible elastic gel, i.e., flexible gel, with or without crosslinking agents, to assist in the formation of a non-fluid system. Typical gels contain from 3 to 15 wt. % polygalactomannan hydrocolloids of the invention. Greater amount of polymer and crosslinking agents will provide a more solid gel, or a gel that will display better physical and mechanical properties (modulus, stress at yield, strength). Sufficient water should be present to provide the initial fluidity required for pouring or spreading the gel onto the wound, or inserting the gel in the body through an endoscope, in the case of implants. Ionic and non-ionic crosslinkers are used then to solidify the gel, and control the crosslinking density (i.e., the final mechanical and physical properties of the gel). For most applications, the crosslinking agents are present from 0 to 8 wt. %, more preferably from 0.1 to 5 wt. %. Any suitable non-toxic crosslinkers can be used, including galactose, mannose, oligosaccharides containing either or both mannose and galactose, borax, organic titanate, boric acid, diepoxides, polycarboxylic acids, glutaraldehyde, dihydroxyaluminum, sodium carbonate, citric acid, and a soluble source of any of the cations of calcium, magnesium and aluminum. In the case of implants, the ionic crosslinks can be easily and selectively displaced in-vivo after implantation of the implant device in the body, resulting in a swelling and softening of the device in the body which enhances patient comfort. The device will retain its original configuration without disintegration.

If desired, any of the following substances can be included in the composition: medication and disinfectants, wound healing enhancers such as vitamins, blood coagulants, antibiotics, source of oxygen, etc.

Cationic polymers are often used as conditioners in skin and/or hair compositions. Quaternized polymers are used in shampoos and conditioners to facilitate compatibility. The positively charged nitrogen bonds with negatively charged hair fibers to form films. They also make the hair feel softer and smoother to the touch without creating too much build-up. The polygalactomannan hydrocolloids of the invention can be used as part of a cationic polymer conditioner package in a conditioning detergent formulation that not only imparts cleansing, wet detangling, dry detangling and manageability properties to the hair, but also is relatively non-irritating. This composition is thus suitable for use by young children and adults having sensitive skin and eyes. In one embodiment of the invention, cationic *cassia* and cationic guar derivatives are very efficient in these applications.

In skin care formulations, the polygalactomannan hydrocolloids of the invention can be used as polymeric skin feel and skin mildness aids in ultra-mild skin cleansing compositions or moisturizing compositions. The polygalactomannan hydrocolloids of the invention provide skin conditioning, skin mildness and moisturizing, while maintaining desirable lathering properties. The polygalactomannan hydrocolloids of the invention also display a desirable silky, soft smooth in-use feeling, by avoiding less skin irritation though excessive defatting or overdrying the skin after multiple usage. In particular, the positively charged cationic polygalactomannans, such as the cationic *cassia* derivatives can bind with negatively charged sites on the skin to provide a soft skin feel after use. It improves the sensory feel on skin by reducing tackiness and greasiness and improving smoothness.

The polygalactomannan hydrocolloids of the invention can be employed as a rheology modifier or emulsion stabilizing agent in emulsions. The polygalactomannan hydrocolloids of the invention provide foaming emulsion compositions with better emulsion stability. The need to combine the aspects of cleansing and skin care with one another in a dermatologically compatible composition is growing. In particular, the use of alkyl oligoglycosides as non-ionic surfactants is advantageous due to their favorable foaming and cleaning properties, biodegradability and advantageous dermatological compatibility. But such alkyl oligoglycoside containing emulsions lack cosmetic elegance. The gels are not readily absorbed by the skin. Instead of forming a creamy microfoam, they only form a coarse macrofoam. Formulations containing cationic the galactomannan hydrocolloids of the invention such as the cationic *cassia* and guar derivatives lead to the formation of a rich and creamy microfoam that is readily absorbed by the skin with high cleaning and refatting properties.

Cleansing compositions that show good conditioning and lathering properties are highly desirable. This is difficult to achieve due to the inherent incompatibility between anionic surfactants (that show superior cleansing with high lathering compared to other surfactant) and the cationic polymers (that provides conditioning or bring therapeutic agents to the skin or hair). The presence of those surfactants in the cleansing composition also interferes with the deposit of therapeutic agents, since the detergents are designed to remove oil, grease and dirt and particulate matter from the hair, scalp and skin during rinsing. In personal care applications, the polygalactomannan hydrocolloids of the invention can be used along with surfactant, water-soluble agents (for instance silicones) to provide an enhanced delivery system for therapeutic agents, conditioners, moisturizers, etc. Examples of therapeutic agents include, but are not limited to, detangling/wet combing agent, humectants, anti-acne agents, anti hair loss agents, hair-growth inhibitor agents, herbal extracts, etc.

Various water-insoluble particulates, solids substance or liquid particles of an oil emulsions, have been incorporated in detergent products for the purpose of imparting some residual properties or characteristics on surfaces washed with the products. For instance, shampoo composition contains particulate antidandruff agents, which function by deposition and retention on the hair and scalp. Various water-insoluble particulates (solid or liquid particles of oil emulsions) have been incorporated in detergent compositions for the purpose of imparting desirable residual properties on surfaces washed with such products. For instance, shampoo compositions containing particulate antidandruff agents can not function unless such agents are deposited and retained on the hair and scalp subsequent to rinsing. Particulate antimicrobial agents have also been used in various laundry detergents and personal care body washes to impart residual antimicrobial activity to fabrics and hair and skin surfaces. Various other water-insoluble or sparingly soluble particulate materials such as sunscreen agents, fabric softeners, fabric brighteners, fabric whiteners, etc., have also been employed in detergent compositions. Their activity depends on particle deposition and retention on washed substrates (skin, hair, fabrics, etc.). By its very nature, an effective detergent composition tends to minimize retention of particulate matter on washed surfaces. Consequently, only a relatively small portion of the active agents present in detergent compositions is actually retained after washing and rinsing of the substrate surface. Since the activity of the active agent depends on the quantity of the particles deposited and retained on the surface, a means to enhance active agent deposition and retention are highly desirable.

In styling shampoo, the use of the cationic *cassia* derivatives of the present invention as deposition aids to enhance the deposition of water-insoluble styling polymers improves the styling performance (conditioning, curl retention, superior hair feel) of the hair. The cationic *cassia* derivatives of the invention can be used as deposition aids in combination with water-insoluble hair styling polymers selected from the group of (meth)acrylates copolymers and silicone-grafted (meth) acrylates. Examples include t-butylacrylate/2-ethylhexylacrylate copolymers, t-butylacrylate/2-ethylhexylmethacrylate copolymers, t-butyl acrylate/2-ethylhexyl methacrylate/ polydimethylsiloxane macromer, and t-butyl methacrylate/2-ethylhexylmethacrylate/polydimethylsiloxane macromer copolymers, and mixtures thereof.

As previously discussed, various water-insoluble or sparingly soluble particulate materials such as sunscreens, fabric softeners, fabric brighteners, fabric whiteners, biocides, etc. are employed in cleaning compositions. Their activity will depend on the particle deposition and retention on washed systems. By its very nature, an effective detergent composition tends to minimize retention of particulate matters on washed surfaces. Thus, only a relatively small portion of the agents present in such detergent composition is actually retained after washing and rinsing of the surface. Since the activity of the functional agent depends on the quantity of the particles deposited and retained on the surface, means to enhance deposition are highly desirable. Cationic *cassia* and guar derivatives can be used as a deposition aid for those particulate materials, for instance, for depositing fabric softener on fabric surfaces during laundering process, or depositing biocides on hard surfaces during sanitization. For example, the use of cationic *cassia* and guar derivatives along with regular laundry detergents ingredients such as surfactants, builders, etc., shows improvement in softening properties due to better deposition of the fabric softener on the surface and significantly more storage stability. From about 0.05 to about 5 wt. % of the overall composition is used for the cationic *cassia* and guar derivatives as deposition aid.

The polygalactomannan hydrocolloids and modified derivatives thereof of the invention can also be used as a soil release agent in laundry detergent composition. During the laundering operation, these polymers absorb onto the surface of the fabric immersed in the wash solution. The absorbed polymer forms a hydrophilic layer which remains on the fabric after it is removed from the wash solution and dried, thereby imparting soil release properties to the laundering fabric. Low levels of cationic *cassia* derivatives (0.3 to 5 wt. %) in combination with typical fabric softeners can provide the soil release properties without adversely affecting the whiteness of fabric upon repeated usage.

Detergents, Shampoos and Body Washes

As previously discussed the hydrocolloid and co-processed hydrocolloid/polysaccharide compositions of the present invention are useful personal care compositions. Exemplary personal care compositions are shampoos and body washes. Exemplary detergent compositions include dishwashing detergents, laundry detergents and Industrial cleaners. In such formulations, the amount of the nonionic and cationic derivatized polygalactomannans to be included is between about 0.1 and about 2.0 percent by weight of the formulation in one aspect of the invention. In another aspect, the amount can range between about 0.3 and about 1.5 percent by weight, and in still another aspect between about 0.5 and about 1.0 percent by weight.

In detergent compositions, the formulations used can typically include one or more surfactants in an aqueous carrier. The surfactants selected for use in producing such formulations are considered within the skill of the artisan and can be selected from nonionic, anionic, cationic, amphoteric and zwitterionic surfactants known in the art. Mixtures of the above surfactants may also be selected. Examples of nonionic surfactants which may be selected include fatty acid amides, alkoxylated fatty alcohol amines, fatty acid esters, glycerol esters, alkoxylated fatty acid esters, sorbitan esters, alkoxylated sorbitan esters, alkylphenol alkoxylates, aromatic alkoxylates and alcohol alkoxylates.

The shampoo compositions can comprise, consist of, or consist essentially of the elements and components of the invention described herein, as well any of the additional or optional ingredients, components, described herein or known in the art.

All percentages, parts and ratios are based upon the total weight of the shampoo compositions of the present invention, unless otherwise specified. All such weights as they pertain to listed ingredients are based on the active level and, therefore, do not include carriers or by-products that may be included in commercially available materials, unless otherwise specified.

Shampoo compositions according to the invention can comprise one or more cleansing surfactants and emulsifying surfactants which are cosmetically acceptable and suitable for topical application to the hair. In one aspect of the invention, the shampoo compositions comprise at least one additional surfactant (in addition to that used as emulsifying agent) to provide a cleansing benefit. Suitable cleansing surfactants, which may be used singularly or in combination, are selected from anionic, amphoteric and zwitterionic surfactants, cationic surfactants, and mixtures thereof. The cleansing surfactant may be the same surfactant as the emulsifier, or may be different. Preferred cleansing surfactants are selected from anionic, amphoteric and zwitterionic surfactants, and mixtures thereof. The shampoo compositions of the present invention, are described in detail herein.

The shampoo compositions of the present invention comprise an anionic detersive surfactant component to provide cleaning performance to the composition. The anionic detersive surfactant component in turn comprises anionic detersive surfactant, zwitterionic or amphoteric detersive surfactant which has an attached group that is anionic at the pH of the composition, or a combination thereof, preferably anionic detersive surfactant. Such surfactants should be physically and chemically compatible with the essential components described herein, or should not otherwise unduly impair product stability, aesthetics or performance. Suitable anionic detersive surfactant components for use in the shampoo composition herein include those which are known for use in hair care or other personal care cleansing compositions. The concentration of the anionic surfactant component in the shampoo composition should be sufficient to provide the desired cleaning and lather performance, and generally can range from about 5% to about 50% in one aspect, from about 8% to about 30% in another aspect, from about 10% to about 25% in a further aspect, and from about 12% to about 18% in a still further aspect, by weight of the composition.

Exemplary anionic surfactants suitable for use in the shampoo compositions are the alkyl and alkyl ether sulfates. These materials have the respective formulae $R^8OSO_3M$ and $R^8O(C_2H_4O)_xSO_3M$, wherein $R^8$ is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. The cation M should be selected such that the anionic detersive surfactant component is water soluble. Solubility of the surfactant will depend upon the particular anionic detersive surfactants and cations chosen. In one aspect, $R^8$ has from about 8 to about 18 carbon atoms, in another aspect from about 10 to about 16 carbon atoms, and in a further aspect from about 12 to about 14 carbon atoms. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene, oxide per mole of alcohol, is sulfated and neutralized.

Specific non-limiting examples of alkyl ether sulfates which may be used in the shampoo compositions of the present invention include sodium and ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic detersive surfactants are the water-soluble salts of organic, sulfuric acid reaction products conforming to the formula $R^9SO_3M$ where $R^9$ is a straight or branched chain, saturated, aliphatic hydrocarbon radical having from about 8 to about 24 in one aspect, and in another aspect from about 10 to about 18 carbon atoms. M is a cation as described previously. Non-limiting examples of such detersive surfactants are the salts of an organic sulfuric acid reaction product of a hydrocarbon of the methane series, including iso-, neo-, and n-pus, having from about 8 to about 24 carbon atoms, preferably about 12 to about 18 carbon atoms, and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278, which descriptions are incorporated herein by reference.

Other anionic detersive surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid. Other suitable anionic detersive surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms in one aspect, and from about 12 to about 16 carbon atoms in another aspect. In a still further aspect they are straight chain olefins. In addition to the true alkene sulfonates and a proportion of hydroxy-alkanesulfonates, the olefin sulfonates can contain minor amounts of other materials, such as alkene disulfonates depending the reaction conditions, proportion of reactants, the nature of the starting olefins and impurities in the olefin stock and side reactions during the sulfonation process. A non-limiting example of such an alpha-olefin sulfonate mixture is described in U.S. Pat. No. 3,332,880, which description is incorporated herein by reference.

Another class of anionic detersive surfactants suitable for use in the shampoo compositions are the beta-alkyloxy alkane sulfonates. These surfactants conform to the formula:

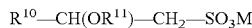
$$R^{10}\text{—CH}(OR^{11})\text{—CH}_2\text{—SO}_3M$$

where $R^{10}$ is a straight chain alkyl group having from about 6 to about 20 carbon atoms, $R^{11}$ is a lower alkyl group having from about 1 to about 3 carbon atoms, and M is a water-soluble cation as described hereinbefore. In one embodiment, the anionic detersive surfactants for use in the shampoo compositions include ammonium lauryl sulfate, ammonium laureth sulfate, triethylamine lauryl sulfate, triethyine laureth sulfate, triethanolamine lauryl sulfate, triethanolamine laureth sulfate, monoethanomaine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauryl sarcosinate, lauryl sarcosine, cocoyl sarcosine, ammonium cocoyl sulfate, ammonium lauryl sulfate, sodium cocoyl sulfate, sodium lauryl sulfate, potassium cocoyl sulfate, potassium lauryl sulfate, triethanolamine lauryl sulfate, triethanolamine lauryl sulfate, monoethanolamine cocoyl sulfate, monoethanolamine lauryl suite, sodium tridecyl benzene sulfonate, sodium dodecyl benzene sulfonate, and combinations thereof.

Suitable amphoteric or zwitterionic detersive surfactants for use in the shampoo composition herein include those which are known for use in hair care or other personal care cleansing composition, and which contain a group that is anionic at the pH of the shampoo composition. The concentration of such amphoteric detersive surfactants can range from about 0.5% to about 20% in one aspect, and from about 1% to about 10%, by weight of the composition in another aspect. Non-limiting examples of suitable zwitterionic or amphoteric surfactants are described in U.S. Pat. Nos. 5,104,646 and 5,106,609, which descriptions are incorporated herein by reference. Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate.

Zwitterionic detersive surfactants suitable for use in the shampoo composition are well known in the art and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred. The shampoo compositions of the present invention may further comprise additional surfactants for use in combination with the anionic detersive surfactant component described hereinbefore. Suitable optional surfactants include nonionic surfactants, cationic surfactants, and combinations thereof. Any such surfactant known in the art for use in hair or personal care products may be used, provided that the optional additional surfactant is also chemically and physically compatible with the essential components of the shampoo composition, or does not otherwise unduly impair product performance, aesthetics or stability. The concentration of the optional additional suits in the shampoo composition may vary with the cleansing or lather performance desired, the optional surfactant selected, the desired product concentration, the presence of other components in the composition, and other factors well known in the art. Non-limiting examples of other anionic, zwitterionic, amphoteric or optional additional surfactants suitable for use in the shampoo compositions are described in McCutcheonus. Emulsifiers and Detergents. 1989 Annual, published by M. C. Publishing Co., and U.S. Pat. Nos. 3,929,678, 2,658,072; 2,438,091; 2,528,378, which descriptions are incorporated herein by reference.

The shampoo composition can also include co-surfactants, to help impart aesthetic, physical or cleansing properties to the composition. A preferred example is a nonionic surfactant, which can be included in an amount ranging from 0% to about 5% by weight based on total weight. For example, representative nonionic surfactants that can be included in shampoo compositions of the invention include condensation products of aliphatic ($C_8$ to $C_{18}$) primary or secondary linear or branched chain alcohols or phenols with alkylene oxides, usually ethylene oxide and generally having from 6 to 30 ethylene oxide groups. Other representative nonionics include mono- or di-alkyl alkanolamides. Examples include coco mono- or di-ethanolamide and coco mono-isopropanolamide. Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Exemplary APGs are defined by the following formula $R^{12}(G)_n$ wherein $R^{12}$ is a branched or straight chain alkyl group which may be saturated or unsaturated and G is a saccharide group. $R^{12}$ can represent a mean alkyl chain length of from about $C_5$ to about $C_{20}$. In one aspect, $R^{12}$ represents a mean alkyl chain length of from about $C_8$ to about $C_{12}$. In another aspect, the value of $R^{12}$ lies between about 9.5 and about 10.5. G is selected from $C_5$ or $C_6$ monosaccharide residues, and is preferably a glucoside. Exemplary groups defined under G include glucose, xylose, lactose, fructose, mannose and derivatives thereof. The degree of polymerization, n, may have a value of from about 1 to about 10 or more. In one aspect, the value of n lies in the range of from about 1.1 to about 2. In another aspect, the value of n lies in the range of from about 1.3 to about 1.5. Suitable alkyl polyglycosides for use in the invention are commercially available and include, for example, those materials identified as Oramix NS10 from Seppic; Plantaren 1200 and Plantaren 2000 from Henkel.

The total amount of surfactant (including any co-surfactant, and/or any emulsifying agent) in shampoo compositions of the invention is generally from 0.1 to 50% by weight in one aspect, from 5 to 30% in another aspect, and from 10% to 25% by weight in a further aspect of the total shampoo composition.

The shampoo compositions of the present invention can comprise a silicone hair conditioning agent, in combination with an optional suspending agent for the silicone. The silicone hair conditioning agent can be selected from non volatile silicones, volatile silicones water soluble silicones, and combinations thereof. The silicone conditioning agent is present in the shampoo composition at concentrations ranging from about 0.01% to about 10% by weight of the shampoo composition.

Non-limiting examples of suitable non-volatile silicone hair conditioning agents, and optional suspending agents for the silicone, are described in U.S. Reissue Pat. No. 34,584, U.S. Pat. Nos. 5,104,646, 5,106,609, which descriptions are incorporated herein by reference. The optional silicone hair conditioning agent, and optional suspending agents for the optional silicone, are described in more detail hereinafter.

The optional non-volatile silicone hair conditioning agents are typically insoluble in the shampoo compositions. Typically they will be mixed in the shampoo composition to form a separate, discontinuous phase of dispersed, insoluble particles (also referred to as droplets). These droplets are typically suspended with an optional suspending agent. The optional silicone hair conditioning agent phase can be a silicone fluid and can also comprise other ingredients, such as a silicone resin, to improve silicone fluid deposition efficiency or enhance the glossiness of the hair especially when high refractive index (e.g. above about 1.46) silicone conditioning agents are used (e.g. highly phenylated silicones). The optional silicone hair conditioning agent phase may comprise volatile silicone, nonvolatile silicone, or combinations thereof. Typically, if volatile silicones are present, it will be incidental to their use as a solvent or carrier for commercially available forms of nonvolatile silicone materials ingredients, such as silicone gums and resins. The optional silicone hair conditioning agents for use in the shampoo compositions have a viscosity of from about 20 to about 2,000,000 centistokes (1 centistokes equals $1 \times 10^{-6}$ m$^2$/s) in one aspect, from about 1,000 to about 1,800,000 centistokes in another aspect, from about 50,000 to about 1,500,000 in a further aspect, and from about 100,000 to about 1,500,000 centistokes in a still further aspect, as measured at 25° C. Optional silicone fluids include silicone oils which are flowable silicone materials having a viscosity of less than 1,000,000 centistokes in one aspect, between about 5 and 1,000,000 centistokes in another aspect, and between about 10 and about 100,000 centistokes in a further aspect, at 25° C. Suitable silicone oils include polyalkyl siloxanes, polyaryl siloxanes, polyalkylaryl siloxanes, polyether siloxane copolymers, and combinations thereof. Other insoluble, nonvolatile silicone fluids having hair conditioning properties can also be used.

Optional silicone oils include polyalkyl or polyaryl siloxanes which conform to the following formula:

$$(R^{13})_3-Si-O-[-Si(R^{13})_2-O]_x-Si(R^{13})_3$$

where $R^{13}$ is aliphatic, preferably alkyl or alkenyl, or aryl, $R^{13}$ can be substituted or unsubstituted, and x is an integer from 1 to about 8,000. Suitable unsubstituted $R^{13}$ groups include alkoxy, aryloxy, alkaryl, arylalkyl, arylalkenyl, alkamino, and ether-substituted, hydroxyl-substituted, and halogen-substituted aliphatic and aryl groups. Suitable $R^{13}$ groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions herein, and are capable of being deposited on and conditioning the hair. The $R^{13}$ groups on the silicon atom of each silicone unit may represent the same or different groups. In one embodiment, two $R^{13}$ groups represent the same substituent. In one aspect the alkyl and alkenyl substituents are $C_1$ to $C_5$ alkyls and alkenyls. In another aspect from $C_1$ to $C_4$, and in a further aspect from $C_1$ to $C_2$. The aliphatic portions of other alkyl-, alkenyl-, or alkynyl-containing groups (such as alkoxy, alkaryl, and alkamino) can be straight or branched chains and have from one to five carbon atoms in one aspect, from one to four carbon atoms in another aspect, from one to three carbon atoms in a further aspect, and from one to two carbon, atoms in a still further aspect. As discussed above, the $R^{13}$ substituents hereof can also contain amino functionalities, e.g., amino groups, which can be primary, secondary or tertiary amines or quaternary ammonium groups. These include mono-, di- and tri-alkylamino and alkoxyamino groups wherein the aliphatic portion chain length is preferably as described above. The $R^{13}$ substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) allyl groups such as $-R^{14}-C(F)_3$, wherein $R^{14}$ is $C_1$-$C_3$ alkyl. Examples of such polysiloxanes include polymethyl-3,3,3 trifluoropropylsiloxane. Suitable $R^{13}$ groups include methyl, ethyl, propyl, phenyl, methylphenyl and phenylmethyl. Exemplary silicones are polydimethyl siloxane, polydiethylsiloxane, and polymethylphenylsiloxane. Polydimethylsiloxane is especially preferred. Other suitable $R^{13}$ groups include methyl, methoxy, ethoxy, propoxy, and aryloxy. The three $R^{13}$ groups on the end caps of the silicone may also represent the same or different groups. The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid. The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility In water and the composition hereof. Suitable alkylamino substituted silicones include those which conform to the following structure:

$$HO-[-Si(CH_3)_2-]_x-O-[HO-Si(-(CH_2)_3-NH-(CH_2)_2-NH_2)-O]_y-$$

wherein x and y are integers. This polymer is also known as "amodimethicone".

Suitable cationic silicone fluids include those which conform to the formula (III) $(R_1)_a \, G_{3-a} -Si-(SiG_2)_n -(-OSiG_b (R_1)_{2-b})_m -O-SiG_{3-a} (R_1)_a$, wherein G is selected from the group consisting of hydrogen, phenyl, hydroxy, $C_1$-$C_8$ alkyl and preferably methyl; a is 0 or an integer having a value from 1 to 3, preferably 0; b is 0 or 1, preferably 1; the sum n+m is a number from 1 to 2,000 and probably from 50 to 150, n being able to denote a number from 0 to 1,999 and preferably from 49 to 149 and m being able to denote an integer from 1 to 2,000 and probably from 1 to 10; $R_1$ is a monovalent radical conforming to the formula $C_qH_{2q} L$ in which q is an integer having a value of from 2 to 8 and L is selected from the following groups:

$$-N(R_2)CH_2-CH_2-N(R_2)_2$$

$$-N(R_2)_2$$

$$-N(R_2)_3A^-$$

$$-N(R_2)CH_2-CH_2-NR_2H_2A^-$$

in which $R_2$ is selected from the group consisting of hydrogen, phenyl, benzyl, a saturated hydrocarbon radical, preferably an alkyl radical containing from 1 to 20 carbon atoms, and A is a halide ion.

An exemplary cationic silicone corresponding to the previous formula is the polymer known as "trimethylsilylamodimethicone", of formula:

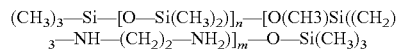

Other silicone cationic polymers which can be used in the shampoo compositions are represented by the formula:

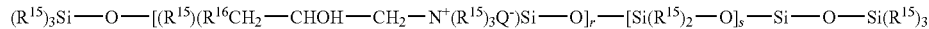

where $R^{15}$ denotes a monovalent hydrocarbon radical having from 1 to 18 carbon atoms, preferably an alkyl or alkenyl radical such as methyl; $R^{16}$ denotes a hydrocarbon radical, preferably a $C_1$ to $C_{18}$ alkylene radical or a $C_1$ to $C_{18}$, and more preferably $C_1$ to $C_8$, alkyleneoxy radical; Q is a halide ion, preferably chloride; r denotes an average statistical value from 2 to 20 in one aspect, and from 2 to 8 in another aspect; s denotes an average statistical value from 20 to 200 in one aspect, and from 20 to 50 in another aspect. A preferred polymer of this class is available from Union Carbide under the name "UCAR SILICONE ALE 56."

Other optional silicone fluids are the insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, Chemistry and Technology of Silicones, New York: Academic Press 1968; and in General Electric Silicone Rubber Product Data Sheets SE 30, SE 33, SE 54 and SE 76, all of which are incorporated herein by reference. The silicone gums will typically have a mass molecule weight in excess of about 200,000, generally between about 200,000 and about 1,000,000, specific examples of which include polydimethylsiloxane, (polydimethylsiloxane)(methylvinylsiloxane) copolymer, poly(dimethylsiloxane) (diphenyl siloxane)(methylvinylsiloxane) copolymer and mixtures thereof.

Another category of nonvolatile, insoluble silicone fluid conditioning agents are the high refractive index silicones, having a refractive index of at least about 1.46 in one aspect, at least about 1.48 in another aspect, at least about 1.52 in a further aspect, and at least about 1.55 in a still further aspect. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula above, as well as cyclic polysiloxanes wherein the silicone substituent R is as defined above, and the number of repeat unit n is from about 3 to about 7 in one aspect, and from 3 to 5 in another aspect.

The high refractive index polysiloxane fluids contain a sufficient amount of aryl-containing R substituents to increase the refractive index to the desired level, which is described above. In addition, R and n must be selected so that the material is nonvolatile, as defined above.

Aryl containing substituents contain alicyclic and heterocyclic five and six member aryl rings, and substituents containing fused five or six member rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl containing groups include substituted and unsubstituted arenes, such as phenyl, and phenyl derivatives such as phenyls with $C_1$ to $C_5$ alkyl or alkenyl substituents, e.g., allylphenyl, methyl phenyl and ethyl phenyl, vinyl phenyls such as styrenyl, and phenyl alkynes (e.g. phenyl $C_2$ to $C_4$ alkynes). Heterocyclic aryl groups include substituents derived from furan, imidazole, pyrrole, pyridine, etc. Fused aryl ring substituents include, for example, naphthalene, coumarin, and purine.

In general, the high refractive index polysiloxane fluids will have a degree of aryl containing substituents of at least about 15% in one aspect, at least about 20% in another aspect, at least about 25% in a further aspect, at least about 35% in a still further aspect, and at least about 50% in another aspect. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm$^2$, typically at least about 27 dynes/cm$^2$. Surface tension, for purposes hereof is measured by a de Nouy ring tensiometer according to Dow Corning Corporate Test Method CTM 0461, Nov. 23, 1971. Changes in surface tension can be measured according to the above test method or according to ASTM Method D 1331.

Exemplary high refractive index polysiloxane fluids have a combination of phenyl or phenyl derivative substituents (preferably phenyl), with alkyl substituents, preferably $C_1$ to $C_4$ alkyl (most preferably methyl), hydroxy, $C_1$ to $C_4$ alkylamino (especially —$R^{17}NHR^{18}NH_2$ where each $R^{17}$ and $R^{18}$ independently is a $C_1$ to $C_3$ alkyl, alkenyl, and/or alkoxy. High refractive index polysiloxanes are available from Dow Corning Corporation (Midland, Mich., U.S.A.) Huls America (Piscataway, N.J., U.S.A.), and General Electric Silicones (Waterford, N.Y., U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5% in one aspect, at least about 10% in another aspect, at least about 15% in a further aspect, at least about 20% in a still further aspect, and at least about 25% in another aspect. Reductions in surface tension of the polysiloxane fluid/spreading agent mixture can provide improved shine enhancement of the hair.

Also, the spreading agent will preferably reduce the surface tension by at least about 2 dynes/cm$^2$.

The surface tension of the mixture of the polysiloxane fluid and the spreading agent, at the proportions present in the final product, is 30 dynes/cm$^2$ or less. Typically, the surface tension will be in the range of from about 15 to about 30. The weight ratio of the highly arylated polysiloxane fluid to the spreading agent will, in general, be between about 1000:1 and about 1:1 in one aspect, between about 100:1 and about 2:1 in another aspect, between about 50:1 and about 2:1 in a further aspect, and from about 25:1 to about 2:1 in a still further aspect. When fluorinated surfactants are used, particularly high polysiloxane:spreading agent ratios may be effective due to the efficiency of these surfactants. Thus is contemplated that ratios significantly above 1000:1 may be used.

Exemplary silicone fluids for use in the shampoo compositions are disclosed in U.S. Pat. Nos. 2,826,551, 3,964,500, 4,364,837, British Patent 849,433, and Silicon Compounds, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp. 204308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3 SiO_5$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g. M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbol indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

Exemplary silicone resins for use herein which are MQ, MT, MTQ, MDT and MDTD resins. In one embodiment the silicone substituent is methyl. In one embodiment, the MQ resins have a M:Q ratio ranging from about 0.5:1.0 to about 1.5:1.0, and an average molecular weight of about 1000 to about 10,000.

The weight ratio of the nonvolatile silicone fluid, having refractive index below 1.46, to the silicone resin component, when used, is from about 4:1 to about 400:1 in one aspect, from about 9:1 to about 200:1 in another aspect, and from about 19:1 to about 100:1 in a further aspect, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

Emulsified silicones for use in hair shampoos of the invention will typically have an average silicone particle size in the composition of less than 30 in one aspect, less than 20 in another aspect, and less than 10 micrometers in a further aspect. In general, reducing the silicone particle size tends to improve conditioning performance. In one embodiment of the invention, the average silicone particle size of the emulsified silicone in the composition is less than 2 micrometers, and ideally it ranges from 0.01 to 1 micrometer. Silicone emulsions having an average silicone particle size of <0.15 micrometers are generally termed micro-emulsions. Particle size may be measured by means of a laser light scattering technique, using a 2600D Particle Sizer from Malvern Instruments. Suitable silicone emulsions for use in the invention are also commercially available in a pre-emulsified form. Examples of suitable pre-formed emulsions include emulsions DC2-1766, DC2-1784, and micro-emulsions DC2-1865 and DC2-1870, all available from Dow Corning. These are all emulsions/micro-emulsions of dimethiconol. Crosslinked silicone gums are also available in a pre-emulsified form, which is advantageous for ease of formulation. An exemplary material is available from Dow Corning as DC X2-1787, which is an emulsion of crosslinked dimethiconol gum. Another exemplary material is available from Dow Corning as DC X2-1391, which is a micro-emulsion of crosslinked dimethiconol gum. Pre-formed emulsions of amino functional silicone are also available from suppliers of silicone oils such as Dow Corning and General Electric. Particularly suitable are emulsions of amino functional silicone oils with non ionic and/or cationic surfactant. Specific examples include DC929 Cationic Emulsion, DC939 Cationic Emulsion, DC949 Cationic emulsion, and the non-ionic emulsions DC2-7224, DC2-8467, DC2-8177 and DC2-8154 (all available from Dow Corning). Mixtures of any of the above types of silicone may also be used. Particularly preferred are hydroxyl functional silicones, amino functional silicones and mixtures thereof. Specific examples of amino functional silicones suitable are the aminosilicone oils DC2-8220, DC2-8166, DC2-8466, and DC2-8950-114 (all available from Dow Corning), and GE 1149-75, (ex General Electric Silicones). An example of a quaternary silicone polymer useful in the present invention is the material K3474, available from Goldschmidt, Germany.

The water soluble or water dispersible silicones useful in the composition of the present invention contain anionic functionality, cationic functionality, or nonionic functionality. In one embodiment, the water soluble silicones contain a polysiloxane main chain to which is grafted at least one anionic moiety. The anionic moiety can be grafted to a terminal end of the polysiloxane backbone, or be grafted as a pendant side group, or both. By anionic group is meant any hydrocarbon moiety that contains at least one anionic group or at least one group that can be ionized to an anionic group following neutralization by a base. The quantity of the hydrocarbon groups of anionic character which are grafted onto the silicone chain are chosen so that the corresponding silicone derivative is water-soluble or water-dispersible after neutralization of the ionizable groups with a base. The anionic silicone derivatives can be selected from existing commercial products or can be synthesized by any means known in the art. The nonionic silicones contain alkylene oxide (e.g., ethylene oxide, propylene oxide and combinations thereof) side chain units.

Silicones with anionic groups can be synthesized i by reaction between (i) a polysiloxane containing a silinic hydrogen and (ii) a compound containing olefinic unsaturation that also contains an anionic functional group. Exemplary of such a reaction is the hydrosilylation reaction between poly(dimethylsiloxanes) containing a Si—H group(s) and an olefin, $CH_2$=CHR, wherein R represents a moiety containing an anionic group. The olefin can be monomeric, oligomeric or polymeric. Polysiloxane compounds that contain a pendant reactive thio (—SH) group(s) are also suitable for grafting an unsaturated anionic group containing compound to the poly (siloxane) backbone.

According to one aspect of the present invention, the anionic monomers containing ethylenic unsaturation are used alone or in combination and are selected from linear or branched, unsaturated carboxylic acids. Exemplary unsaturated carboxylic acids are acrylic acid, methacrylic acid, maleic acid, maleic anhydride, itaconic acid, fumaric acid and crotonic acid. The monomers can optionally be partially or completely neutralized by base to form an alkali, alkaline earth metal, and ammonium salt. Suitable bases include but are not limited to the alkali, alkaline earth (e.g., sodium, potassium, lithium, calcium) and ammonium hydroxides. It will be noted that, similarly, the oligomeric and polymeric graft segments formed from the forgoing monomers can be post-neutralized with a base (sodium hydroxide, aqueous ammonia, etc) to form a salt. Examples of silicone derivatives which are suitable for use in the present invention are described in patent applications numbers EP-A-0 582,152 and WO 93/23009. An exemplary class of silicone polymers are the polysiloxanes containing a repeat unit represented by the following structure:

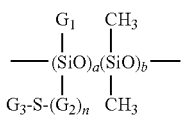

wherein $G_1$ represents hydrogen, $C_1$ to $C_{10}$ alkyl or phenyl radical; $G_2$ represents $C_1$ to $C_{10}$ alkylene; $G_3$ represents an anionic polymeric residue obtained from the polymerization of at least one anionic monomer containing ethylenic unsaturation; n is 0 or 1; a is an integer ranging from 1 to 50; and b is an integer from 10 to 350. In one embodiment of the invention $G_1$ is methyl; n is 1; and $G_2$ is propylene radical; $G_3$ represents a polymeric radical obtained from the polymerization of at least one unsaturated monomer containing a carboxylic acid group.

The carboxylate group content in the final polymer preferably ranges from 1 mole of carboxylate per 200 g of polymer to 1 mole of carboxylate per 5000 g of polymer. The number molecular mass of the silicone polymer preferably ranges from 10,000 to 1,000,000 and still more preferably from 10,000 to 100,000. Exemplary unsaturated monomers containing carboxylic acid groups are acrylic acid and methacrylic acid. In addition, to the carboxylic acid group containing monomers, $C_1$ to $C_{20}$ alkyl esters of acrylic acid and methacrylic acid can be copolymerized into the polymeric backbone. Exemplary esters Include but are not limited to the ethyl and butyl esters of acrylic and methacrylic acid. A commercially available silicone-acrylate polymer is marketed by the 3M Company under the trademark Silicones "Plus" Polymer 9857C (VS80 Dry). These polymers contain a polydimethylsiloxanes (PDMS) backbone onto which is grafted (through a thiopropylene group) random repeating units of poly(meth)acrylic acid and the butyl ester of poly (meth)acrylate. These products can be obtained conventionally by radical copolymerization between thiopropyl functionalized polydimethylsiloxane and a mixture of monomers comprising (meth)acrylic acid and of butyl (meth)acrylate.

The hair compositions in accordance with one embodiment of the invention contain the water soluble silicone derivatives defined above in a weight range from about 0.05% to about 10% in one aspect, from about 0.1% to about 5% in another aspect and from about 0.2% to 3% by weight in a still further aspect based on the total weight of the composition.

It should be noted that in the above structure units EO and PO may be in random and block structures.

In another embodiment the water soluble silicones useful in the practice of the present invention can be represented silicone carboxylates represented by the formulae:

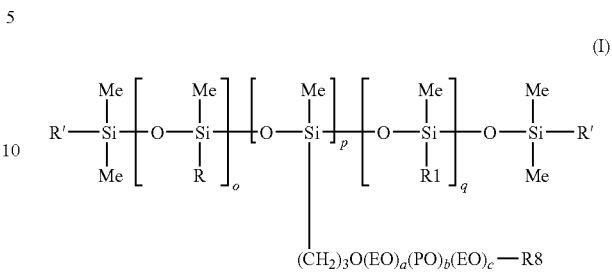

wherein Me is methyl; R and R' are independently selected from methyl, —OH, —$R^7$, and —$R^9$—A' or —$(CH_2)_3$—O—$(EO)_a$-$(PO)_b$-$(EO)_c$-G with the proviso that both R and R' are not methyl, —OH or $R^7$; $R^1$ is selected from lower alkyl $CH_3(CH_2)_n$— or phenyl where n is an integer from 0 to 22; a, b, and c are integers independently ranging from 0 to 100; EO is —$CH_2CH_2O$)—; PO is —$(CH_2CH(CH_3)O)$—; o is an integer ranging from 1 to 200; q is an integer ranging from 0 to 1000; p is an integer ranging from 0 to 200; $R^7$ is aryl, alkyl, aralkyl, alkaryl, or alkenyl group of 1-40 carbons; $R^8$ is hydrogen or $R^7$ or C(O)—X wherein X is aryl, alkyl, aralkyl, alkaryl, alkenyl group of 1-40 carbons, or a mixture thereof; $R^9$ is divalent group selected from alkylene of 1-40 carbons which may be interrupted with arylene group of 6 to 18 carbons or an alkylene group containing unsaturation of 2 to 8 carbons; A' and G are independently are selected from:

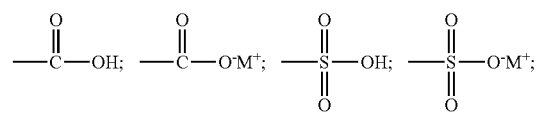

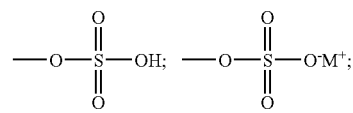

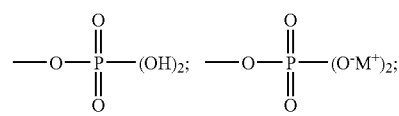

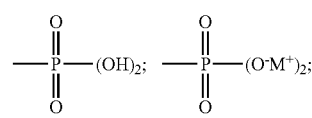

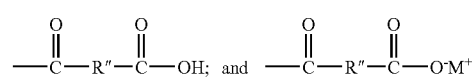

where R" is a divalent group selected from alkylene of 1-40 carbons which may be interrupted with an arylene group of 6 to 18 carbons or an alkylene group of 2 to 8 carbons, and is preferably selected from —$CH_2$—$CH_2$—; —CH=CH—; —$CH_2$—$CH(R^7)$;

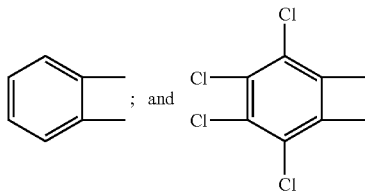 ; and where M is Na, K, Li, NH$_4$; or an amine containing C$_1$ to C$_{10}$ alkyl, C$_6$ to C$_{14}$ aryl (e.g., phenyl, napthtyl), C$_2$ to C$_{10}$ alkenyl, C$_1$ to C$_{10}$ hydroxyalkyl, C$_7$ to C$_{24}$ arylalkyl or C$_7$ to C$_{24}$ alkaryl groups;

(II)

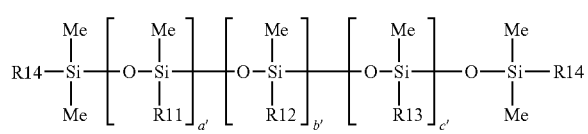

wherein Me is methyl, R$^{11}$ is selected from lower alkyl having one to eight carbon atoms or phenyl, R$^{12}$ is —(CH$_2$)$_3$—O-(EO)$_x$-(PO)$_y$-(EO)$_z$-SO$_3^-$M$^+$; M is a cation and is selected from Na, K, Li, or NH$_4^+$; x, y and z are integers independently ranging from 0 to 100; R$^{13}$ is —(CH$_2$)$_3$—O-(EO)$_x$-(PO)$_y$-(EO)$_z$-H; R$^{14}$ is methyl or hydroxyl; a$^1$ and c$^1$ are independently integers ranging from 0 to 50; b$^1$ is an integer ranging from 1 to 50;

(III)

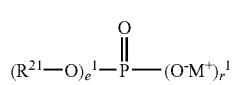

wherein R$^{21}$ is

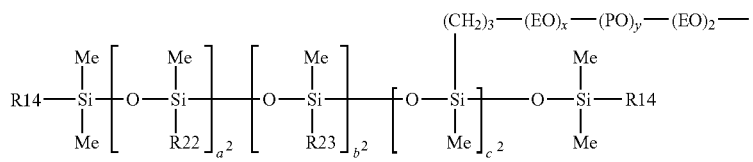

Me is methyl, a$^2$ is an Integer from 0 to 200; b$^2$ is an integer from 0 to 200; c$^2$ is an integer from 1 to 200; R$^{14}$ is as defined above; R$^{22}$ is selected from —(CH$_2$)$_n$CH$_3$ and phenyl; n is an integer from 0 to 10; R$^{23}$ is —(CH$_2$)$_3$—O—(EO)$_x^1$—(PO)$_y^1$-(EO)$_z^1$—H; x$^1$, y$^1$ and z$^1$ are integers and are independently selected from 0 to 20; e$^1$ and f$^1$ are 1 or 2 with the proviso that e+f=3; M is selected from H, Na, K, Li, or NH$_4$; and (IV)

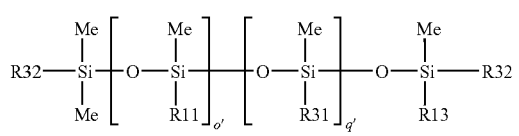

wherein; Me is methyl; R$^{30}$ and R$^{32}$ independently are —CH$_3$ or —(CH$_2$)$_3$—O-(EO)$_a^3$—(PO)$_b^3$-(EO)$_c^3$—C(O)—R$^{33}$—C (O)—OH; with the proviso that both R$^{30}$ and R$^{32}$ are not —CH$_3$; R$^{33}$ is selected from —CH$_2$—CH$_2$; —CH=CH—; —CH$_2$—CH(R$^{37}$);

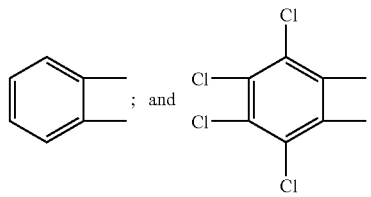 ; and

R$^{37}$ is alkyl having from 1 to 22 carbon atoms; R$^{31}$ is selected from lower alkyl (having 1 to 4 carbons), CH$_3$(CH)$_n^1$— and phenyl; n$^1$ is an integer from 0 to 8; a$^3$, b$^3$ and c$^3$ are integers independently ranging from 0 to 20; EO is an ethylene oxide residue —(CH$_2$CH$_2$—O)—;

PO is a propylene oxide residue —(CH$_2$CH(CH$_3$)O—; o$^1$ is an integer ranging from 1 to 200; q$^1$ is an integer ranging from 0 to 500.

The foregoing silicone carboxylates are disclosed in greater detail in U.S. Pat. No. 5,296,625, the disclosure of which is incorporated herein by reference. Still further silicone are silicones containing a multiplicity of different anionic substituents. Such silicones can be prepared by reacting two or more types of anionic silicones already disclosed using reactions well known to those in the art. The resulting molecule could be a hybrid of the starting silicones and would, therefore, contain multiple types of anionic functional groups. The properties of the silicone can be optimized in such a fashion. One type of reaction, the silicone equilibration reaction, involves charging a reactor with raw materials, adding a suitable catalyst, mixing with heat, and then neutralizing the catalyst. The Chemistry is discussed in Silicone in Organic, Organometallic and Polymer Chemistry (Michael Brook)—John Wiley and Sons, New York, 2000, pp. 261-266.

Other water soluble silicones useful in the invention are quaternary silicone polymers. These polymers have a pendant quaternary nitrogen functional group present. The silicones are represented by the following formula: (V)

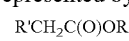

wherein R is

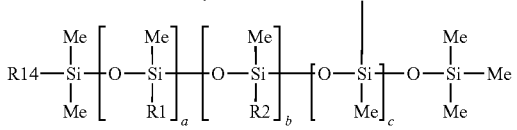

Me is methyl, a is an integer from 0 to 200; b is an integer from 0 to 200; c is an integer from 1 to 200; R$^1$ is selected from —(CH$_2$)$_n$CH$_3$ and phenyl; n is an integer from 0 to 10; R$^2$ is —(CH$_2$)$_3$—(OCH$_2$ CH$_2$)$_x$—(OCH$_2$ CH(CH$_3$)$_y$—(OCH$_2$ CH$_2$)$_z$—OH; x, y and z are integers and are independently selected from 0 to 20; R' is represented by the formulae:

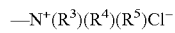

wherein $R^3$, $R^4$, and $R^5$ independently represent alkyl having from 1 to 20 carbon atoms;

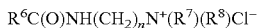

wherein $R^6$ is alkyl having from 6 to 20 carbon atoms, $R^7$ and $R^8$ are independently methyl or ethyl; n is an integer from 1 to 5;

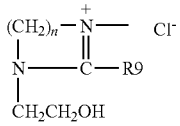

wherein $R^9$ is alkyl having from 6 to 20 carbon atoms, and v is an integer from 1 to 5. Such silicones are disclosed in greater detail in U.S. Pat. No. 5,153,294, the disclosure of which is incorporated herein by reference.

Other suitable water soluble silicones are represented by the following formula:

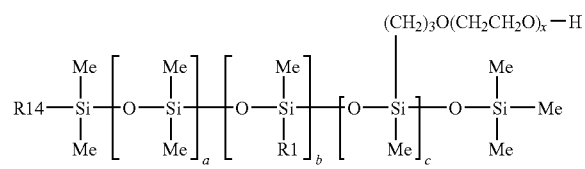

Me is methyl, a is an integer from 0 to 200; b is an integer from 0 to 200; c is an integer from 1 to 200; $R^1$ is selected from —NH—$(CH_2)_n$—$NH_2$ or —$(CH_2)_n$—$NH_2$, n is an integer from 2 to 6; and x, is n integer from 0 to 20.

The total amount of silicone incorporated into compositions of the invention depends on the level of conditioning desired and the material used. An exemplary amount is from 0.01 to about 10% by weight of the total composition although these amounts are not absolute. The lower amount is determined by the minimum level to achieve conditioning and the upper amount by the maximum level to avoid making the hair and/or skin unacceptably greasy.

When the silicone is incorporated as a pre-formed emulsion as described above, the exact quantity of emulsion will of course depend on the concentration of the emulsion, and should be selected to give the desired quantity of silicone in the final composition.

The shampoo compositions of the present invention are aqueous systems which comprise from about 20% to about 94% in one aspect, from about 50% to about 90% in another aspect, and from about 60% to about 85% in a further aspect, water by weight of the composition.

The shampoo composition may further comprise a suspending or thickening agent. Suitable suspending agents for such materials are well known in the art, and include crystalline and polymeric suspending or thickening agents.

Optional suspending agents include crystalline suspending agents that can be categorized as acyl derivatives, long chain amine oxides, or combinations thereof, concentrations of which range from about 0.1% to about 5.0% in one aspect, and from about 0.5% to about 3.0% in another aspect by weight of the shampoo compositions. These suspending agents are described in U.S. Pat. No. 4,741,855, the description of which is incorporated herein by reference. These exemplary suspending agents include ethylene glycol esters of fatty acids preferably having from about 12 to about 22 carbon atoms. More preferred are the ethylene glycol stearates, both mono and distearate, but particularly the distearate containing less than about 7% of the mono stearate. Other suitable suspending agents Include alkanol amides of fatty acids, preferably having from about 12 to about 22 carbon atoms examples of which include stearic monoethanolamide, stearic diethanolamide, stearic monoisopropanolamide and stearic monoethanolamide stearate. Other long chain acyl derivatives include long chain esters of long chain fatty acids having from about 12 to about 22 carbon atoms (e.g., stearyl stearate, cetyl palmitate, etc.); glyceryl esters (e.g., glyceryl distearate) and long chain (hydrocarbyl) esters of long chain alkanol amides (e.g., stearamide diethanolamide distearate, stearamide monoethanolamide stearate). Long chain (hydrocarbyl) acyl derivatives, ethylene glycol esters of long chain carboxylic acids, long chain (hydrocarbyl) amine oxides, and alkanol amides of long chain carboxylic acids in addition to the preferred materials listed above may be used as suspending agents. By long chain hydrocarbyl is meant a hydrocarbyl moiety containing 8 to 22 carbon atoms. The long chain hydrocarbyl groups can be selected from alkyl and alkenyl moieties. The alkenyl groups can be mono-unsaturated or multi-unsaturated. Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Non-limiting examples of optional polymeric thickening agents for use in the shampoo composition include carboxyvinyl polymers, cellulose ethers, polyvinyl alcohol, polyvinyl pyrrolidone, hydroxypropyl starch and starch derivatives, and xantham gum. Suspending or thickening agents are described in U.S. Pat. Nos. 2,798,053, 4,686,254, 4,788,006, and 5,275,761, which descriptions are incorporated herein by reference.

Examples of suitable long chain amine oxides for use as suspending agents include alkyl ($C_{16}$ to $C_{22}$) dimethyl amine oxides, e.g., stearyl dimethyl amine oxide.

Other suitable suspending agents include xanthan gum at concentrations ranging from about 0.3% to about 3% in one aspect, and from about 0.4% to about 1.2% in another aspect, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference.

Other suitable suspending agents include carboxyvinyl polymers. Preferred among these polymers are the homo polymers and copolymers of acrylic acid crosslinked with polyallylsucrose as described in U.S. Pat. No. 2,798,053, which description is incorporated herein by reference. Useful comonomers include but are not limited to methacrylic acid, $C_1$ to $C_{10}$ alkyl esters of acrylic acid, $C_1$ to $C_{10}$ alkyl esters of methacrylic acid, and mixtures thereof. Examples of these polymers include Carbopol® 934, 940, 941, and 956 carbomer available from Noveon, Inc.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents Include di(hydrogenated tallow) phthalic acid amide, and crosslinked maleic anhydride-methyl vinyl ether copolymer.

Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hydropylcellulose, hydroxypropyl methylcellulose, hydroxyethyl ethylcellulose and hydrorxethylcellulose), polyvinyl alcohol, polyvinyl pyrrolidone, starch and starch derivatives, and other thickeners, viscosity modifiers, gelling agents, etc. Mixtures of these materials can also be used.

A further component in shampoo compositions of the invention is a fatty acid polyester of a polyol selected from cyclic polyols, sugar derivatives and mixtures thereof. By "polyol" is meant a material having at least four hydroxyl groups. The polyols used to prepare the fatty acid polyester typically have from about 4 to 12 in one aspect, from about 4 to 11 in another aspect, and from about 4 to 8 hydroxyl groups in a further aspect. By "fatty acid polyester" is meant a material in which at least two of the ester groups are (independently of one another) attached to a fatty ($C_8$ to $C_{22}$ alkyl or alkenyl) chain. For a given material, prefixes such as "tetra-", "penta-" indicate the average degrees of esterification. The compounds exist as a mixture of materials ranging from the monoester to the fully esterified ester.

Cyclic polyols are the preferred polyols used to prepare the fatty acid polyester in the present invention. Examples include inositol, and all forms of saccharides. Saccharides, in particular, monosaccharides and disaccharides, are especially preferred.

Examples of monosaccharides include xylose, arabinose, galactose, fructose, sorbose and glucose.

Examples of disaccharides include maltose, lactose, cellobiose and sucrose. Sucrose is especially preferred. Examples of suitable sugar derivatives include sugar alcohols, such as xylitol, erythritol, maltitol and sorbitol, and sugar ethers such as sorbitan.

The fatty acids used to prepare the fatty acid polyester in the present invention have from 8 to 22 carbon atoms. They can be branched or linear, and saturated or unsaturated. Examples of suitable fatty acids include caprylic, capric, lauric, myristic, myristoleic, palmitic, palmitoleic, stearic, 12-hydroxystearic, oleic, ricinoleic, linoleic, linolenic, arachidic, arachidonic, behenic, and erucic acids. Erucic acid is particularly preferred. Mixed fatty acid moieties from source oils which contain substantial amounts of the desired unsaturated or saturated acids can be used as the acid moieties to prepare fatty acid polyesters suitable for use in the hair treatment composition of the invention. The mixed fatty acids from the oils should contain at least 30%, preferably at least 50% of the desired unsaturated acids. For example, high erucic rapeseed oil fatty acids can be used instead of pure $C_{20}$ to $C_{22}$ unsaturated acids, and hardened, i.e., hydrogenated, high erucic rapeseed oil fatty acids can be used instead of pure $C_{20}$ to $C_{22}$ saturated acids. Preferably the $C_{20}$ and higher acids, or their derivatives, e.g. methyl or other lower alkyl esters, are concentrated, for example by distillation. The fatty acids from palm kernel oil or coconut oil can be used as a source of $C_8$ to $C_{12}$ acids, and those from cotton seed oil and soy bean oil as a source of $C_{16}$ to $C_{18}$ acids.

Specific examples of suitable fatty acid polyesters are sucrose pentalaurate, sucrose tetraoleate, sucrose pentaerucate, sucrose tetraerucate, sucrose tetrastearate, sucrose pentaoleate, sucrose octaoleate, sucrose pentatallowate, sucrose trirapeate, sucrose tetrarapeate, sucrose pentarapeate, sucrose tristearate and sucrose pentastearate, and mixtures thereof. Sucrose pentaerucate and sucrose tetraerucate are particularly preferred. These materials are available commercially as Ryoto Sugar Esters available from Mitsubishi Kasei Foods.

It is also advantageous if the ester groups of the fatty acid polyester are independently attached to a fatty ($C_8$ to $C_{22}$ alkyl or alkenyl) chain or a short chain alkyl ($C_2$ to $C_8$) chain and in which the number ratio of $C_8$ to $C_{22}$ groups to $C_2$ to $C_{-8}$ groups in the fatty acid polyester molecule ranges from 5:3 to 3:5 in one aspect, from 2:1 to 1:2 in another aspect, and about 1:1 in a further aspect. The polyol used to prepare such a material is preferably a saccharide, most preferably glucose, with at least five of the hydroxyl groups being. These products are in the main oils and are thus easy to formulate. Specific examples are glucose penta esters where about 50% by number of the ester groups are acetyl groups and about 50% by number of the ester groups are octanoyl, decanoyl or dodecanoyl groups respectively. The synthesis of this type of material is described in WO 98/16538. The fatty acid polyester can be prepared by a variety of methods well known to those skilled in the art. These methods include acylation of the cyclic polyol or reduced saccharide with an acid chloride; transesterification of the cyclic polyol or reduced saccharide fatty acid esters using a variety of catalysts; acylation of the cyclic polyol or reduced saccharide with an acid anhydride and acylation of the cyclic polyol or reduced saccharide with a fatty acid. Typical preparations of these materials are disclosed in U.S. Pat. No. 4,386,213 and Australian AU 14416/88.

The total amount of fatty acid polyester in hair treatment compositions of the invention is generally from 0.001 to 10% by weight in one aspect, from 0.01 to 5% in another aspect, and from 0.01% to 3% by weight of the total hair treatment composition in a further aspect.

The shampoo compositions of the present invention may further comprise one or more optional components known for use in hair care or personal care products, provided that the optional components are physically and chemically compatible with the essential component described herein, or do not otherwise unduly impair product stability, aesthetics or performance. Concentrations of such optional components typically and individually range from about 0.001% to about 10% by weight of the shampoo compositions.

Non-limiting examples of optional components for use in the shampoo composition include anti static agents, anti dandruff agents, conditioning agents (hydrocarbon oils, fatty esters other than the synthetic esters described herein, silicone) dyes, organic solvents or diluents, pearlescent agents, foam boosters, additional surfactants or cosurfactants (nonionic, cationic), pediculocides, pH adjusting agents, perfumes, preservatives, proteins, skin active agents, styling polymers, sunscreens, vitamins, and viscosity adjusting agents.

Compositions of this invention may contain any other ingredient normally used in hair treatment formulations. These other ingredients may include viscosity modifiers, preservatives, coloring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally, these optional ingredients are included individually at a level of up to about 5% by weight of the total composition.

The shampoo compositions of this invention can also contain adjuvants suitable for hair care. Generally such ingredients are included individually at a level of up to 2% by weight of the total composition. Suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts.

(ii) hair fiber benefit agents. Examples are: ceramides, for moisturizing the fiber and maintaining cuticle integrity. Ceramides are available by extraction from natural sources, or as synthetic ceramides and pseudoceramides. A preferred ceramide is Ceramide II, available from Quest. Mixtures of ceramides are also suitable, such as Ceramides LS, available from Laboratories Serobiologiques. Free fatty acids, for cuticle repair and damage prevention. Examples are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. A preferred fatty acid is oleic acid. The fatty acids may be added singly, as mixtures, or in the form of blends derived from extracts of, e.g., lanolin. Mixtures of any of the foregoing active ingredients may also be used.

The shampoo compositions of the present invention comprise the wet minced or co-minced cationic galactomannan polymer as a hair conditioning agent or depositing aid derived from the process of the invention. The concentration of the wet minced or co-minced cationic, conditioning polymer of the shampoo composition should be sufficient to provide the desired conditioning benefits. Such concentrations generally range from about 0.025% to about 3% in one aspect, from about 0.05% to about 2% in another aspect, and from about 0.1% to about 1%, by weight of the shampoo composition a further aspect.

The wet minced or co-minced cationic conditioning polymer of this invention contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the shampoo composition. Any anionic counterions can be used in association with the cationic conditioning polymers so long as the polymers remain soluble in water, in the shampoo composition, or in a coacervate phase of the shampoo composition, and so long as the counterions are physically and chemically compatible with the components of the shampoo composition or do not otherwise unduly impair product performance, stability or aesthetics. Non-limiting examples of such counterions include halides (e.g., chlorine, fluorine, bromine, iodine), sulfates and methylsulfates.

The cationic nitrogen-containing moiety of the cationic polymer is generally present as a substituent on all, or more typically on some, of the monomer units thereof. Thus, the cationic polymer for use in the shampoo composition includes homopolymers, copolymers, terpolymers, and so forth, of quaternary ammonium or cationic amine-substituted monomer units, optionally in combination with non-cationic monomers referred to herein as spacer monomers. Non-limiting examples of such polymers are described in the CTFA Cosmetic Ingredient Dictionary, 3rd edition, edited by Estrin, Crosley, and Haynes, The Cosmetic, Toiletry, and Fragrance Association, Inc., Washington, D.C. (1982), which description is incorporated herein by reference.

The cationic nitrogen-containing group will generally be present as a substituent on a portion of the total monomer units of the cationic polymer. Thus, when the polymer is not a homopolymer, it can contain spacer non-cationic monomer units. Such polymers are described in the CTFA Cosmetic Ingredient Directory, 3rd Edition. The ratio of the cationic to non-cationic monomer units is selected to give a polymer having a cationic charge density in the required range.

The shampoo compositions of the present invention are used in a conventional manner for cleansing and conditioning hair or skin. An effective amount of the composition for cleansing and conditioning the hair or skin is applied to the hair or skin; that has preferably been wetted with water, and then rinsed off. Such effective amounts generally range from about 1 gm to about 50 gm in one aspect, and from about 1 gm to about 20 gm in another aspect. Application to the hair typically includes working the composition through the hair such that most or all of the hair is contacted with the composition.

This method for cleansing and conditioning the hair or skin comprises the steps of: a) wetting the hair or skin with water, b) applying an effective amount of the shampoo composition to the hair or skin, and c) rinsing the applied areas of skin or hair with water. These steps can be repeated as many times as desired to achieve the desired cleansing and conditioning benefit.

Toothpastes

The wet minced and co-minced hydrocolloid compositions of the present invention are useful in the preparation of thickened and stabilized toothpastes and other cosmetic materials, such as gel and paste shampoos, hand cleaners, skin fresheners, skin cleaners and perfumes. Also, related types of compositions, such as salves and ointments, thickened liquid soaps and detergents and various other preparations in which wet minced or co-minced hydrocolloids are employed to stabilize and/or thicken the products, can be improved. Hereinafter, specific reference will be to toothpastes, which are often more difficult to stabilize and thicken due to the content of insoluble particulate materials and to the more stringent standards applied to such products because they are employed orally.

Dentifrice compositions, such as toothpastes, normally comprise a humectant vehicle, a polishing agent, a gelling agent (binder) and a surface active agent or a detersive material. The usual vehicle for dentifrices is water and lower polyhydric alcohols of 3 to 6 hydroxyl groups and 3 to 6 carbon atoms per molecule. Exemplary humectant vehicles are glycerol and sorbitol or mixtures thereof, usually in an aqueous medium. When transparent dentifrices, often referred to as gel dentifrices, are manufactured, the index of refraction of vehicle used will be approximately the same as that of the polishing agent and the proportion of moisture in the product will often be held to a minimum. Instead of glycerol and sorbitol, other liquid polyols can also be utilized.

Exemplary polyols include as polyethylene glycols, mannitols (other sugar alcohols) and polyoxyethylene alcohols.

Dentifrice polishing agents are usually finely divided water insoluble powdered materials of particle sizes such that they pass a 140 mesh screen (aperture size: 140 micrometers), U.S. Standard Sieve series. In one aspect of the invention, the particle size range is from about 1 to about 40 micrometers in diameter, in another aspect from about 2 to about 20 micrometers in diameter. Examples of suitable inorganic water insoluble powdered materials are dicalcium phosphate, tricalcium phosphate, insoluble sodium metaphosphate, crystalline silica, colloidal silica, complex aluminosilicates, aluminum hydroxide (including alumina trihydrate), magnesium phosphate, magnesium carbonate, calcium carbonate, calcium pyrophosphate, bentonite, talc, calcium silicate, calcium aluminate, aluminum oxide, aluminum silicate and silica xerogels, all of which have polishing activity but are not objectionably abrasive.

The synthetic organic detergents or surface active agents which can be employed in the present compositions assist in emulsifying or otherwise dispersing the components of the dentifrice uniformly and add their cleaning action to the product. In some cases, they are germicidal and aid in prophylaxis. Although the organic surface active materials used may be anionic, nonionic, ampholytic or cationic, it is generally preferred to employ, at least as a major detersive constituent, either an anionic or nonionic material or mixture thereof. Of the anionics and cationics, the anionics are usually found to be superior in most compositions and a reason for such superiority is their desirable foaming action, in addition to their excellent cleaning ability. Generally, the anionic detergents will include long chain hydrophobic fatty or poly-lower alkoxy groups plus hydrophilic groups. These detergents will normally be in the form of salts, especially water soluble salts of alkali metals. Among the anionic detergents that are useful may be named the higher fatty acid monoglyceride sulfates, the higher alkyl sulfates, higher linear alkyl aryl sulfonates, higher olefin sulfonates, higher alkyl sulfoacetates, higher aliphatic acyl amides of lower aliphatic aminocarboxylic acid compounds, higher alkyl poly-lower alkoxy (of 3 to 100 alkoxy groups) sulfates and higher fatty acid soaps. Normally, the higher alkyl groups will be 10 to 18 or 12 to 16 carbon atoms, as will be the higher olefins, the aliphatic groups will be alkyls, preferably normal alkyls, and the aromatic groups will be benzene. Examples of such materials include sodium hydrogenated coconut oil fatty acids monoglyceride monosulfate, sodium lauryl sulfate, sodium linear tridecylbenzene sulfonate, sodium N-lauryl sarcoside and sodium cocate. Among the nonionic detergents are those including chains of lower alkylene oxides, e.g., ethylene oxide, propylene oxide, in which ethylene oxide chains make up the hydrophilic portions. Such materials are commercially available under the following brand names Pluronic™, Igepal™, Ucon™, Neodol™ and Tergitol™. In one aspect of the invention, Neodol 25-7 detergent and Neodol 45-11 detergent are employed. Additional suitable detergents are recited in the text *Surface Active Agents*, Vol. II (1958), by Schwartz, Perry and Berch.

In addition to the four main types of constituents of dentifrices, the gelling agent of which still is to be discussed, it is recognized that there are present in many dentifrices various other materials, including flavorings, enamel hardening agents, antibacterial compounds, astringent compounds, protein precipitating agents and effervescent mixtures. Any suitable flavoring or sweetening materials may be employed in formulating a flavor for the compositions of the present invention. Examples of suitable flavoring constituents include the flavoring oils, e.g., oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitable flavor and sweetening agent may together comprise from about 0.01 to 5% or more of the composition.

Antinucleating agents containing phosphonic groups have been described in the art as dentifrice components. They are recognized to provide desirable anticalculus or antiplaque properties to the toothpaste composition. Antinucleating agents are disclosed in the following U.S. Pat. Nos. 4,348,381; 4,224,309; and 4,224,308; 4,215,105; 4,183,915 4,177,258; 4,144,324; 4,143,128; 4,137,303; 4,123,512; 4,100,270, 4,098,880; 4,042,679; 4,064,164; 4,108,962; 4,108,961; 4,034,086; 3,988,443; 3,960,888; 3,941,772; 3,925,456; 3,959,458; 4,025,616; 3,937,807; and 3,934,002. The amount of antinucleating agent to employ in the composition can range from about 0.01 to 10% by weight in one aspect, 0.1 to 5% by weight in another aspect, and from about 1 to 3% by weight in a further aspect based on the weight of the composition. They include acid and non-toxic pharmaceutically acceptable salts (e.g., ammonium and alkali metal, particularly sodium of 2-phosphonobutane tricarboxylic acid-1,2,4; phosphonoacetic acid; alkylene diamine tetramethylene phosphonic acids containing 1 to 10 alkylene groups; polyalkyl bis-(phosphonomethylene) amine acid; 1,3di-amino-alkane-1,1-diphosphonic acid as set forth in U.S. Pat. No. 4,064,164; 3-amino-1-hydroxypropane-1,1-diphosphonic acid; azacycloalkane-2,2-diphosphonic acid containing 4 to 6 carbon atoms in the heterocyclic ring; pyrrolidone-5,5-diphosphonic acid wherein the hetero-N atom is substituted with hydrogen or an alkyl group containing 1 to 6 carbon atoms; azacycloalkane-2,2-diphosphonic acid wherein the hetero-N atom is substituted with hydrogen or an alkyl group containing 1 to 3 carbon atoms and containing 4 to 6 carbon atoms in the hetrocyclic ring; 2-hydroxy-2-oxo-3-amino-3-phosphonyl-5-oxo-1-aza-2-phospha-cycloalkanes as set forth in U.S. Pat. No. 3,925,456; anticalculus agents of U.S. Pat. No. 3,959,458 typified by ethane-1-hydroxy-1,1-diphosphonic acid. Alkylene diamine tetramethylene phosphonic salts, particularly sodium salts of ethylene diamine tetramethylene phosphonic acid are preferred.

The dentifrice may contain a compound which provides at least about 100 ppm, of fluoride, typically about 100 to 10000 ppm, typically about 750 to 2000 ppm. Compounds which provide fluorine Include sodium fluoride, stannous fluoride, potassium fluoride, potassium stannous fluoride, sodium hexafluorostannate, stannous chlorofluoride, sodium monofluorophosphate and amine fluorides including mixtures thereof. Most typically in accordance with the present invention sodium fluoride, sodium monofluorophosphate or a mixture of sodium monofluorophosphate and sodium fluoride may be employed.

The dentifrice may preferably contain sodium fluoride or sodium monofluorophosphate or a mixture of sodium monofluorophosphate and sodium fluoride in amount to provide about 100 to 10000 ppm of fluorine in one aspect, about 750 to 2000 ppm in another aspect, about 1400 to 2000 ppm in a further aspect, and 1400 to 1670 ppm in a still further aspect. A binary fluoride system of sodium monofluorophosphate and sodium fluoride is desirably used in which about 30 to 40% of the fluorine is provided by sodium fluoride.

Commercially available sodium monofluorophosphate, $Na_2PO_3F$, varies considerably in purity. It may be used at any suitable purity level provided that the impurities do not adversely affect the desired properties. In general, the sodium monofluorophosphate is desirably at least 80% pure. For better results, it should be at least 85% pure, and for best results at least 90% pure, with the balance being composed primarily by-products of manufacture such as sodium fluoride and water-soluble sodium phosphate salt. Expressed in another way, the sodium monofluorophosphate employed should have a total fluoride content of above 12% in one aspect, and above 12.7% in another aspect. In addition, it should not have a sodium fluoride content of not more then 1.5% and preferably not more than 1.2%.

Various other materials may be Incorporated in the dentifrices of this invention. Examples thereof are coloring or whitening agents, preservatives, such as methyl p-hydroxybenzoate or sodium benzoate, stabilizers, silicones, chlorophyll compounds and ammoniated materials such as urea, diammonium phosphate and mixtures thereof. These adjuvants are incorporated in the instant compositions in amount which do not substantially adversely affect the desired properties and characteristics and are suitably selected and used in conventional amounts.

For some applications, it will be necessary to include antibacterial agents in the compositions of the present invention. Typical antibacterial agents which may be used in amounts of about 0.01% to about 5%, preferably about 0.05% to about 1.0%, by weight of the dentifrice composition include $N^1$-4 (chlorobenzyl)-$N^5$-(2,4-dichlorobenzyl) biguanide; p-chlorophenyl biguanide; 4-chlorobenzhydryl biguanide; 4-chlorobenzhydrylguanylurea; N-3-lauroxypropyl-$N^5$-p-chlorobenzylbiguanide; 1,6-di-p-chlorophenylbiguanidehexane; 1-(lauryidimethylammonium)-8-(p-chlorobenzyldimethylammonium) octane dichloride; 5,6-dichloro-2-guanidinobenzimidazole; $N^1$-p-chlorophenyl-$N^5$-laurylbiguanide; 5-amino-1,3-bis(2-ethylhexyl)-5-methylhexahydropyrimidine; and their non-toxic acid addition salts.

The dentifrices should have a pH practicable for use. A pH range of 5 to 9 is particularly desirable. The reference to the pH is meant to be the pH determination directly on the dentifrice. If desired, materials such as benzoic, or citric acid may be added to adjust the pH to 5.5 to 6.5.

The typical creamy or gel consistency of dentifrices is imparted by a gelling or binding agent, which is sometimes supplemented with a non-gelling thickener. Many combinations of gelling agents such as cellulosic materials, seaweed derivatives, and xanthan can be co-minced with polygalactomannan splits in accordance with the process of the invention to form thickening agent meeting the criteria for thickening toothpaste formulations.

Xanthan gum is a fermentation product prepared by action of the bacteria of the genus *Xanthomonas* upon carbohydrates. Four species of *Xanthomonas*, viz *X. campetris. X. phaseoli, X. malvocearum*, and *X. carotae* are reported in the literature to be the most efficient gum procedures. Although the exact chemical structure is not determined, it is generally accepted to be a heteropolysaccharide with a molecular weight of several million. It contains D-glucose, D-mannose, and D-glucuronic acid in the molar ratio of 2.8:3.2.0. The molecule contains 4.7% acetyl and about 3% pyruvate. The proposed chemical structure configuration can be found in McNeely and Kang, Industrial Gums, ed. R. L. Whistler, CH XXI, 2nd Edition, New York, 1973. The procedure for growing, isolating and purifying the xanthan gum is also found in that publication. Further description of xanthan gum is found in Manufacturing Chemist, May 1960, pp. 206-208 (including mention at page 208 of potential use of gums therein described for formulating toothpastes).

Sodium carboxymethyl cellulose, hydroxyethylcarboxyethyl cellulose, polyvinyl pyrrolidone, gum tragacanth, hydroxypropylmethyl cellulose, methyl cellulose, starch, starch glycolate, polyvinyl alcohol, sodium alginate, carob bean gum and hydrophilic colloidal hydroxyvinyl polymers, such as Carbopol® carbomer, can also be used in to thicken the toothpaste formulations.

Not only are commercially available carrageenans, such as mixtures of the sodium salts of lambda and kappa carrageenans, useful in the process of the invention, other carrageenan salts, such as the calcium, potassium, and sodium salts of lambda, kappa and iota carrageenans, as well, and to various mixtures of them are successfully utilized. Because the kappa carrageenan produces a gel, whereas the lambda carrageenan does not gel (thickens instead), the firmest gels require a major proportion of the kappa or iota type or mixtures thereof. Since the kappa carrageenan gels most efficiently with potassium ions and the iota carrageenan gels most efficiently with calcium ions, it is desirable to use one or the other carrageenan when potassium ions or calcium ions are present in the toothpaste formulation. Normally, the toothpaste or other cosmetic medium will be at a neutral or alkaline pH, or will be near neutrality, if it is acidic. Acidic pH's, and especially strongly acidic pH's, tend to hydrolyze carrageenan solutions, although when they are in the gelled state, they are generally considered to be stable if in the kappa or iota form (the lambda hydrolyzes and does not gel). The molecular weight of the carrageenans will normally be in the range of 5,000 to about 500,000, with most of those commercially employed being in the range of about 100,000 to 500,000. The gel-sol transition temperatures for the carrageenans vary depending on the particular carrageenan or carrageenan mixture and the composition of the medium in which it is present. Thus, for 1% of kappa carrageenan in water, the gelling temperature can be raised from about 5° C. to as high as 60° C. by increasing the potassium ion content from 0 to about 1%. Similarly, with respect to iota carrageenan, an increase in the calcium ion content from 0 to 1% may increase the gelling temperature from about 44° C. to 72° C. The gelling of kappa carrageenan is usually effected by heating to a temperature of about 70° C. or more, followed by cooling, with a firm gel usually being formed at a temperature between 45° C. and 65° C., which remelts when the temperature is raised 10° C. to 20° C. above the setting temperature. When lambda carrageenan is mixed with kappa carrageenan, it has been found that in the dentifrice compositions described, the gel-sol point may be in the range of 45° C. to 49° C. If this temperature does not result in gel-sol transition, an improvement in viscosity of the product is obtainable by heating it to such a temperature, or higher. An exemplary carrageenan mixture is sold under the brand name Viscarin™ GMC but other commercial products, such as Gelcarin™ HWG, SeaGel™ GH, Gelcarin DG, Gelcarin SI, SeaKem™ 5, Seaspen™ PF, Seaspen™ IN, Gelcarin LMR, Gelcarin MMR, Gelcarin HMR, Gelcarin MAC, Gelcarin MIF, SeaKem C, SeaKem D, SeaKem 9 and SeaKem FL 2, will also be applicable. Such products are available from the Marine Colloids Division of FMC Corporation and more detailed descriptions of such products are found in Monograph No. 1 of Marine Colloids, Inc. and the Technical Bulletin entitled Technical Seminar Notes, published by Marine Colloids Division of the FMC Corporation, Springfield, N.J. 07081.

In the present toothpaste formulations, the proportion of wet minced or co-minced hydrocolloids utilized will usually be in the range of 0.1 to 5% by weight of the total composition. When the wet minced or co-minced hydrocolloids of the present invention is utilized in conjunction with other gelling agents or rheology modifiers, the wet minced and co-minced hydrocolloids will be make up at least 20% of the total of gelling agent present in the toothpaste formulation. The total amount of gelling agent present will be no more than 5% of the toothpaste by weight. Normally, when the wet minced or co-minced hydrocolloids are utilized as the thickening agent, the toothpaste will comprise from about 10 to 70 or 75% of particulate polishing agent, 0.2 to 3% of wet minced or co-minced hydrocolloids, 0.2 to 20% of foaming agent, 2 to 50% of polyhydric alcohol and 5 to 50% of water. Additional adjuvants, if present, will not make up more than 20% by weight in one aspect, no more than 10% by weight in another aspect, and no more than 5% by weight in a further aspect of the toothpaste composition. In some toothpaste preparations it is possible to eliminate the polyhydric alcohol entirely, and in other formulations the water content can be minimized. However, either water or polyhydric alcohol and preferably a mixture of both will be present as the vehicle. Also, for good microwave heating some dielectric material, such as water or other polar and highly dielectric substance should be present. For the purpose of the present invention water is a highly desirable component of the product.

For aqueous toothpaste compositions, the proportions of components are from 40 to 60% by weight of polishing agent, 0.5 to 2% by weight of wet minced or co-minced hydrocolloids (or thickener mixture), 0.2 to 10% by weight of a foaming agent or detergent, 5 to 35% by weight of polyhydric alcohol, and 8 to 30% by weight of water. For gel type dentifrice compositions the proportions may be 10 to 50% by weight of polishing agent, 0.5 to 2% by weight of wet minced or co-minced hydrocolloids, 5 to 15% by weight of a foaming agent or detergent, 30 to 75% by weight of polyhydric alcohol and 10 to 30% by weight of water. Adjuvant content for both toothpaste formulations can range from 0.5 to 5% by weight of the composition, with flavoring agents ranging from 0.5 to 2.5% by weight of the composition. When chloroform is present, as a flavoring means or purge assistant, it may constitute an additional 1 to 5% by weight of the product. Any other adjuvants present will usually not exceed 5% by weight of the total product weight. Methods for the manufacture of the dentifrices of this invention are described in U.S. Pat. Nos. 3,711,604 and 3,840,657. Dentifrices are commonly manufactured by a cold process, e.g., at about 25° C., or by a hot process, e.g., at about 60° C.

Hair Fixatives

The wet minced and co-minced cationic polymers of this invention are suitable additives for the formulation of hair fixative formulations, such as aerosol and non-aerosol hair spray, spritz, gel, spray gel, mousse, styling creams, hair relaxers, and the like. Since the polymers are soluble in water and alcohol mixtures, they are suitable for the formulation of reduced volatile organic compounds (VOC) fixative formulations. The copolymers can be used to prepare 80%, 55%, 30%, or less VOC, and alcohol free formulations.

In particular, the cationic polymers of this invention are designed to provide a combination of long lasting hair style retention at high humidity, natural feel, good hair combing, reduced flaking, no build up, and good hair stylability and restyling. They are good film formers, washable with water and shampoo.

Formulations incorporating the wet minced and co-minced cationic polymers may be delivered from aqueous or hydroalcoholic solutions, dispersions, or emulsions. The polymers can be dissolved in water, water-ethanol or water-solvent mixtures by dispersing the wet minced and co-minced cationic polymers in the solvent and adjusting the pH with an organic or inorganic base between pH 3 and pH 12. An exemplary pH range is 5.0 to 9.0. Within this pH range, water clear solutions of the wet minced and co-minced cationic polymers can be prepared.

In preparing hair styling compositions which incorporate the wet minced and co-minced cationic polymers, the polymer, either in powdered or liquid form, is combined with a solvent system, or with a solvent/propellant system. Preferably, the wet minced and co-minced cationic polymers comprises between about 0.01 to 20% by weight of the total weight of the composition, more preferably between 0.5 to 10% by weight. The solvent system preferably includes water and an organic solvent. Suitable organic solvents include alcohols, glycols and ketones, such as ethanol, isopropanol, acetone, dioxymethane, or methyl ethyl ketone, propylene glycol, hexylene glycol, and butylene glycol. For low VOC compositions, the solvent system includes at least 20 to 50 weight percent water, and optionally up to 100% water. Preferably not more than about 25 weight percent of the organic solvent is used.

The hair styling compositions may be in the form of an aerosol or non-aerosol spray, a mousse, gel, or hair setting lotion. The compositions may contain up to 60 weight percent in one aspect of the invention or up to 35 weight percent of liquefied gases in another aspect. Typical propellants include ethers, compressed gases, halogenated hydrocarbons and hydrocarbons. Exemplary propellants are dimethyl ether, compressed nitrogen, air or carbon dioxide, propane, butane, and 1,1 difluoroethane. Optionally, the solvent can act as the propellant.

The compositions may further include other materials or formulation additives, such as fragrances, preservatives, dyes and other colorants, plasticizers, emulsifiers, conditioners, neutralizers, glossifiers, lubricants, penetrants, UV absorbers, and the like. Mousses, according to the present invention, may further comprise from about 0.25 to 6 weight percent in one aspect, and 0.25 to 3 weight percent by weight in other aspect, of an emulsifier. The emulsifier may be nonionic, cationic, anionic, or amphoteric.

Formulation additives for hair fixatives are those typically used in the formulation of hair, skin and nail products, including conditioning agents such as silicone as previously described.

Another particularly suitable conditioning agent that can be included in the composition of the present invention is a volatile hydrocarbon, such as a hydrocarbon including from about 10 to about 30 carbon atoms, that has sufficient volatility to slowly volatilize from the hair after application of the aerosol or non-aerosol styling aid composition. The volatile hydrocarbons provide essentially the same benefits as the silicone conditioning agents. An exemplary volatile hydrocarbon compound is an aliphatic hydrocarbon including from about 12 to about 24 carbon atoms, and having a boiling point in the range of from about 100° C. to about 300° C. Examples of volatile hydrocarbons useful in the composition of the present invention are the commercially available compounds sold under the brand name PERMETHYL 99A and PERMETHYL 101A, available from Permethyl Corporation, Frazer, Pa. A volatile hydrocarbon compound is useful in the composition of the present invention either alone, in combination with another volatile hydrocarbon, or in combination with a volatile silicone. Examples of other suitable water-insoluble conditioning agents that can be incorporated into the aerosol or non-aerosol aqueous styling aid composition of the present invention include the following: polysiloxane polyether copolymers; polysiloxane polydimethyl dimethylammonium acetate copolymers; acetylated lanolin alcohols; dimethyl dialkyl ammonium chlorides; modified alkyl dimethyl benzyl ammonium chlorides; lauryl dimethylamine oxide; stearyl dimethyl benzyl ammonium chloride; a lanolin-derived extract of sterol on sterol esters; lanolin alcohol concentrate; an isopropyl ester of lanolin fatty acids; sulfur rich amino acid concentrates; isopropyl ester of lanolin fatty acids; stearyl dimethyl benzyl ammonium chloride; cetyl trimethyl ammonium chloride; oleyl dimethyl benzyl ammonium chloride; oleyl alcohol; stearyl alcohol; stearyl dimethyl benzyl ammonium chloride; stearamidopropyl dimethyl myristyl acetate; a polyol fatty acid; a fatty amido amine; guar hydroxypropyltrimonium chloride; cetyl/stearyl alcohol; quaternized protein; keratin protein derivatives; isostearamidopropyl dimethylamine; stearamidopropyl dimethylamine; cetrimonium bromide; myrtrimonium bromide; stearalkonium chloride; cetyl trimethyl ammonium chloride; laurylpyridinium chloride; tris(oligoxyethyl)alkyl ammonium phosphate; an aminofunctional silicone; lapyrium chloride; isopropyl ester of lanolic acids; ethoxylated (30) castor oil; acetylated lanolin alcohol; fatty alcohol fraction of lanolin; a mineral oil and lanolin alcohol mixture; high molecular weight esters of lanolin; quatemium-75; vinylpyrrolidone/dimethylaminoethylmethacrylate copolymer; alkyl trimethyl ammonium chloride; 5 mole ethylene oxide adduct of soya sterol; 10 mole ethylene oxide adduct of soya sterol; stearic acid ester of ethoxylated (20 mole) methyl glucoside; sodium salt of poly-hydroxycarboxylic acid; hydroxylated lanolin; cocamidopropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behenalkonium chloride; behenyl trimethyl ammonium methosulfate and cetearyl alcohol mixture; cetearyl alcohol; isostearamidopropalkonium chloride; linoleamidopropalkonium chloride; oleyl dimethyl benzyl ammonium chloride; tallow imidazolinum methosulfate; stearyl dimethyl benzyl ammonium chloride; stearyl trimonium methosulfate; mixed ethoxylated and propoxylated long chain alcohols; stearamidopropyl dimethylamine lactate; polonitomine oxide; oleamine oxide; stearamine oxide; soya ethyldimonium ethosulfate; hydroxypropyl bislauryldimonium chloride; hydroxypropyl biscetyl-dimonium chloride; hydroxypropyl bisstearyl dimonium chloride; hydroxypropyl bisbehenyl dimonium chloride; ricinolamidopropyl ethyldimonium ethosulfate; olealkonium chloride; stearalkonium chloride; N-(3-isostearamidopropyl)-N,N-dimethyl amino glycolate; N-(3-isostearamidopropyl)-N,N dimethyl amino gluconate; hydrolyzed animal keratin; ethyl hydrolyzed animal keratin; stearyl ammonium chloride; stearamidoethyl diethylamine; cocamidopropyl dimethylamine; lauramidopropyl dimethylamine; oleamidopropyl dimethylamine; palmitamidopropyl dimethylamine; stearamidopropyl dimethylamine lactate; avocado oil; sweet almond oil, grape seed oil; jojoba oil; apricot kernel oil; sesame oil; hybrid safflower oil; wheat germ oil; cocamidoamine lactate; ricinoleamido amine lactate; stearamido amine lactate; stearamido morpholine lactate; isostearamido amine lactate; isostearamido morpholine lactate; wheat germamido dimethylamine lactate; behenamidopropyl betaine; ricinoleamidopropyl betaine; wheat germamidopropyl dimethylamine oxide; disodium isostearaimido MEA sulfosuccinate; disodium oleamide PEG-2 sulfosuccinate; disodium oleamide MEA sulfosuccinate; disodium ricinoleyl MEA sulfosuccinate; disodium wheat germamido MEA sulfosuccinate; disodium wheat germamido PEG-2 sulfosuccinate; stearalkonium chloride; stearly dimethyl benzyl ammonium chloride; stearamido amine; stearamido morpholine; isostearamido amine; isostearamido morpholine; polyethylene glycol (400) mono and distearates; synthetic calcium silicate; isostearic alkanolamide; ethyl esters of hydrolyzed animal protein; blend of cetyl and stearyl alcohols with ethoxylated cetyl or stearyl alcohols; amido amines; polyamido amines; palmityl amido betaine; propoxylated (1 to 20 moles) lanolin alcohols; isostearamide DEA; and hydrolyzed collagen protein. When one or more of these water-insoluble conditioning agents is included in the composition of the present invention in an amount of about 0.5% to about 10% of the total weight of the composition, the composition also can include a suspending agent for the conditioning agent, in an amount of about 0.5% to about 10%, of total weight of the composition. The particular suspending agent is not critical and can be selected from any materials known to suspend water-insoluble liquids in water. Suitable suspending agents are for example, distearyl phthalamic acid; fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCutcheon's Detergents and Emulsifiers, 1989 Annual, published by McCutcheon Division, MC Publishing Co. A nonionic alkanolamide also is optionally included in an amount of about 0.1% to about 5% by weight in the styling aid compositions that include a conditioning agent to provide exceptionally stable emulsification of water-insoluble conditioning agents and to aid in thickening and foam stability. Other useful suspending and thickening agents can be used instead of the alkanolamides such as sodium alginate; guar gum; xanthan gum; gum arabic; cellulose derivatives, such as methylcellulose, hydroxybutylcellulose, hydroxyethylcellulose, hydroxypropylcellulose and carboxymethylcellulose; and various synthetic polymeric thickeners, such as the polyacrylic acid derivatives. Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof.

The propellant gas which is typically included in the aerosol compositions of the present invention can be any liquefiable gas conventionally used for aerosol containers. Examples of materials that are suitable for use as propellants are trichlorofluoromethane; dichlorodifluoromethane, dichlorotetrafluoroethane, monochlorodifluoromethane, trichlorotrifluoroethane, dimethyl ether, propane, n-butane and isobutane, used singly or admixed. Water-soluble gases such as dimethyl ether, carbon dioxide, and/or nitrous oxide also can be used to obtain aerosols having reduced flammability. Water-immiscible, liquefied, hydrocarbon and halogenated hydrocarbon gases such as propane, butane and chlorofluorocarbons can be used advantageously to deliver the contents of the aerosol container without the dramatic pressure drops associated with other immiscible gases. Here there is no concern for the head space to be left inside the aerosol container, because the liquefied gas will sit on top of the aqueous formulation and the pressure inside the container is always the vapor pressure of saturated hydrocarbon vapor. Other insoluble, compressed gases such as nitrogen, helium and fully-fluorinated oxetanes and oxepanes also are useful to deliver the compositions from aerosol containers. Other means of delivery of the above-described aqueous styling aid compositions include, pump sprayers, all forms of bag-in-can devices, in situ carbon dioxide ($CO_2$) generator systems, compressors, and the like. The amount of the propellant gas is governed by normal factors well known in the aerosol art. For mousses, the level of propellant is generally from about 3% to about 30% in one aspect, and from about 5% to about 15% in another aspect, of the total composition. If a propellant such as dimethyl ether utilizes a vapor pressure suppressant (e.g., trichlorethane or dichloromethane), for weight percentage calculations, the amount of suppressant is included as part of the propellant.

The hair styling compositions also can contain a variety of other nonessential, optional components suitable for rendering such compositions more aesthetically acceptable. Such conventional optional ingredients are well known to those skilled in the art, e.g., other emulsifiers such as anionics (e.g., sodium alkyl sulfate); preservatives such as benzyl alcohol, methyl paraben, propyl paraben iodopropenylbutyl carbamate, sodium benzoate, glutaric aldehyde and imidazolidinylurea; cationic emulsifiers/conditioners such as cetyl trimethyl ammonium chloride, stearyldimethyl benzyl ammonium chloride, and di(partially-hydrogenated tallow) dimethylammonium chloride; viscosity modifiers such as a diethanolamide of a long chain fatty acid, fatty alcohols (i.e., cetearyl alcohol), sodium chloride, sodium sulfate, and ethyl alcohol; pH adjusting agents such as citric acid, succinic acid, sodium hydroxide and triethanolamine; coloring agents such as any of the FD&C or D&C dyes; hair oxidizing (bleaching) agents such as hydrogen peroxide, perborate salts and persulfate salts; hair reducing agents such as thioglycolates; perfume oils; chelating agents such as ethylenediaminetetraacetic acid; and, among many other agents, polymer plasticizing agents such as glycerin and propylene glycol. These optional materials are generally used individually at a level of from about 0.01% to about 19% in one aspect, from about 0.5% to about 5% in another aspect, by weight of the total composition. The aqueous formulations of the present invention also can contain conventional hair spray adjuvants in amounts which generally range from about 0.1 to 2% by weight in one aspect, and from about 0.75 to 1% by weight in another aspect, of the total composition. Among the additives which can be employed are plasticizers such as glycols, phthalate esters and glycerine; silicones; emollients; lubricants and penetrants such as various lanolin compounds; protein hydrolysates and other protein derivatives; ethylene adducts and polyoxyethylene cholesterol; dyes, tints and other colorants; and perfumes.

Another additive that may be incorporated into the instant hair compositions is a soluble surface tension reducing compound. It is any soluble compound which reduces the surface tension between the hair styling composition and the gaseous atmosphere above the hairstyling composition. By "gaseous atmosphere" we mean a propellant or air. The soluble surface tension reducing compound may be for example a plasticizer or surfactant in the hair styling composition. The soluble surface tension reducing compound includes for example dimethiconecopolyols, panthenol, fluorosurfactants, glycerin POE, PPG 28 Buteth 35, PEG 75 lanolin, oxtoxynol-9, PEG-25 hydrogenated castor oil, polyethylene glycol 25 glyceryl trioleate, oleth-3 phosphate, PPG-5-ceteth-10 phosphate, PEG-20 methyl glucose ether, or glycereth-7-triacetate, glycereth-7-benzoate or combinations thereof. Preferably, the soluble surface tension compound is dimethiconecopolyols, panthenol, glycereth-7-benzoate, or combinations thereof.

The soluble surface tension reducing compound is typically present in the low beading, low VOC hair styling composition at a concentration of from 0.01 to 1 weight percent in one aspect, and at a concentration of from 0.01 to 0.25 weight percent in another aspect, based on the total weight of the composition.

Also, useful additives are plasticizing compounds. The first class of plasticizing compounds is soluble polycarboxylic acid esters. The polycarboxylic acid esters have a carbon backbone of from 3 to 12 carbon atoms and 3 or more $C_1$ to $C_5$ alkyl carboxylate groups attached thereto. Suitable polycarboxylic acid esters include, for example, triethyl citrate, tributyl citrate, triethyl phthalate, tributyl phthalate, tripentyl phthalate or combinations thereof. Preferably, the polycarboxylic add esters are selected from triethyl citrate, tributyl citrate, tributyl phthalate, or combinations thereof and more preferably are selected from triethyl citrate, tributyl citrate, or combinations thereof. The plasticizing compounds are added to the hair styling composition to provide a total concentration of from 0.01 to 1.0 weight percent plasticizing compounds in one aspect, and from 0.1 to 0.5 weight percent plasticizing compounds in another aspect, based on the total weight of the hair styling composition.

The formulation may optionally contain one or more nonactive adjuvants in an amount up to about 5 wt. % based on the total composition. Such nonactive additives include a corrosion inhibitor, a surfactant, a film hardening agent, a hair curling agent, a coloring agent, a lustrant, a sequestering agent, a preservative and the like. Typical corrosion inhibitors include methylethyl amine borate, methylisopropyl amine borate, Inorganic hydroxides such as ammonium, sodium and potassium hydroxides, nitromethane, dimethyl oxazolidine, 2-dimethylamino-2-methyl-1-propanol, and aminomethyl propanol.

Polar solvents are typically used to prepare the cosmetic or hair compositions. Water, glycols and alcohols are preferably used. The optional alcohol employed in the composition is an aliphatic straight or branched chain monohydric alcohol having 2 to 4 carbon atoms. Exemplary alcohols are isopropanol ethanol. The concentration of the alcohol in the composition should be less than about 40% by weight in one aspect, and surprisingly can be as low as 0% by weight in another aspect. The amount of alcohol typically ranges from 0 to about 30% by weight in one aspect, and from about 5 to about 20% by weight in another aspect, of the total composition.

The hair styling compositions incorporating wet minced and co-minced cationic polymers exhibit desirable characteristics of such compositions, including long lasting hair style retention at high humidity, natural feel, good hair combing, reduced tack, reduced flaking, good stylability and restyling, no fly away, and the like.

A non-aerosol, low VOC, pump hair spray composition is provided herein which is capable of being applied by the user as a fine spray mist, which dries rapidly on the hair, and which provides low curl droop and effective curl retention properties thereon. The composition comprises the wet minced and co-minced cationic polymers of this invention as a hair fixative polymer, and a mixture of alcohol, water and dimethoxymethane (DMM) as cosolvents therefor. Such formulations may be prepared as anhydrous formulas as well or in aqueous media, as hair sprays or as mousse products. For these applications, it is preferable to use lower molecular weight block copolymers and the sprayed droplet sizes should be as small as practical to achieve fast drying of the film. Suitable block copolymers are disclosed in U.S. Pat. No. 6,410,005. The block copolymers of this invention perform substantially better as the conventional fixative polymers because these block copolymers inhibit the curl droop to a greater extent than other polymers used in such formulations. The hair fixative polymer is present at a solids level from about 1 to about 15% by weight, the alcohol in an amount from about 50 to about 70% by weight, water from about 10 to about 30% by weight, and DMM from about 10 to about 30% by weight, all based on the weight of the total composition.

Hard Surface Cleaners

Acidic, neutral and alkaline cleaning compositions have been used for many years for removing soils such as grease, inorganic deposits and stains and the like from hard surfaces and the like. An acidic cleaning composition is also efficient for the removal of limescale deposits from toilet bowls, baths, sinks and taps, provided that such cleaners are kept in physical contact with the soil to be removed for a sufficient period of time. Such deposits generally build up in instances where the water is hard. As calcium and magnesium salt deposits become caked onto these surfaces, they become extremely difficult to remove. Moreover, the surfaces to which such cleaners may be applied are often vertical, inclined or irregularly shaped making it difficult to keep the cleaner in contact with the surface substrate. Low viscosity liquid acidic cleaners may drip and sometimes run from such surfaces when applied. As a result, the liquid acid cleaning composition may not have sufficient contact time and fail to achieve the desired degree of removal of the limestone deposit or other soil.

In an effort to provide a solution to the liquid run-off problem, rheology modifiers have been added to liquid acidic cleaners to thicken and give body to them. Increasing the viscosity of the cleaner enables it to be applied to the surface with reduced dripping and run-off so that the acid cleaner may have longer contact times with the soiled surface being treated cleaned. The rheological properties of the resulting composition must also be such as to enable the cleaner composition to be filled into a bottle, trigger-pack or other suitably convenient container and thereafter to be applied to the soiled surface through the spout, nozzle or spray device that facilitates uniform distribution onto easy, moderate and hard to reach surfaces. The rheological properties must also be such to readily enable rinsing the surface with water or wiping the surface with a sponge or cloth after the cleaning effect has been achieved.

The wet-minced or co-minced hydrocolloids of this invention are useful as a rheology modifier in a wide variety of applications. The galactomannans and polysaccharides suitable for the co-minced process of the present invention have been previously set forth. They will hydrate and dissolve when dispersed in water to produce viscous solutions or gels.

Xanthan gum is well known as a rheology modifier in a wide variety of applications, especially in hard surface cleaners. Co-minced gums comprising xanthan are efficient rheology modifiers for hard surface cleaners. The rheological properties of the xanthan-based co-minced gums of this invention in aqueous compositions, in particular its high degree of pseudoplastic shear-thinning character, make it well suited to applications in acidic cleaners. Under conditions of rest or low shear, an acidic cleaner containing xanthan-based co-minced gums of this invention, exhibits a very high viscosity, thus giving effective surface adherence, resistance to run-off and suspension of any abrasive particles which may be incorporated in the cleaner. Under conditions of high shear, the cleaner exhibits a low viscosity, thus making it easy to fill into and apply from the container and easy to remove from the surface after the cleaning action has taken place.

The amount of co-minced polymer used in the cleaning composition generally ranges from about 0.1 to about 3.0% by weight in one aspect, from about 0.25 to about 1.0% by weight in another aspect, and from about 0.4 to about 0.8% by weight in a further aspect, based on the weight of the total composition.

An acid cleaner and brightener concentrate composition comprising a dicarboxylic acid, an amine and water having a pH of about 1 to about 3 is useful in removal of tenacious soil, such as tarnish, discoloration, corrosion and oxidation products from vehicles, such as railroad rolling stock, without subsequent harm to surfaces, including coated polycarbonate glass substitute.

An effective disinfectant can also be utilized as a component of the composition. This is useful not only to generally disinfect a toilet bowl but is also particularly useful when kept in the vicinity of stains by the viscosity of the solution since the disinfectant then tends to operate effectively to attack and destroy bacteria which are often associated with such stains and which often serve to glue or cement such stains together and protect such stains from the attack of a mineral acid and from scrubbing with an abrasive.

The mineral acid most often used in composition is hydrochloric acid because of its ready availability, low cost and high effectiveness. Other mineral acids, such as, for example, oxalic acid, phosphoric acid, sulfuric acid and the like, can also be used. Generally, at least about 2% by weight of the mineral acid is required to effectively dissolve away the hard water and iron stains. The mineral acid also serves to provide very effective short term disinfectant action. The mineral acid is present in amounts which fall within the range from about 5% to about 12% by weight for home use although higher amounts, e.g., up to 30% by weight are also useful in industrial cleaners. In one aspect, the range of mineral acid concentration is from about 6% to about 10% by weight, based on the weight of the total composition.

The liquid cleaning composition comprises furthermore as essential ingredients one or more detergent active materials which can be anionic, nonionic and zwitterionic type detergent actives or mixtures thereof. Usually anionic synthetic detergents, such as the alkylbenzene sulphonates, alkanesulphonates, alkylsulphates, alkylethersulphates or mixtures thereof can be used. To provide significant cleaning properties to the cleaner composition, it is desirable and in fact necessary, that a non-ionic surfactant be present generally in an amount which falls within the range from about 0.05% to about 5% by weight, based on the weight of the total composition. Any of the common commercial poly(oxyalkylene) alcohols such as those of the non-ionic Triton (alkylphenoxy polyethoxy ethanols as described in "Triton alkylphenoxy surfactants", Rohm and Haas, Philadelphia, 1966) and Pluronic, conforming to the following formula:

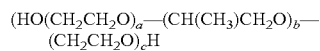

where a, b and c are integers, marketed by BASF Wyandotte Corporation) series are suitable non-ionic surfactants. It is important that the amount of non-ionic surfactant fall within the range from about 0.05% to about 5% by weight, based on the weight of the composition. Triton X-100 and Pluronic P75 both are usable in the cleaner with the Pluronic P75 being preferred because only a single component suspending agent is needed. In one embodiment, the amount of non-ionic surfactant can fall within the range of about 0.1% to about 3% by weight of the composition. It is important that the concentration of the non-ionic surfactant remain within the desired range. If the concentration is too low, insufficient cleaning power will result. If the concentration is too high, the viscosity of the cleaner will be deleteriously affected. With a highly effective surfactant, such as Pluronic P75, the amount of surfactant ranges from about 0.1% to about 0.5% by weight of the total composition. With somewhat less effective surfactant, such as Triton X-100, the use of about 2% by weight is desirable, based on the weight of the composition.

An abrasive agent must be present and suspended in the cleaner in an amount within the range from about 2% to about 40% by weight of the composition. In another embodiment, the abrasive agent will be present in an amount which falls within the range from about 5% to about 25% by weight in one aspect, and from about 5% to about 15% by weight in another aspect, based on the total weight of the composition. Any suitable acid stable abrasive agent may be used, although sand is preferred because of its ready availability and low cost. Generally, the abrasive agent should be present in a particle size within the range from about 40 to about 400 mesh (corresponding to a mesh aperture size of 420 μm to 37 μm). In another embodiment, the mesh size is 140 to 200 mesh (105 μm to 74 μm). When the particles are in the 100 to 400 mesh (150 μm to 37 μm) size range, they can be readily suspended into a homogeneous stable liquid dispersion, yet they are large enough to provide adequate scouring properties. Other abrasive agents such as, for example, kaolin, pumice, diatomite, tripoli, siliceous clay, feldspar, etc. may be partially or completely substituted for the sand. The amount of the abrasive agent should not be less than about 2% by weight of the composition or sufficient abrasive properties will not result, and the concentration should not be greater than about 40% by weight of the composition or difficulty will result in obtaining a homogeneous and stable liquid dispersion. Generally, the abrasive agent should have a Mohs Hardness value within the range from about 2 to about 7. Softer abrasive agents are only partially effective and harder abrasive agents may damage porcelain surfaces of toilet bowls, sinks, and the like. With abrasives having a Mohs Hardness of 2 to 3, the particle size should be larger than about 250 micrometers (60 mesh) and with abrasives having a Mohs Hardness above about 5.5 (which are hard enough to scratch porcelain) the particle size should be no larger than 100 micrometers and preferably no larger than about 50 micrometers (270 mesh).

An effective disinfectant should preferably be present in an amount within the range from about 0.05% to about 8% by weight of the composition. An exemplary disinfectant is a quaternary ammonium compound although other compatible disinfectants as well can be utilized. Preferably, the disinfectants should be present in an amount within a range from about 0.5% to about 5% by weight of the composition if it is a quaternary ammonium compound. Any of a number of quaternary ammonium compounds can be used. One particularly preferred quaternary ammonium compound comprises a commercially available mixture of octyidecyldimethylammonium chloride, dioctyldimethylammonium chloride and didecyldimethylammonium chloride with the trademark BARDAC-20 marketed by Lonza, Inc, and described in "BARQUAT and BARDAC Quaternary Ammonium Compounds", L-40, Fair Lawn, 1973. Rohm and Haas Company markets a useful quaternary ammonium compound under the trademark Hyamine 3500 and Onyx Chemical Company markets another such compound under the trademark BTC 2125M. Both of these compounds are of the benzyl alkyl ammonium cation type. Useful phenolic disinfectants include 2,2'-methylenebis (4-chlorophenol) and its water-soluble salts in concentrations of 0.05% to 1%. This compound is available under the Preventol trademark from General Aniline & Film Corporation and is described in "Preventol GD and Preventol GDC", Technical Bulletin 7543-065, General Aniline & Film Corporation, 1966.

A particular suspending agent can be used in the composition. The suspending agent must comprise at least about 0.5% hydrophilic silica. Preferably, the amount of hydrophilic silica falls within the range from about 1% to about 5%. Hydrophilic silica is a relatively low bulk density particulate powdery material capable of forming hydrogen bonds with water when dissolved therein. Generally, the hydrophilic silica will have a large surface area, usually of at least 100 m²/gram in one aspect, from 100 m²/gram to 500 m²/gram in another aspect, and from about 150 m²/gram to about 250 m²/gram in a further aspect. Commercially available fumed silica, made by decomposing $SiCl_4$ in the presence of water vapor (such as a product sold under the trademark Cabosil M-5 by Cabot Corporation, Boston, Mass.) is an especially useful form of hydrophilic silica. Hydrophilic silica of suitable properties can also be made by careful precipitation of silica from solution. Precipitated hydrophilic silica is available commercially, for example, from Philadelphia Quartz Company and is sold under the trademark QUSO. Further description of this type of hydrophilic silica and its preparation is found in U.S. Pat. No. 3,208,823. When sufficient quantities of hydrophilic silica are dissolved in a water solution a thixotropic gel will result. The amount of hydrophilic silica used in the cleaner of the present invention is always kept below that which would cause the formation of a thixotropic gel. This is useful to insure that the cleaner will have adequate free-flowing characteristics without the necessity for agitating it to temporarily break a gel.

The hydrophilic silica must in some cases be used in combination with at least about 0.01% of a co-suspending agent consisting of the co-minced hydrocolloids of this invention.

As previously mentioned, it has been found that with some non-ionic surfactants, e.g., with Triton X-100 a co-suspending agent is needed while with other non-ionic surfactants, e.g., Pluronic P75 a co-suspending agent Is not needed. This can be very simply tested for particular non-ionic surfactants by simply making up a cleaner solution of the present invention without a co-suspending agent and noting whether the abrasive agent remains suspended therein without gelling thereof. If not, a co-suspending agent is used in conjunction with the hydrophilic silica.

Sufficient of the suspending agent is used to keep the abrasive suspended and to make the cleaner free-flowing so it can readily be poured or squirted out of a bottle or the like but still be viscous enough to adhere to a smooth surface and to stains.

The remainder of the composition, generally at least about 25% beyond that present in the acid, is water although various adjuvants, odors and the like may be added as is well known in the art. A dye may very advantageously be added to the cleaner in sufficient quantity to impart a color thereto. With the particular cleaner of the present invention, the color serves a very distinct purpose other than simply making the cleaner more aesthetically pleasing. In particular, the color indicates what portions of the bowl, for example, adjacent stains, the cleaner has adhered to. Because of the adherent properties of the cleaner, the person making use of it then knows whether each portion of the stains within the bowl have sufficient, but not excess, cleaner adjacent them so that they can be effectively scrubbed.

In order to obtain a homogeneous stable liquid dispersion the order of mixing of the ingredients of the cleaner is important. In particular, it is necessary that the suspending agent be dispersed in the water prior to the mixing of the abrasive therewith and that the abrasive be added with sufficient agitation to lead to the formation of a stable homogeneous dispersion. If this is not done, the abrasive will settle out of solution and a homogeneous liquid dispersion will not result. The other components of the cleaner are then admixed with the resulting stable homogeneous dispersion.

Food Applications

The polygalactomannan hydrocolloids of the present invention may be used alone, in combination with each other and/or or with other gums such as locust bean gum, carrageenan, xanthan or tara gum, starch or gelatin In a wide variety of food products, including pet-foods, such as wet pet-food. The product may be derivatized where food acceptable substituents are employed. The compositions may employ food acceptable salts of mono-, di- or trivalent cations, preservatives such as sodium benzoate, citric acid or sorbic acid, or ion sequestering agent such as citric, tartaric or orthophosphoric acids. The product may be dried and stored then, when converted to gel or sol form by hydration in cold or warm water systems, the thixotropic viscous colloidal dispersion thus formed may be used directly in food compositions. The viscosity developed is somewhat shear sensitive at low concentration and is dependent on temperature, concentration, pH, ionic strength as well as the induced agitation. Viscosities may be measured by a rotational, shear type viscometer capillary viscometer at low concentrations and extrusion rheometers at higher concentrations. Typically, viscosity is measured by a Brookfield RVT Viscometer (Brookfield Engineering Laboratories, Stoughton, Mass. 02072) at 20 rpm using spindle 3.

The food products contemplated for use with the polygalactomannan hydrocolloids according to the present invention are selected from the groups of baked goods and baking mixes, including all ready-to-eat and ready-to-bake products, flours, and mixes requiring preparation before serving; beverages, alcoholic, including malt beverages, wines, distilled liquors, and cocktail mix; beverages and beverage bases, non-alcoholic, including only special or spiced teas, soft drinks, coffee substitutes, and fruit and vegetable flavored gelatin drinks; breakfast cereals; including ready-to-eat and instant and regular hot cereals; cheeses, including curd and whey cheeses, cream, natural, grating, processed, spread, dip, and miscellaneous cheeses; chewing gum, including all forms; coffee and tea, including regular, decaffeinated, and instant types; condiments and relishes, including plain seasoning sauces and spreads, olives, pickles, and relishes, but not spices or herbs; confections and frostings, including candy and flavored frostings, marshmallows, baking chocolate, and brown, lump, rock, maple, powdered, and raw sugars; dairy product analogs, including non-dairy milk, frozen or liquid creamers, coffee whiteners, toppings, and other non-dairy products; egg products, including liquid, frozen, or dried eggs, and egg dishes made therefrom, i.e., egg roll, egg foo young, egg salad, and frozen multi-course egg meals, but not fresh eggs; fats and oils, including margarine, dressings for salads, butter, salad oils, shortenings and cooking oils; fish products, including all prepared main dishes, salads, appetizers, frozen multi-course meals, and spreads containing fish, shellfish, and other aquatic animals, but not fresh fish; fresh eggs, including cooked eggs and egg dishes made only from fresh shell eggs; fresh fish, including only fresh and frozen fish, shellfish, and other aquatic animals; fresh fruits and fruit juices, including only raw fruits, citrus, melons, and berries, and home-prepared "ades" and punches made therefrom; fresh meats, including only fresh or home-frozen beef or veal, pork, lamb or mutton and home-prepared fresh meat-containing dishes, salads, appetizers, or sandwich spreads made therefrom; fresh poultry, including only fresh or home-frozen poultry and game birds and home-prepared fresh poultry-containing dishes, salads, appetizers, or sandwich spreads made therefrom; fresh vegetables, tomatoes, and potatoes, including only fresh and home-prepared vegetables; frozen dairy desserts and mixes, including ice cream, ice milks, sherbets, and other frozen dairy desserts and specialties; fruit and water ices, including all frozen fruit and water ices; gelatins, puddings, and fillings, including flavored gelatin desserts, puddings, custards, parfaits, pie fillings, and gelatin base salads; grain products and pastas, including macaroni and noodle products, rice dishes, and frozen multi-course meals, without meat or vegetables; gravies and sauces, Including all meat sauces and gravies, and tomato, milk, buttery, and specialty sauces; hard candy and cough drops, including all hard type candies; herbs, seeds, spices, seasonings, blends, extracts, and flavorings, including all natural and artificial spices, blends, and flavors; jams and jellies, home-prepared, including only home-prepared jams, jellies, fruit butters, preserves, and sweet spreads; jams and jellies, commercial, including only commercially processed jams, jellies, fruit butters, preserves, and sweet spreads; meat products, including all meats and meat containing dishes, salads, appetizers, frozen multi-course meat meals, and sandwich ingredients prepared by commercial processing or using commercially processed meats with home preparation; milk, whole and skim, Including only whole, low-fat, and skim fluid milks; milk products, including flavored milks and milk drinks, dry milks, toppings, snack dips, spreads, weight control milk beverages, and other milk origin products; nuts and nut products, including whole or shelled tree nuts, peanuts, coconut, and nut and peanut spreads; plant protein products, including the National Academy of Sciences/National Research Council "reconstituted vegetable protein" category, and meat, poultry, and fish substitutes, analogs, and extender products made from plant proteins; poultry products, including all poultry and poultry-containing dishes, salads, appetizers, frozen multi-course poultry meals, and sandwich ingredients prepared by commercial processing or using commercially processed poultry with home preparation; processed fruits and fruit juices, including all commercially processed fruits, citrus, berries, and mixtures; salads, juices and juice punches, concentrates, dilutions, "ades", and drink substitutes made therefrom; processed vegetables and vegetable juices, including all commercially processed vegetables, vegetable dishes, frozen multi-course vegetable meals, and vegetable juices and blends; snack foods, including chips, pretzels, and other novelty snacks; soft candy, including candy bars, chocolates, fudge, mints, and other chewy or nougat candies; soups, home-prepared, including meat, fish, poultry, vegetable, and combination home-prepared soups; soups and soup mixes, including commercially prepared meat, fish, poultry, vegetable, and combination soups and soup mixes; sugar substitutes, including granulated, liquid, and tablet sugar substitutes; and sweet sauces, toppings, and syrups, including chocolate, berry, fruit, corn syrup, and maple sweet sauces and toppings. As mentioned above, the galactomannan hydrocolloids according to this invention can be added to meat and ground meat such as for making sausages and, for instance, hamburger patties without negatively imparting taste and mouth feel.

Accordingly, the present invention is also directed to food and fodder compositions comprising the polygalactomannan hydrocolloids of the present invention. The amount of polygalactomannan hydrocolloid in the food/fodder composition depends on the type of food/fodder.

EXAMPLES

The following examples are for illustrative purposes and are not intended to limit the invention in any way. The invention has been described herein in considerable detail in order to comply with the Patent Statutes and to provide those skilled in the art with the information needed to apply the novel principles of the present invention. However, it is to be understood that the invention may be carried out by different equipment, and devices and that various modifications, both as to the starting materials, equipment details and operating procedures, may be accomplished without departing from the true spirit and scope of the claimed invention.

Procedures

Starting materials (if not otherwise specified):

(a) *cassia*: commercially available raw *cassia* tora/obtusifolia split (gum), fat content about 1.5%, protein content about 7%, ash content 1.3%, chrysophanol content of 9.5 ppm (HPLC)

(b) locust bean: commercially available raw locust bean split (gum), fat content about 1.3%, protein content about 7%, ash content 1.2%

(c) tara: commercially available raw tara split (gum), fat content about 1.4%, protein content about 8%, ash content 1.2%

(d) guar: commercially available raw guar split (gum), fat content about 1.1%, protein content about 10%, ash content 1.5%

(e) carrageenan: standard semi-refined carrageenan, Danagel PF 8263 from FMC GmbH, Frankfurt, Germany Meat mincer: electrical meat mincer, commercially available from Jupiter, Germany, designation 885, 320 watt Measurement Methods:

The measurement methods described herein below are exemplary.

1% Viscosity

To 396 g of distilled water are added 4 g of the 4.00 g powdered hydrocolloid sample (particle size <250 µm) at room temperature and stirred at about 700 rpm. In case of lump formation the test has to be repeated.

Cold Viscosity $v^2_{20}$

The hydrocolloid is stirred for 30 minutes at room temperature (20° C.) and kept for an additional hour at a temperature of 20° C. The viscosity is measured by using a Brookfield RVT Digital Viscometer at a speed of 20 rpm. The suitable RVT Brookfield spindle depends on the viscosity.

Hot Viscosity $v^{90}_{20}$

The hydrocolloid is stirred for 30 minutes at room temperature and heated in a hot water bath to 90° C. After cooling to between 60 to 70° C., the loss of water is compensated and the solution is kept at a temperature of 20° C. for another hour. The viscosity is measured by using a Brookfield Digital Viscometer, at a speed of 20 rpm. The suitable RVT Brookfield spindle depends on the viscosity.

Break Strength Gel Testing

Standard Method 5 g of KCl are dissolved in 985 g of distilled water at room temperature. 10 g of hydrocolloid(s) are added to the stirred solution and stirring is continued for additional 5 minutes. The stirred mixture is heated in a hot water bath to 90° C. After cooling to 70 to 75° C., the loss of water is compensated. The solution is filled in cubic jelly boxes (5.0×5.0×5.0 cm) and covered by a PE film. The jelly boxes are allowed to stand undisturbed for at least 3 hours at room temperature. Thereafter, the boxes are stored in an incubator at 20° C. for at least one more hour.

Gel testing is carried out with a texture analyzer from Stable Micro Systems, type TA XT2. Conditions: cylindrical stamp with 1.00 cm² bottom surface, speed: 1 mm/sec, distance: 15 mm. The break strength is obtained in gram, the gel deformation is obtained in mm and the slope is obtained in g/mm.

Retorting 5 g of KCl are dissolved in 985 g of distilled water at room temperature. 10 g hydrocolloid(s) are added to the stirred solution and stirring is continued for 15 minutes. The stirred mixture is heated in a hot water bath to 90° C. After cooling to 70 to 75° C., the loss of water is compensated. The solution is filled in cans, sealed and retorted at 129° C. for 1 hour. After cooling to 70 to 75° C., the cans can be opened. The solution is filled in cubic jelly boxes (5.0×5.0×5.0 cm) and covered by a PE film. The jelly boxes are allowed to stand undisturbed for at least 3 hours at room temperature (20° C.). Thereafter, they are stored in an incubator at 20° C. for at least one more hour. Testing as described in 2.1.

Gel Strength

Principle

*Cassia* gum is forming a gel with carrageenan in a phosphate buffer in the presence of potassium chloride. The resistance of this gel to rupture is measured on the FIRA jelly tester by an immersed paddle (6.54 cm²=1 in²), which is rotated by 300.

Definition

The gel strength is defined as the weight of grams of water required to give a 30° deflection on the FIRA jelly tester (from H. A. Gaydon & Co Ltd, Clyde Works; Clyde Road, Wallington, Surrey SM6 8PZ, United Kingdom).

Buffer solution (pH=6.60): 8 g of sodium dihydrogen phosphate dihydrate ($NaH_2PO_4 \times 2H_2O$), 5 g of anhydrous disodium hydrogen phosphate ($Na_2HPO_4$), and 3 g of anhydrous potassium chloride (KCl) are added into a 1,000 ml measuring flask, distilled/de-ionized water is added to dissolve the salts, the flask is filled with said water to 1,000 ml and the pH is checked (pH=6.60±0.05).

Making the Jelly Solution 497 g of the buffer solution (pH=6.60) are placed into a 1,000 ml beaker equipped with a magnetic stirrer, and a magnetic stirring bar. 1.50 g of the sample to be tested (for instance, Diagum CS) and 1.50 g standard carrageenan are slowly added together into the cold stirred buffer solution. The total weight total weight [beaker+magnetic stirring bar+buffer solution+gel powder] is the determined. Subsequently, the temperature of the stirred solution is raised to the boiling point (about 95 to 100° C.) and said temperature is maintained for 5 minutes. The beaker is removed from the heating unit and placed on a cold stirrer and stirred for 5 minutes at room temperature. The beaker is then placed on a scale and filled up to total weight with cold distilled water to compensate for loss on evaporation. The test solution is the stirred for one minute and poured into 3 jelly boxes while still hot. The jelly boxes are allowed to stand undisturbed for at least 4 hours at room temperature (or in any event below 30° C.). Then, the jelly boxes are placed In an incubator at 20±0.1° C. for another 1 hour. The gel is then ready for gel-strength measurement.

Gel Testing

Place FIRA jelly tester bucket on balance and re-set the tara weight; attach bucket on FIRA jelly tester and counterpoise. Set scale to zero with the damping brake on SET ZERO. Place jelly box on the FIRA jelly tester, raise platform until paddle penetrates the jelly as far as the lower mark on the shaft of the paddle. Release damping brake from SET ZERO to TEST. Depress water valve key and allow water to flow into bucket, stop water flow into bucket immediately when scale passes the 30° deflection. Detach bucket from tester and place on balance. Note weight of water. The measuring result obtained is the gel strength that equals the weight of water in gram.

Cryogenic Scanning Electron Microscopy

The morphology of various samples is observed by Cryogenic Scanning Electron Miscroscopy (CryoSEM) using a LEO 435VP scanning electron microscope with an Oxford CT1500 cryotransfer stage. The general procedure consists of preparing a 1 wt. % homogeneous dispersion of sample material in deionized water in a glass vial. A portion of the sample is removed from the vial using the bare stick end of a cotton swab and is placed onto a sample carrier that is mounted in the CryoSEM sample holder. The sample carrier is a cylinder having a bore, a closed end and an open end. The sample carrier is mounted in the sample holder so that the open end is facing upward. The sample is placed on the open end of the sample carrier so that a stable droplet is formed on the sample carrier. If the droplet flows into the sample carrier bore, subsequent attempts to form a stable droplet on the carrier are attempted. An inverted sample carrier (open end facing downward) is then placed on the sample carrier holding the sample droplet to form a carrier/droplet/carrier assembly. The sample is prefrozen by plunging the CryoSEM carrier/droplet/carrier holder assembly into an 8 oz. blown foam styrene cup that is ½ filled with liquid nitrogen ($LN_2$) at about −195° C. for 2 to 5 seconds. The entire assembly is then transferred to a bath at about −195° C. containing a mixture $LN_2$ and frozen $N_2$. The holder assembly with sample is plunged into the bath and immediately removed. The holder assembly is placed under vacuum in a vacuum chamber to completely freeze the sample. Upon freezing, the vacuum chamber is vented and the sample holder assembly is transferred to the CryoSEM prep chamber. Once in the prep chamber, the carrier/droplet/carrier assembly is broken apart using a remote probe to fracture the frozen droplet (known as "freeze fracture"). The CryoSEM sample holder with the newly fractured sample is transferred into the CryoSEM prep chamber which is under vacuum and held at a temperature ranging from −140° C. to −120° C. The sample is removed from the CryoSEM prep chamber and placed on the sample stage of the CryoSEM and observed with the accelerating voltage of the SEM varying between 15 and 20 kilovolts. The sample stage temperature is maintained at the desired temperature by the addition of $LN_2$ to the cryogen circulating system. The sample is etched by heating the sample stage to −95° C. to sublime off water in the sample. The length of the etch process is dependent upon the amount of sample present and how well-bound the water is. For the samples described in this invention, the time varied between 2 and 10 minutes. Upon completion of the etch process, the stage heater is turned off and the stage is allowed to cool back to −120° C. or below. The sample is placed back in the cryoprep chamber (still under vacuum and at about −130° C. or lower) for metallization. The sample is sputter coated with Au/Pd metal for 2 minutes to render it conductive to the electron beam. Once coated, the sample is observed via the SEM and imaged. The images are captured at various magnifications depending upon the sample uniformity and the feature size.

Clarity

Sample clarity is measured in percentage of transmittance at 420 nm with a Brinkman PC920 colorimeter. A dry sample cuvette of the calorimeter is completely filled by the test sample. The cuvette is placed in the instrument and the lowest reading (displayed percentage transmittance number) is recorded.

Turbidity

Turbidity is represented by the absence of clarity in a liquid due to suspended solids. The turbidity of a sample is measured with a turbidimeter (DRT 100B available from HF Instruments) and is measured in nephelometric turbidity units (NTU). A dry sample curvette of the turbidimeter is completely filled by the test sample. The curvette is placed in the instrument and the lowest displayed reading is recorded.

Gel Properties by Texture Analyzer

The gel properties are measured by a texture analyzer from Stable Micro Systems, type TA XT2i. A cylindrical stamp with 258 $mm^2$ (0.4 $in^2$) bottom surface penetrated the gel at a speed of 1 mm/s for a set depth distance of 15 mm. Cylindrical shaped gel samples of 45 mm in height and 50 mm in diameter were tested [gels prepared in a 56.7 g (2 ounce) jar available from Parkway]. The typical curves as represented by FIG. 9 are obtained.

The break strength is obtained in grams and represents the maximum force for the tip of the cylindrical stamp to penetrate the gel initially before it breaks, the gel rigidity (in g/s or g/mm) is measured by the slope of the curve before the gel breaks, and the work to penetrate the gel, that is an indirect measure of the inner gel strength (in g·s or g·mm) is measured by the area under the curve at the maximum force.

Foam Height

Foam height is measured by the following method by weighing 1 g of a formulated sample with 85 g of de-ionized water into a 100 ml beaker. The system is mixed for 3 minutes and then poured slowly into a 500 ml graduated cylinder. Additional de-ionized water is used to bring the water level to 100 ml. The cylinder is then capped tightly and, with arms extended, the cylinder is rotated 180 degrees five consecutive times. The foam height is measured by avoiding inclusion of large spacious single bubble on top and minus the 100 ml initial mixture volume.

General Procedures

One part of the respective *cassia*, locust bean, tara or guar split (raw endosperm flour) is rinsed on a 0.5 mm screen with water for about one minute. Thereafter, the split is weighed and transferred into a beaker and water is added so that the ratio of split to water is 1 to 2.5. After some minutes, the water has completely been absorbed by the split. Subsequently, the wet split is passed three times through a conventional meat mincer by using perforations which are reduced in every step from 3 mm (start) to 2 mm and in the final mincing step 1 mm. The thusly processed wet raw mass is introduced in a 50:50 iso-propanol/water mixture (50% iso-propanol) by means of an Ultraturrax. After stirring for some minutes, the solids are separated from the alcohol/water mixture by filtration. The solids isolated are washed for a second time by introducing the solids into an iso-propanol/water mixture containing 70% by weight of Iso-propanol. The solids are again filtered off and isolated and washed with iso-propanol/water mixture containing 85% by weight of iso-propanol. After filtration, the solid representing the respective hydrocolloid is isolated and carefully dried. The filtrate of each individual step is discarded. The yield generally was between 90 and 95%. The hydrocolloids obtained were tested as to their viscosity, gel and break strength, transparency, and turbidity.

For making derivatized/modified polygalactomannans the derivatization agent is already present in the aqueous swelling solution in the swelling step. Preferably, depending on the derivatizing agent, a water/organic solvent mixture is used in the swelling step. Furthermore, depending on the derivatizing agent it may be suitable to adjust the pH of the swelling medium to an alkaline pH, for instance, by the addition of potassium hydroxide. The amount of alkali and derivatizing agent added depends on the degree of substitution to be achieved. Thus, more potassium hydroxide and derivatizing agent is used if the degree of substitution is to be increased, and vice versa. Likewise, it may be advantageous to increase the reaction time and temperature in order to drive the reaction to completion. After the reaction is complete, depending on the pH, it might be necessary to adjust the pH to neutral or slightly alkaline by adding a suitable amount of, for instance, hydrochloric acid. The work up which follows is as described above.

The derivatization of *cassia* with 2,3-epoxypropyltrimethyl ammonium chloride (also called glycidyltrimethylammonium chloride is available as Quab® 151 from Degussa AG, Germany) is carried out in an alkaline (KOH) water/isopropanol mixture. The reaction temperature can be raised to 70° C., the reaction time is about 3 hours. Neutralization with hydrochloric acid (10%) to a pH of about 8.5 prior to filtering, washing, drying and milling has proven advantageous. Exemplary degrees of substitution are 0.64 and 0.91.

If not otherwise stated in the examples which follow, the cationic *cassia* according to the invention is *cassia* derivatized with 2,3-epoxypropyltrimethyl ammonium chloride and having a degree of substitution of 0.64 that has been prepared according to the method described above.

Cationization or cationic charge density is often measured by the degree of substitution. The term "degree of substitution" as employed herein is the average substitution of functional groups per anhydro sugar unit in the polygalactomannan gum. In guar gum, the basic unit of the polymer consists of two mannose units with a glycosidic linkage and a galactose unit attached to the C6 hydroxyl group of one of the mannose units. In *cassia* gum, the basic unit of the polymer consists of five mannose units with a glycosidic linkage and a galactose unit attached to the C6 hydroxyl group of one of the mannose units. On the average, each of the anhydro sugar units contains three available hydroxyl sites. A degree of substitution of three would mean that all of the available hydroxyl sites have been esterified with functional groups. The degree of substitution is expressed as moles of cationic reagent per anhydro sugar units and can be then calculated from the following formula:

$$\text{Degree of substitution} = \frac{\% \text{ Nitrogen} \times 162.15}{(1401 - \% \text{ Nitrogen} \times 151.62)}$$

Molecular weight of the anhydro sugar units: 162.15 g/mol

Molecular weight of cationic substituent: 151.62 g/mol

The nitrogen content was measured by elemental analysis of the cationic substituent 2-hydroxypropyltrimethylammonium chloride.

| Sample | Composition | Nitrogen Content (wt. %) | Degree of Substitution |
|---|---|---|---|
| A | Cationic *Cassia* | 4.25 | 0.91 |
| B | Cationic *Cassia* | 4.14 | 0.87 |
| C | Cationic *Cassia* | 3.78 | 0.74 |
| D | Cationic *Cassia* | 3.45 | 0.64 |
| E | Cationic *Cassia* | 2.43 | 0.38 |
| F | Cationic Guar | 4.05 | 0.83 |

-continued

| Sample | Composition | Nitrogen Content (wt. %) | Degree of Substitution |
|---|---|---|---|
| G | Cationic *Cassia*/Cationic Guar 50/50 | 1.85 | 0.27 |
| Jaguar ™ Excel | Cationic Guar | 1.37 | 0.19 |
| Jaguar ™ C13S | Cationic Guar | 1.37 | 0.19 |

Example 1

Following the general procedure of the present invention one part of *cassia* split (endosperm flour of *cassia*) having an original chrysophanol content of 9.5 ppm (as determined by HPLC) was processed. The level of chrysophanol in the hydrocolloid obtained has been determined by HPLC to be less than 1 ppm.

In a comparative experiment following the conditions described in U.S. Pat. No. 4,840,811 starting from the same *cassia* split the anthraquinone level was only reduced by 50%, even after several washings.

Example 2

Split of *cassia* was milled using traditional milling technology to a powder having a particle size of less than 250 µm. The product obtained will be designated "Diagum™ CS *cassia* standard".

The same raw *cassia* split was swollen with water in a ratio of *cassia* split:water is 1:3. Subsequently, the swollen material was minced and homogenized using a commercially available meat mincer. The still moist product was dried, sieved and particles having a particle size >250 µm were subjected to a further grinding step.

The gel of the *cassia* prepared as above, 2.60 g of kappa-carrageenan (Danagel PF8263) and 250 g potassium chloride were dry mixed and thereafter added to 192.5 g of water. The suspension was heated in a water bath at 90° C. while stirring. The solution obtained was poured into a can. After cooling to about 70° C., the loss of water was compensated. The solution is poured into the above mentioned cubic jelly boxes and were allowed to stand for 4 hours at 20° C.

In order to determine the heat stability of the product, the solution was kept in an autoclave at 129° C. for 60 minutes (retorting) in order to simulate the manufacturing conditions of a food can. After cooling to 70° C., it was continued as above described. The results are summarized in the following Table:

| | Break Strength (g/cm$^2$) Before Retorting | Break Strength (g/cm$^2$) After Retorting |
|---|---|---|
| Diagum ™ CS *Cassia* Standard | 1103.1 | 654.2 |
| Wet Minced *Cassia* | 1360.4 | 1158.5 |

Example 3

In the following experiment, it is demonstrated that if the splits of different hydrocolloids are wet processed together according to the method of the present invention the galactomannan hydrocolloid (blend) has better performance characteristics compared to a mixture of the mixed galactomannan hydrocolloids.

a) *Cassia* hydrocolloid was prepared according to the method described above. The powderous *cassia* hydrocolloid was dry mixed with kappa-carrageenan (Danagel PF8263) in various ratios and KCl and the performance of said blend was measured.

b) Mixtures of *cassia* split and carrageenan of various ratios were swollen with water in a weight ratio of 1:3, mixed and subsequently minced together in a meat mincer. The mincing step was repeated 5 times. The product obtained was further processed as described above and the performance of said coprocessed system was determined. In all cases, the gel consists of 1% hydrocolloid (galactomannan hydrocolloid and carrageenan), 0.5% KCl and 98.5% by weight of water. The results are summarized in the following Table:

| Ratio* | Break Strength (g/cm$^2$) Without Retorting | | Break Strength (g/cm$^2$) With Retorting** | |
|---|---|---|---|---|
| | Blend | Coprocessed | Blend | Coprocessed |
| 40:60 | 860 | 1163 | 735 | 1120 |
| 50:50 | 971 | 1194 | 800 | 1198 |
| 60:40 | 1090 | 1198 | 996 | 1149 |

*ratio by weight of *cassia* hydrocolloid:carrageenan
**autoclaved for 1 hour at 129° C.

As is evident from the above Table, higher break strengths are obtained for the gels if prepared accordingly to the present invention.

It has further been found that the time and temperature necessary to completely hydrate the *cassia*/carrageenan blends is at least 80° C. for 10 minutes in order to achieve the maximum gel strength. Identical systems which are made according to the method of the present invention (coprocesses systems) need much less time and lower temperatures to achieve the maximum gel strength. Thus, the hydration temperature can be lowered by at least 10° C.

Example 4

The following Table demonstrates the synergistic effect of selected hydrocolloids of the invention on the gel strength and break strength of carrageenan gels.

| Gel* | Gel Strength (g) | Break Strength (g/cm$^2$) |
|---|---|---|
| 1% Carrageenan | 105 | 423 |
| 0.5% Carrageenan 0.5% Tara | 141 | 408 |
| 0.5% Carrageenan 0.5% Locust Bean | 206 | 743 |
| 0.5% Carrageenan 0.5% Cassia | 251 | 1130 |

*The gel contains (by weight) 0.5% KCl, 98.5% water and 1% of the carrageenan or carrageenan/hydrocolloid As is evident, replacing a part of the carrageenan with a corresponding part of a galactomannan hydrocolloid of the invention significantly improves both the gel strength and the break strength.

Example 5

The hot and cold water viscosity values of co-minced blends of *cassia* and guar hydrocolloids prepared by the process of the invention are compared to conventional blends of individually minced *cassia* and guar.

*Cassia* and guar splits are individually soaked in a three-fold amount of water (w/w) until fully hydrated. Various weight percentages (see FIG. 1) of the hydrated *cassia* and guar splits are blended together and co-minced on a meat grinder (Jupiter Model 885). The co-blends are processed 3 times on the mincer through a 3 mm perforated disk followed by 3 repetitions utilizing a 2 mm perforated disk. For comparative purposes, samples of the hydrated *cassia* and guar splits are individually minced on the same meat mincer. The individually minced *cassia* and guar splits are conventionally blended in the same weight percentages as the co-minced *cassia*/guar blends. One weight % aqueous dispersions of the co-minced *cassia*/guar blend (System) and the individually minced *cassia*/guar conventional blends (Blend) are evaluated for cold and hot viscosity properties and plotted.

A plot comparing the cold and hot viscosity values of co-minced *cassia*/guar blends and individually minced *cassia* and guar which are blended by conventional mixing is shown in FIG. 1. Equations and $R^2$ values for the plotted curves are as follows:

Hot Viscosity System $y=74.036x^3+610.39x^2-4100.3x+3480$ $R^2=0.987$

Hot Viscosity Blend $y=991.99x^3+1437.4x^2-5783.6x+3480$ $R^2=0.990$

Cold Viscosity System $y=-939.91x^3+3038.5x^2-4288.3x+2260$ $R^2=0.998$

Cold Viscosity Blend $y=-5816.3x^3+12557x^2-8958.6x+2260$ $R^2=0.989$

As shown in the plot in FIG. 1, the cold and hot viscosity of co-minced *cassia*/guar gum (Systems) is significantly higher than blends of individually minced *cassia* and guar (Blends). The curves for the cold water solubility show that co-minced *cassia*/guar Systems have much lower hydration temperature compared to individually minced *cassia* and guar conventional Blends.

Accordingly, the more expensive galactomannans such as locust bean gum (LBG) and tara gum can be replaced by co-minced *cassia*/guar Systems. For instance, LBG is a galactomannan having a galactose to mannose ratio of 4:1. A co-minced system comprising 80% *cassia* gum (galactose to mannose ratio 5:1) and 20% guar gum (galactose to mannose ratio 2:1) gives on average the same carbohydrate composition as LBG having the above galactose to mannose ratio. The differences in performance are within the natural range of hydrocolloids: The results are summarized in the following Table.

| Performance | Cold Viscosity |
|---|---|
| Co-minced (80:20) *cassia*/guar system: | 293 mPas |
| LBG (food grade) (Industrias Agricolas Mallorca SA) | 72 mPas |

The co-minced System according to the invention is better in terms of cold water solubility, even without purification with iso-propyl alcohol, which is necessary to reach food grade purity. This treatment will increase the performance parameters of the system significantly. By the method of the invention it is not only possible to adjust any naturally occurring galactomannan performance parameter but it is possible to achieve a balance of properties exceeding the individual properties of naturally occurring galactomannans.

Example 6

A *cassia* hydrocolloid was prepared according to the general procedure according to the invention mentioned above. The product obtained was compared to a *cassia* hydrocolloid which was obtained according to the method of U.S. Pat. No. 2,891,050. The properties of the individual hydrocolloids measured under identical conditions are summarized in the Table which follows.

| Performance Parameter | Traditional Milling (USPN 2,891,050) | Wet Mincing | Improvement Achieved |
|---|---|---|---|
| Brookfield Viscosity (1%; 20 rpm) | 175 mPas | 924 mPas | +528% |
| Gel Strength [FIRA] | 148 g | 216 g | +46% |
| Retorting Stability Against Standard (130° C./1 hour) | 1.06 | 1.75 | +65% |

The results above show that the method of the invention for making the galactomannan hydrocolloid results in a significant increase in performance parameters, such as Brookfield viscosity, gel strength and retorting stability. Similar results are likewise obtained for the tara, locust bean and guar gums.

Example 7

*Cassia* Dispersions

Figure 2:
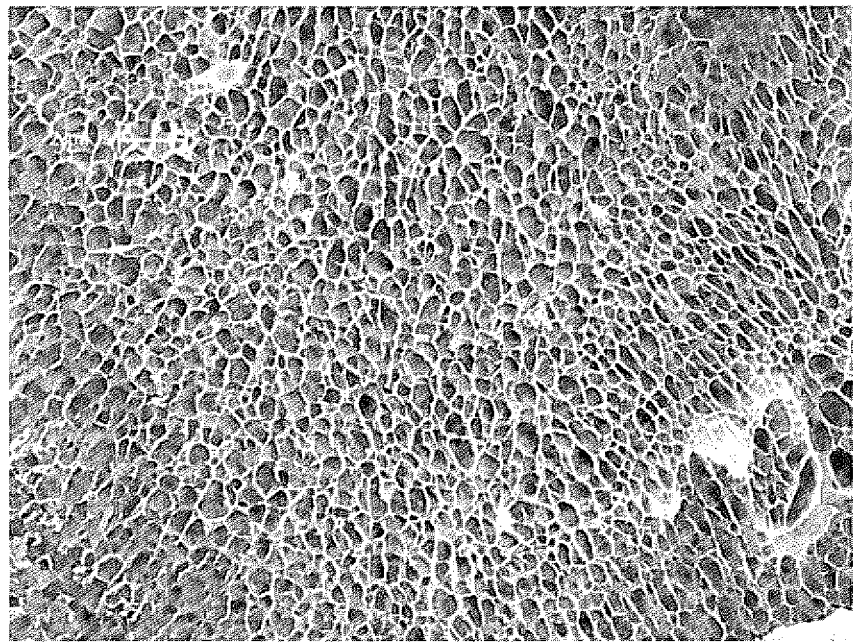
FIGS. 2, 4, and 6 are cryogenic scanning electron micrographs (cryoSEM) of a 2 percent (w/w) aqueous dispersions of *cassia* hydrocolloid prepared according to the process of the invention. The scale bar is depicted within each cryoSEM micrograph.
Figure 3:
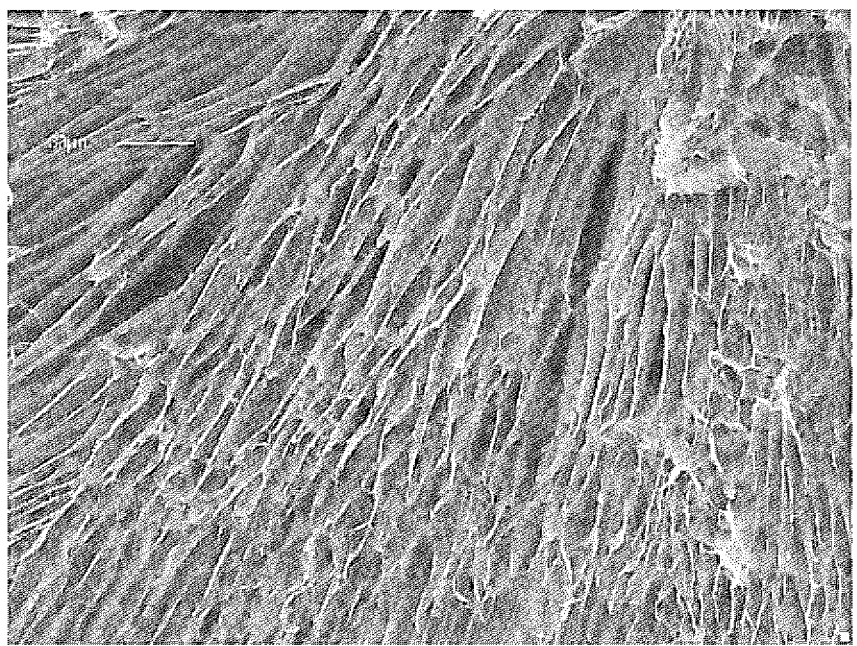
FIGS. 3, 5, and 7 are cryoSEM micrographs of 2 percent (w/w) aqueous dispersions of *cassia* hydrocolloid prepared according to the conventional prior art process. The scale bar is depicted within each micrograph.
Figure 4:
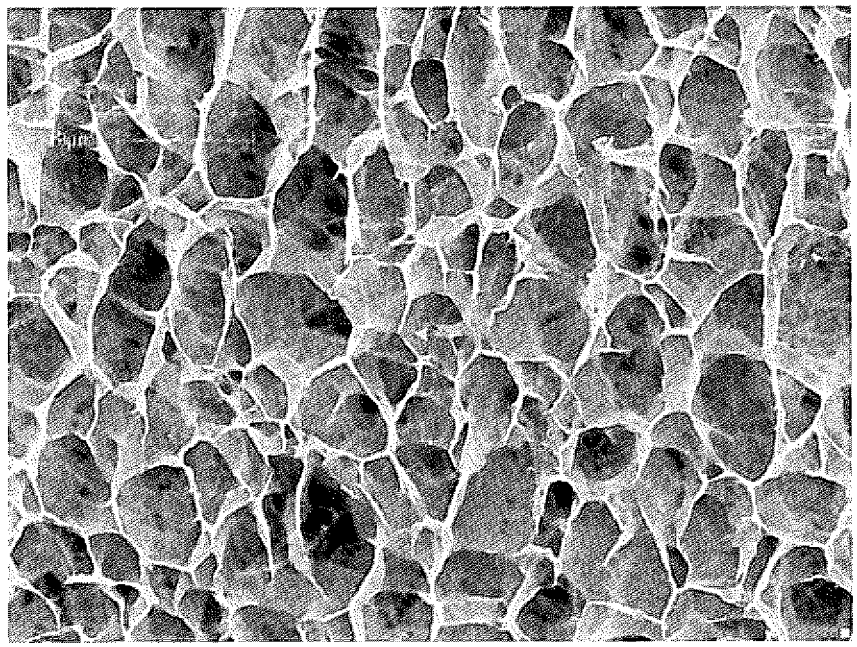
Figure 5:
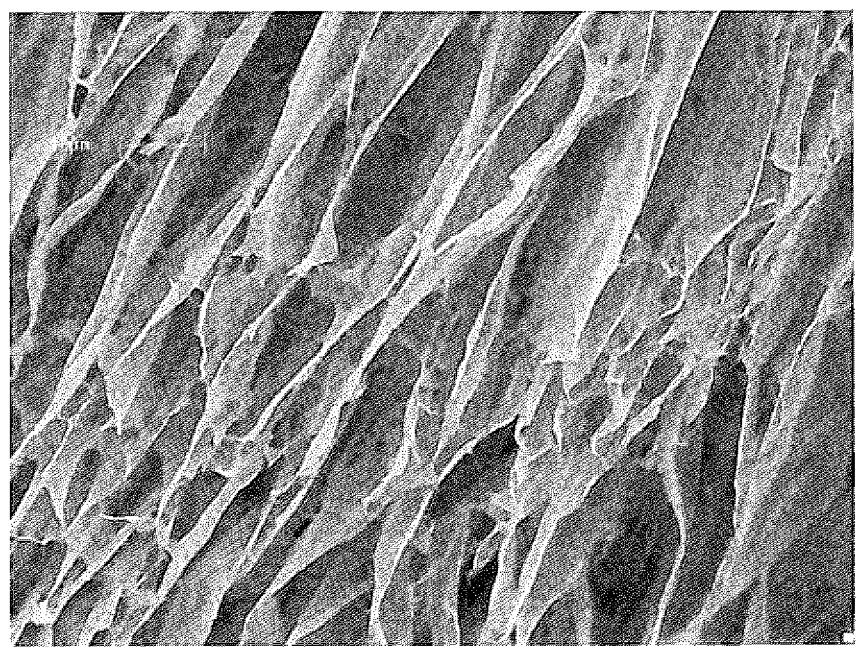
Figure 6:
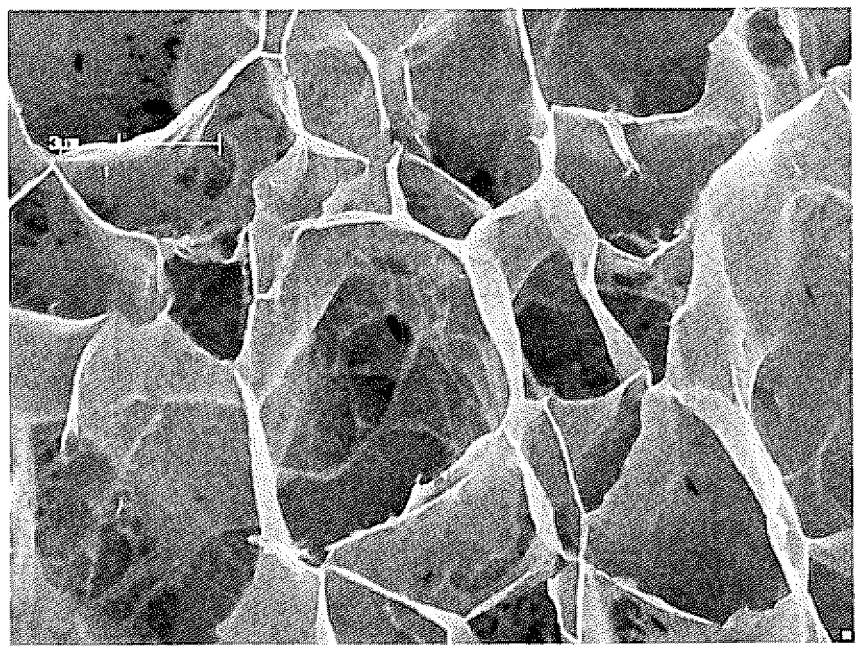
Figure 7:
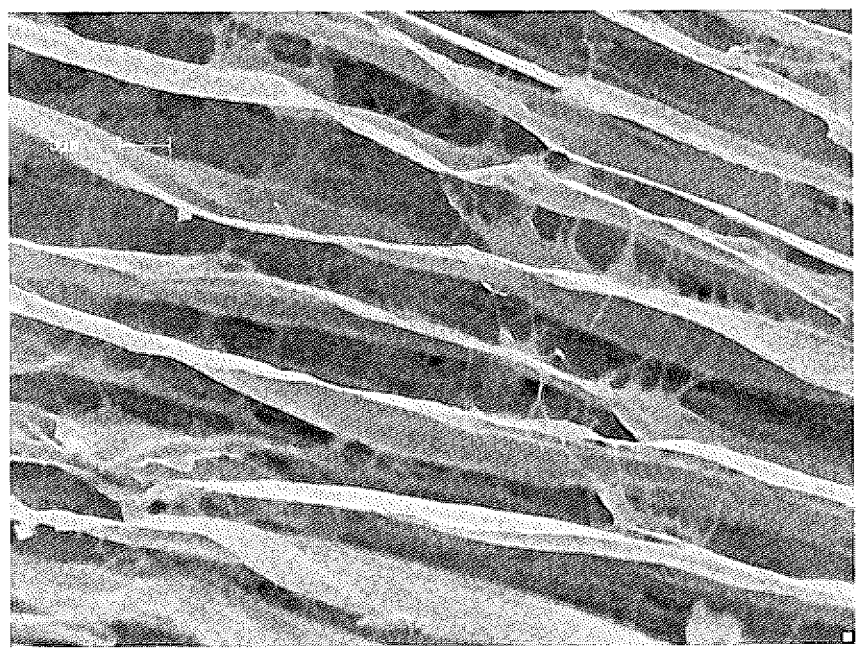
Figure 8:
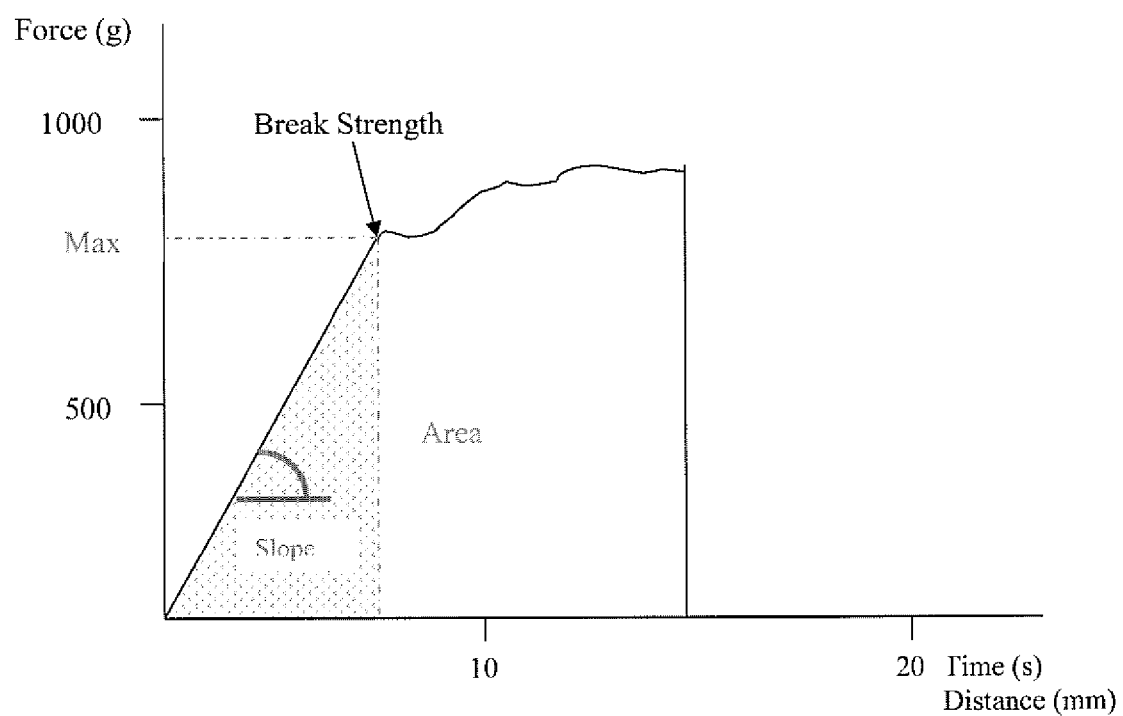
FIG. 8 represents a plot obtained when measuring the gel properties of a sample with a texture analyzer (Stable Micro Systems, type TA XT2i).

The morphologies and physical properties of *cassia* hydrocolloid samples prepared by the mincing process of the invention are compared to *cassia* hydrocolloid samples prepared by the flake/grinding process described in U.S. Pat. No. 2,891,050. *Cassia* hydrocolloid dispersions utilizing *cassia* hydrocolloid made by the method of the present invention and *cassia* hydrocolloid made by the method described in U.S. Pat. No. 2,891,050 are prepared micrographed according to the procedure set forth under the CryoSEM protocol described above (Procedure 2.6), except that 2 wt. % dispersions in deionized water were prepared. As shown in FIGS. 2, 4, and 6, the morphology of the *cassia* hydrocolloid prepared by the mincing process of the invention is relatively spherical in shape with well defined walls between contiguous cells. In sharp contrast, as shown in FIGS. 3, 5, and 7 the cellular structure of *cassia* hydrocolloid prepared by the prior art process is elongated with most of the cell walls between contiguous cells being damaged.

The Brookfield viscosity at 20 rpm and yield values are recorded. Yield values are estimated by subtracting the Brookfield viscosity measured at 0.5 rpm from the Brookfield viscosity at 1 rpm, and dividing the results by 100. The following results were obtained:

|  | Brookfield Viscosity at 20 rpm (mPas) | Yield value (dynes/cm2) |
|---|---|---|
| Standard *cassia* | 1245 (spindle 3) | 30 (spindle 3) |
| Wet-minced *Cassia* | 19400 (spindle 5) | 467 (spindle 5) |

It is believed that the mechanical compression and tearing forces excreted by flaking and grinding steps utilized by prior art processes damage the cellular structure of the hydrocolloid structure, leading to diminished physical properties.

Example 8

Air Freshener Formulations

Air freshener gels were made with a hydrocolloid blend consisting of wet minced *cassia* or standard *cassia*, standard guar and K-carrageenan (Aquagel MM60 from Marcell). The air freshener gels were made with two different surfactants Tween 80 or Cromophor CO40, with all formulations containing 2.5 wt. % Springtime Fresh Fragrance (available American Fragrance Supply). The formulations contained an overall gelling package of 2.6 wt. % of hydrocolloids blend as shown below.

|  |  | Example | | | |
|---|---|---|---|---|---|
|  |  | 8A (wt. %) | Comparative 8A (wt. %) | 8B (wt. %) | Comparative 8B (wt. %) |
| Wet Minced *Cassia* |  | 0.65 |  | 0.65 |  |
| Standard *Cassia* | Novegum C865 (Noveon) |  | 0.65 |  | 0.65 |
| K-Carrageenan | Aquagel MM60 (Marcel)) | 0.98 | 0.98 | 0.98 | 0.98 |
| Guar | EX-888 (Noveon) | 0.38 | 0.38 | 0.38 | 0.38 |
| Calcium Acetate Monohydrate |  | 0.31 | 0.31 | 0.31 | 0.31 |
| KCl |  | 0.24 | 0.24 | 0.24 | 0.24 |
| Sodium Hydrogen Sulfite |  | 0.05 | 0.05 | 0.05 | 0.05 |
| POE(20)-Sorbitan Monooleate | Tween 80 (Uniqema) | 2.5 | 2.5 |  |  |
| Ethoxylated Castor Oil | Cromophor CO40 (BASF) |  |  | 2.5 | 2.5 |
| Perfume Oil | Springtime Fresh | 2.5 | 2.5 | 2.5 | 2.5 |
| Formaldehyde 37% |  | 0.3 | 0.3 | 0.3 | 0.3 |
| Deionized Water |  | 93.6 | 93.6 | 93.6 | 93.6 |
| Total (g) |  | 100 | 100 | 100 | 100 |

The hydrocolloids gelling package is dispersed in water at 75° C. for about 30 minutes until all hydrocolloids and salts are fully hydrated. The mixture is cooled to 55° C. then the fragrance, surfactant and preservative is added under mixing. The hot air freshener solution is placed into small containers and allowed to cool and stand undisturbed at room temperature overnight. The gel properties were measured by a texture analyzer from Stable Micro Systems, type TA XT2i. A cylindrical stamp with 258 mm$^2$ (0.4 in$^2$) bottom surface penetrated the gel samples at a speed of 1 mm/s for a set depth distance of 15 mm.

The break strength is obtained in gram and represents the maximum force for the tip of the cylindrical stamp to penetrate the gel initially before it breaks, the gel rigidity (in g/s or g/mm) is measured by the slope of the curve before the gel breaks, and the indirect measure of the inner gel strength (in g·s or g·mm) and is measured by the area under the curve at the maximum force. The results are summarized in the following Table.

|  | Break Strength Force (g) | Rigidity Slope (g/s) | Work to Penetrate Gel* Area (g · s) |
|---|---|---|---|
| Example 8A | 2567 | 714 | 4433 |
| Comparative 8A | 1619 | 623 | 2083 |
| % Improvement | 58% | 14% | 113% |
| Example 8B | 2576 | 673 | 4830 |
| Comparative to 8B | 2140 | 688 | 3445 |
| % Improvement | 20% | -2% | 40% |

*Indicative of inner gel strength

The texture analyzer results indicate that the gels prepared from wet minced *cassia* show higher break strength, higher inner gel strength and relatively equivalent rigidity than gel made from standard *cassia*. Furthermore, the gels made from wet minced *cassia* display better color: a white semitransparent gel is obtained with wet minced *cassia* compared to an opaque brown color gel from standard *cassia*.

Example 9

Xanthan-Based Co-Minced Dispersions

Aqueous gels containing co-minced *cassia* splits (cassia tora) and xanthan gum (Ceroga from C. E. Roeper) by wet mincing were compared to gels prepared from the physical blend of conventionally processed *cassia* and xanthan gums. The gels were prepared by dispersing and hydrating the *cassia*/xanthan gum compositions in water at 50° C. Each gel sample contains 2 wt. % hydrocolloids, with respective composition of 50 wt. % *cassia* and 50 wt. % xanthan gum. The gel properties were measured by texture analyzer, under the same conditions as previously described. The results are summarized in the following Table.

|  | Break Strength Force (g) | Rigidity Slope (g/s) | Work to Penetrate Gel* Area (g · s) |
| --- | --- | --- | --- |
| Example 9A *Cassia*/Xanthan 50/50 Co-Minced |  |  |  |
| Average | 1469 | 22.2 | 6526 |
| sdt dev | 52 | 0.5 | 700 |
| Comparative to 9B *Cassia*/Xanthan 50/50 Blended |  |  |  |
| Average | 1372 | 22.6 | 5513 |
| sdt dev | 160 | 0.5 | 481 |
| % Improvement | 7 | −2 | 18 |

*indicative of gel strength

The texture analyzer results indicate that the gels prepared from co-minced *cassia*-xanthan gums show higher break strength, higher inner gel strength and relatively equivalent elasticity than gel made from the equivalent physical blend.

Example 10

Silicone Shampoos

Various 2 in 1 conditioning shampoos containing silicone emulsion and cationic polysaccharides are prepared according to the formulations set forth below. The shampoos are prepared as previously set forth by adding the ingredients in the order described in the following table under mixing. The results for the Brookfield viscosity measured at 20 rpm and the foam height are summarized below.

| Formulation |  | Comparative 10A (wt %) | Comparative 10B (wt %) | 10 (wt %) |
| --- | --- | --- | --- | --- |
| Deionized Water |  | q.s to 100 | q.s to 100 | q.s to 100 |
| Cationic Guar | Jaguar ™ Excel (Rhodia) N = 1.37% | 0.3 |  |  |
| Cationic Guar | Jaguar ™ C13S (Rhodia) N = 1.37% |  | 0.3 |  |
| Cationic *Cassia* | Sample A N = 4.25% |  |  | 0.3 |
| Cocoamidopropyl Betaine (50%) | Tego Betaine F 50 (Degussa) | 16.2 | 16.2 | 16.2 |
| Sodium Laureth-2 Sulfate (2 mole, 26%) | Standapol ES2 (Cognis) | 18.5 | 18.5 | 18.5 |
| Propylene Glycol |  | 2 | 2 | 2 |
| PG(and)Diazolidinyl Urea MeParaben Propylparaben | Germaben II (Sutton) | 0.5 | 0.5 | 0.5 |
| Silicone Emulsion | Dow Fluid HMW 2220 (Dow Corning) | 3 | 3 | 3 |
| Citric Acid (50%) |  | pH adjust to 5.5 | | |
| Brookfield Viscosity (Cps) at 20 rpm, Spindle 4 |  | 2240 | 2940 | 2090 |
| Foam Height (ml) |  | 240 | 190 | 225 |

The results show that all shampoos displays similar viscosities and foam heights.

Bleached hair tresses were washed one time with 1 gram of shampoo for 30 seconds. The shampoo was left on the hair for about 3 minutes then the shampoo was rinsed off the tress under warm water for about one minute. Wet combing was evaluated through a panel test according to the standard test for directional difference (ASTM E2164-01). The results indicate that the panelists could not detect any significant difference in the wet combing performance of the wet minced cationic *cassia* containing shampoo to the commercial cationic guar containing shampoos indicative of similar conditioning properties after one washing. Dry combing was evaluated through a panel test according to the standard paired test for directional difference (ASTM E2164-01). The results indicate that the 64% of the panelists found that force necessary to comb the dry hair (dry combing) was lower for the shampoo containing cationic *cassia* compared to the shampoo containing the commercial cationic guar (Jaguar excel).

Silicone Deposition

Bleached hair tresses were washed 5 times with those shampoos (Example 10 series), according to the method previously described. Silicone and chlorine content on the hair were measured by ICP-AA (Ionized Coupled plasma atomic absorption). The results are tabulated below.

|  | Silicone Content (µg/g hair) | Chlorine Content (µg/g hair) |
| --- | --- | --- |
| Unwashed Hair | <22 | 28 |
| Hair Washed with Shampoo Comparative 10A | <20 | 76 |
| Hair Washed with Shampoo Comparative 10B | <24 | 52 |
| Hair Washed with Shampoo 10 | 150 | 58 |

The results show that the wet minced cationic *cassia* containing shampoo of this invention is more efficient at depositing silicone onto the hair (superior silicone deposition aid) than the commercially available cationic guar, as seen by the amount of silicone measured on the hair. No significant differences were detected in the amount of chlorine measured on the hair, indicative of similar deposition of the cationic polymers.

Example 11

Bathroom and Tile Cleaner Gel

An oxalic acid-based gel designed to clean basins, bathtubs or tiles is formulated according to the following recipe:

|  |  | Formulation (wt. %) |
|---|---|---|
| Deionized Water |  | 53.7 |
| Xanthan Gum | Ceroga (C. E. Roeper) | 0.8 |
| Magnesium Aluminum Silicate | Van Gel B (Vanderbilt) | 3 |
| Oxalic Acid Dehydrate (12.5% aqueous solution) |  | 40 |
| Polysorbate 40 | Tween 40 (Uniqema) | 3 |
| NaOH (50%) |  | Adjust pH to 4.5 |

The gum is dispersed in water (with slight heating if necessary to allow for full hydration) for 30 minutes. The other ingredients are added in the order tabulated above under mixing. The xanthan gum is then co-minced with various gums according to the wet mincing process of the invention and introduced in the formulation at the same concentration (0.8 wt. %). The results for the Brookfield viscosity at 20 rpm and yield value are summarized below:

| Example |  | Brookfield Viscosity at 20 rpm (mPas) | Yield Value (Dynes/cm$^2$) |
|---|---|---|---|
| Comparative 11 | Xanthan | 3820 (spindle 5) | 356 (spindle 5) |
| 11A | Co-Minced Xanthan/Guar 50/50 | 5790 (spindle 5) | 368 (spindle 5) |
| 11B | Co-Minced Xanthan/*Cassia* 75/25 | 4840 (spindle 5) | 460 (spindle 5) |

The results indicated that depending on the co-minced gums composition, some are more efficient in thickening the oxalic acid-based formulation than the pure xanthan.

Example 12

Bathroom and Tile Cleaner Gel

A calcium carbonate-based gel designed to clean basins, bathtubs or tiles is formulated according to the following recipe:

|  |  | Formulation (wt. %) |
|---|---|---|
| Deionized Water |  | 43.4 |
| Xanthan Gum | Ceroga (C.E. Roeper) | 0.4 |
| Magnesium Aluminum Silicate | Veegum T (Vanderbilt) | 1.2 |
| Benzyl Alkyl Sulfonic Acid | Bio-Soft S-100 | 15 |
| Calcium Carbonate |  | 50 |
| NaOH (50%) |  | Adjust pH to 8-9 |

The gum is dispersed in water (with slight heating if necessary to allow for full hydration) for 30 minutes. The other ingredients are added in the order tabulated above with mixing. The xanthan gum is then co-minced with various gums according to the invention mincing process and introduced in the formulation at the same concentration (0.4 wt. %). The results for the Brookfield viscosity at 20 rpm and yield value are summarized below:

| Example |  | Brookfield Viscosity at 20 rpm (mPas) | Yield Value (Dynes/cm$^2$) |
|---|---|---|---|
| Comparative 12 | Xanthan | 15050 (spindle 6) | 300 (spindle 6) |
| 12A | Co-Minced Xanthan/*Cassia* 50/50 | 44200 (spindle 7) | 1480 (spindle 7) |
| 12B | Co-Minced Xanthan/Guar 50/50 | 10600 (spindle 6) | 210 (spindle 6) |
| 12C | Co-Minced Xanthan/*Cassia* 75/25 | 18350 (spindle 6) | 260 (spindle 6) |
| 12D | Co-Minced Xanthan/*Cassia* 25/75 | 19350 (spindle 6) | 1740 (spindle 6) |

The results indicated that the co-minced gums are more efficient in thickening the calcium carbonate-based formulation than the pure xanthan.

Example 13

Conditioning Treatment

Leave in conditioning treatments were formulated with cationic gums according to the following formulation. All ingredients were added under mixing in the order listed.

| Formulation |  | Comparative 13 (wt. %) | 13 (wt. %) |
|---|---|---|---|
| Deionized Water |  | q.s to 100 | q.s to 100 |
| Cationic Guar | Jaguar Excel (Rhodia) N = 1.37% | 0.5 |  |
| Cationic *Cassia* | Sample A N = 4.25% |  | 0.5 |
| Acetamide MEA | Schercomid AME (Scher Chemical) | 5 | 5 |
| Lauryldimonium Hydroxypropyl Hydrolized Collagen | Croquat L (Croda Inc.) | 1.5 | 1.5 |
| Distearyldimonium Chloride | Arosurf TA-100 (Witco) | 1.5 | 1.5 |
| DMDM Hydantoin | Glydant (Lonza) | 0.3 | 0.3 |
| Citric Acid (50%) |  | pH adjust | pH adjust |
| Total (g) |  | 100 | 100 |

Bleached hair tresses were treated with 1 g of the leave in conditioning treatment. An attribute that is closely associated with conditioning is ease of combing. Wet combing was evaluated through a panel test according to the standard test for directional difference (ASTM E2164-01). The results indicate that the 75% of the panelists found that the force necessary to comb the wet hair (wet combing) was lower in the case of cationic *cassia*-containing formulation compared to the formulation containing the commercial cationic guar.

Example 14

Clear Shampoos

Clear shampoos were formulated with various cationic polymers (prepared by the process of the present invention) and the anionic and amphoteric surfactants, sodium laureth sulfate and disodium cocoamphodiacetate. Commercially available cationic guar Jaguamm Excel from Rhodia was used as a comparison. The cationic gums are dispersed in deionized water until fully hydrated. Disodium cocoamphodiacetate is first slowly added under mixing, followed by the addition of sodium laureth-2 sulfate. The remaining ingredients are then added under mixing in the order described in the formulation table below. The Brookfield viscosity at 20 rpm, turbidity and foam heights were recorded.

| Formulation | Source | Comparative 14 (wt. %) | 14A (wt. %) | 14B (wt. %) |
|---|---|---|---|---|
| Deionized Water | | 57.8 | 57.8 | 57.8 |
| Cationic Guar | Jaguar ™ Excel (Rhodia) N = 1.37% | 0.25 | | |
| Cationic *Cassia* | Sample A N = 4.25% | | 0.25 | |
| Cationic *Cassia* | Sample C N = 3.78% | | | 0.25 |
| Disodium Cocoamphodiacetate | Monateric CLV (50%) (Uniqema) | 16.2 | 16.2 | 16.2 |
| Sodium Laureth-2 Sulfate (2 mole, 26%) | Standapol ES2 (Cognis) | 18.5 | 18.5 | 18.5 |
| PPG2hydroxyethylcoCo/ Isostereamide | Propidium 2 (Uniqema) | 4 | 4 | 4 |
| Propylene Glycol | | 2 | 2 | 2 |
| PG(and)Diazolidinyl Urea Methylparaben Propylparaben | Germaben II (Sutton) | 0.25 | 0.25 | 0.25 |
| Citric Acid | | As needed to bring pH to 6.1 | | |
| Total (g) | | 100 | 100 | 100 |
| Formulation | | Comparative 14 | 14A | 14B |
| Brookfield Viscosity at 20 rpm Spindle 3 (mPas) | | Phase Separation | 405 | 270 |
| Turbidity (NTU) | | — | 11.7 | 16.1 |
| Foam Height (ml) | | — | 190 | 205 |

The results show that the cationic *cassia* containing shampoos of this invention form a stable formulation compared to a shampoo formulated with commercial cationic guar (precipitation due to the incompatibility with the various surfactants). The resulting formulated shampoos had good clarity and good foaming.

Example 15

Clear Shampoo Formulations

Clear shampoos were formulated with various cationic polymers of the present invention and the anionic and amphoteric surfactants, sodium laureth-2-sulfate and cocamidopropylbetaine, according to the following recipe. Commercially available cationic guar (Jaguar™ C13S from Rhodia) was used as a comparison. The shampoos are prepared in a manner similar to that previously described. Brookfield viscosity at 20 rpm, turbidity and foam heights were recorded.

| | | Comp. 15 (wt. %) | 15A (wt. %) | 15B (wt. %) | 15C (wt. %) | 15D (wt. %) | 15E (wt. %) |
|---|---|---|---|---|---|---|---|
| DI Water | | 59.05 | 57.05 | 57.05 | 57.05 | 57.05 | 57.05 |
| Cationic Guar | Jaguar ™ C13S (Rhodia) N = 1.37% | 0.25 | | | | | |
| Cationic *Cassia* | Sample B N = 4.14% | | 0.25 | | | | |
| Cationic *Cassia* | Sample E N = 2.43% | | | 0.25 | | | |
| Cationic *Cassia* | Sample D N = 3.45% | | | | 0.25 | | |
| Cationic Guar | Sample F N = 4.05% | | | | | 0.25 | |
| Co-Minced Cationic *Cassia* Guar 50/50 | Sample G N = 1.85% | | | | | | 0.25 |
| Cocamido-Propyl Betaine (50%) | Tego Betaine F 50 (Degussa) | 16.2 | 16.2 | 16.2 | 16.2 | 16.2 | 16.2 |
| Sodium Laureth-2 Sulfate (2 mole, 26%) | Standapol ES2 (Cognis) | 18.5 | 18.5 | 18.5 | 18.5 | 18.5 | 18.5 |
| PPG2 Hydroxyethyl-Coco/Isoste Re-Amide | Promidium 2 (Uniqema) | 4 | 4 | 4 | 4 | 4 | 4 |

-continued

| | | Comp. 15 (wt. %) | 15A (wt. %) | 15B (wt. %) | 15C (wt. %) | 15D (wt. %) | 15E (wt. %) |
|---|---|---|---|---|---|---|---|
| Propylene Glycol | | 2 | 2 | 2 | 2 | 2 | 2 |
| PG(and)-Diazolidinyl Urea MeParaben Propylparaben | Germaben II (Sutton) | 0.25 | 0.25 | 0.25 | 0.25 | 0.25 | 0.25 |
| Citric Acid | | As needed to bring pH to 6.1 | | | | | |
| Total (g) | | 100 | 100 | 100 | 100 | 100 | 100 |

The results for the Brookfield viscosity at 20 rpm, turbidity, clarity at 420 nm and foam heights are tabulated below:

| | Comparative 15 | 15A | 15B | 15C | 15D | 15E |
|---|---|---|---|---|---|---|
| Clarity (% Transmittance at 420 nm) | 28.1 | 77.7 | 64.4 | 77.2 | 81 | 74.3 |
| Turbidity (NTU) | 34 | 14.8 | 13.3 | 11.4 | 10.5 | 14.5 |

The results show that all shampoos displays similar viscosities and foam heights. The shampoos formulated with the cationic polymers obtained by the process of the invention display much higher clarity and lower turbidity than the shampoos formulated with the commercially available cationic guar Jaguar™ C13S.

Example 16

Shampoos

Clear shampoos were formulated with various cationic polymers of the invention as set forth above. Clarity and turbidity values are measured and recorded.

| | | Comparative 16 (wt. %) | 16A (wt. %) | 16B (wt. %) |
|---|---|---|---|---|
| Deionized Water | | 57.05 | 57.05 | |
| Cationic Guar | Jaguar™ C13S (Rhodia) N = 1.37% | 0.25 | | |
| Cationic Cassia | Sample A N = 4.25% | | 0.25 | |
| Cationic Cassia | Sample C N = 3.78% | | | 0.25 |
| Cocamidopropyl-Betaine (50%) | Tego betaine F 50 (Degussa) | 16.2 | 16.2 | 16.2 |
| Sodium Laureth-2 Sulfate (2 mole, 26%) | Standapol ES2 (Cognis) | 18.5 | 18.5 | 18.5 |
| PPG2 Hydroxy-EthylCoco/Isostere-Amide | Promidium 2 (Uniqema) | 4 | 4 | 4 |
| Propylene glycol | | 2 | 2 | 2 |
| PG(and) Diazolidinyl Urea Methylparaben Propylparaben | Germaben II (Sutton) | 0.25 | 0.25 | 0.25 |
| Citric Acid | | As needed to bring pH to 6.1 | | |
| Total (g) | | 100 | 100 | 100 |

-continued

| | Comparative 16 (wt. %) | 16A (wt. %) | 16B (wt. %) |
|---|---|---|---|
| Clarity (% Transmittance at 420 nm) | 28.1 | 76.8 | 76.6 |
| Turbidity (NTU) | 34 | 8.2 | 6.8 |

The results show that shampoos formulated with the cationic polymers obtained by the process of the invention display much higher clarity and lower turbidity values than the shampoos formulated with the commercially available cationic guar (Jaguar™ C13S).

Example 17

Film Forming Properties

Films are prepared by evaporation in a controlled environment room of 1 wt. % wet minced cationic gums dispersions in deionized water. Film specimens were prepared according to ASTM D 1708. Tensile properties were measured at 0.8 mm/s, according to ASTM D882, on a TA XT PLUS instrument from Stable Micro Systems. The Tensile properties are summarized below:

| Polymer | % Nitrogen | Elongation (%) | Tensile Strength (MPa) |
|---|---|---|---|
| Cationic Guar | Sample A N = 4.05% | 66.1 | 3.6 |
| | Std dev | 9.8 | 0.9 |
| Cationic Cassia | Sample B N = 3.45% | 23.5 | 20.5 |
| | Std dev | 6.8 | 3.4 |
| Cationic Cassia | Sample C N = 4.1% | 59.0 | 6.8 |
| | Std dev | 4.8 | 0.7 |
| Jaguar™ Excel (Rhodia) | N = 1.37% | 7.5 | 45.1 |
| | Std dev | 1.2 | 7.0 |

As illustrated by the results, the cationic cassia and guar samples obtained with the process of the present invention are excellent film formers, with properties depending on the cationic charge content. The percent elongation increases and the tensile strength decreases with increasing cationic charge density (increasing nitrogen content) of the cationic product derived form the inventive process. Elastomer-type tensile curves are observed for the cationic polymers with 4% nitrogen (381 and 390), where as plastic type tensile curves are observed for polymers with lower than 4% nitrogen content.

Very brittle films are obtained in the case of the commercially available cationic guar Jaguar™ Excel.

Example 18

Hair Fixative

A hair fixative resin should also encompass a number of subjective and objective properties such as curl ease of formulation, feel on the hair, curl retention, fast drying and low tack, compatibility with ancillary formulation additives, etc. Cationic *cassia* samples of the invention (sample B and E) were evaluated for their potential hair fixative properties.

Hair Feel: The tactile feel that the hair acquires after been coated with a fixative resin is extremely important. Current polymers tend to leave the hair raspy, dry, gummy, grease, etc. The cationic *cassia* samples tested show good feel characteristics. They leave the hair soft and natural.

Tack: Most current fixative polymers tend to absorb moisture and therefore become tacky. The cationic *cassia* samples tested exhibit low tack.

Flake off: Fixative polymers, after drying on hair, exhibit high levels of flakes after combing, giving the hair a dandruff-like appearance. The cationic *cassia* samples tested exhibit the no flaking.

An important performance property that a hair fixative polymer must also have, is its ability to hold a hairstyle in place at relatively high humidity, i.e., curl retention. The curl retention ability of the cationic *cassia* samples of this invention was measured.

Curl Retention Protocol: several cationic *cassia* dispersions were prepared at 1 wt. % concentration in deionized water. 0.85 g of the dispersions was applied and smeared on clean, 2 grams, 15.24 cm (6 in) hair swatches. The swatches were rolled over salon rollers, dried and conditioned overnight. The swatches were mounted inside a humidity chamber at 27° C., and 90% of relative humidity. The curl retention was recorded as a function of time and calculated, as:

$$(L-L_{(t)}/L-L_{(o)}) \times 100 = \text{curl retention (\%)}$$

wherein: L=length of hair fully extended, $L_{(o)}$=length of hair before exposure to high humidity, $L_{(t)}$=length of hair after exposure at time (t).

The results for curl retention are tabulated below:

| | | Percent Curl Retention at 27° C. and 90% Relative Humidity | | | |
|---|---|---|---|---|---|
| | | After 8 Hours | | After 24 Hours | |
| | | Average | Std. Dev | Average | Std. Dev |
| Example 18A | Cationic Cassia Sample A N = 4.14% | 92.3 | 4.3 | 92.3 | 4.3 |
| Example 18B | Cationic Cassia Sample B N = 2.43% | 95.8 | 0.2 | 95.8 | 0.2 |

As shown by the results the wet minced cationic galactomannan hydrocolloids, in particular the wet minced cationic *cassia* polymers of this invention give raise to excellent curl retention ability under humid environment.

Example 19

Enzyme Containing Polygalactomannan Hydrocolloids 50 g of dry *cassia* hydrocolloid prepared according to the general procedure described above was added to a solution of 0.75 g of papain in 150 g of demineralized water. The gel strength of the gel obtained was determined to be 1557 g, the viscosity was 490 mPas.

A corresponding gel of 50 g of dry *cassia* hydrocolloid in 150 g of demineralized water resulted in a gel strength of the gel obtained of 1222 g and a viscosity of 252 mPas.

As is evident, the presence of an enzyme in the hydrocolloids of the invention does not adversely affect the end properties of the gel. To the contrary, the both gel strength and the viscosity are improved by the presence of the enzyme.

Example 20

Body Washes

Body washes containing cationic polysaccharides with various compositions and charge density were prepared according to the following formulation. All ingredients are mixed in a manner similar than previously described for the conditioning shampoos. The results are summarized in the following Table.

| | | Comparative 17 (wt %) | 17 (wt %) |
|---|---|---|---|
| Deionized Water | | q.s to 100 | q.s to 100 |
| EDTA | | 0.05 | 0.05 |
| Cationic Guar | Jaguar ™ C13S (Rhodia) N = 1.37% | 0.2 | |
| Cationic *Cassia* | Sample B N = 4.25% | | 0.2 |
| Cocamidopropyl Betaine (50%) | Tego betaine F50 (Degussa) | 15 | 15 |
| Sodium Laureth-2 Sulfate (2 mole, 26%) | Standapol ES2 (Cognis) | 10.6 | 10.6 |
| Cocamide MEA | Comperlan 100 (Cognis) | 0.9 | 0.9 |
| Cocamidopropyl Betaine (35%) | Velvatex BK-35 (Cognis) | 4.75 | 4.75 |
| Dimethiconol, TEA-Dodecylbenzene-Sulfonate | Dow Corning 1784 (Dow Corning) | 2 | 2 |
| Phenoxyethanol Ethylparaben Methylparaben Propylparaben Butylparaben Isobutylparaben | Phenonip (Clariant) | 0.5 | 0.5 |
| Total (g) | | 100 | 100 |
| Brookfield Viscosity (Cps) at 20 rpm, Spindle 5 | | 9400 | 10560 |
| Yield Value (dynes/cm$^2$) Spindle 5 | | 8 | 8 |
| Foam Height (ml) | | 185 | 135 |
| Stability at 45° C. | | phase separation after 3 weeks | stable |

The results show that all body washes display similar viscosities, yield value and foam heights. The body wash composition utilizing cationic derivatized *cassia* prepared in accordance with the present invention displays better stability at 45° C. than the commercially available cationic guar.

Example 21

Clear 2 in 1 Shampoos

Clear shampoos were formulated with various cationic polymers (prepared by the wet mincing process of the present invention) and the anionic and amphoteric surfactants, sodium laureth sulfate and disodium cocoamphodiacetate. Commercially available cationic guar Jaguar™ Excel from Rhodia was used as a comparison. The cationic gums are dispersed in deionized water until fully hydrated. Disodium cocoamphodiacetate is first slowly added under mixing, followed by the addition of sodium laureth-2 sulfate. The remaining ingredients are then added under mixing in the order described in the formulation table below. The Brookfield viscosity at 20 rpm, turbidity and foam heights were recorded.

|  |  | Example | | | | | |
|---|---|---|---|---|---|---|---|
|  |  | Comparative 1 (wt) | Comparative 2 (wt %) | 1A (wt %) | 1B (wt %) | 1C (wt %) | 1D (wt %) |
| DI water |  | 57.85 | 57.85 | 57.85 | 57.85 | 57.85 | 57.85 |
| EDTA |  | 0.05 | 0.05 | 0.05 | 0.05 | 0.05 | 0.05 |
| Cationic guar | Jaguar ™ Excel (Rhodia) N = 1.37% |  | 0.1 |  |  |  |  |
| Cationic cassia | Sample B N = 4.14% |  |  | 0.1 |  |  |  |
| Cationic cassia | Sample E N = 2.43% |  |  |  | 0.1 |  |  |
| Cationic cassia | Sample D N = 3.45% |  |  |  |  | 0.1 |  |
| Cationic guar | Sample F N = 4.05% |  |  |  |  |  | 0.1 |
| Cocamidopropyl betaine (50%) | Tego betaine F 50 (Degussa) | 15 | 15 | 15 | 15 | 15 | 15 |
| Sodium laureth-2 sulfate (2 mole, 26%) | Standapol ES2 (Cognis) | 20 | 20 | 20 | 20 | 20 | 20 |
| Lauramide DEA | Ninol 30LL | 2 | 2 | 2 | 2 | 2 | 2 |
| Quaternary Silicone | Ultrasil Qplus (Noveon Inc.) | 0.2 | 0.2 | 0.2 | 0.2 | 0.2 | 0.2 |
| Dimethicone PEG-7 phtalate | Ultrasil CA-1 (Noveon Inc.) | 1 | 1 | 1 | 1 | 1 | 1 |
| Amino-functional silicone | Ultrasil A-23 (Noveon Inc.) | 1 | 1 | 1 | 1 | 1 | 1 |
| PPG2hydroxyethylcoco/ isostereamide | Promidium CO (Uniqema) | 1 | 1 | 1 | 1 | 1 | 1 |
| PG(and)diazolidinyl urea MeParaben Propylparaben | (Kathon) | 0.05 | 0.05 | 0.05 | 0.05 | 0.05 | 0.05 |
| Fragrance |  | 0.25 | 0.25 | 0.25 | 0.25 | 0.25 | 0.25 |
| Total (g) |  |  |  | 100 |  |  |  |

The results for the Brookfield viscosity at 20 rpm, turbidity, clarity at 420 nm and foam heights are tabulated below:

|  | Comparative 1 | Comparative 2 | 1A | 1B | 1C | 1D |
|---|---|---|---|---|---|---|
| Brookfield viscosity (Cps) at 20 rpm, Spindle 3 | 1325 | 1790 | 2035 | 2040 | 2165 | 2305 |
| Clarity (% transmittance at 420 nm) | 93.8 | 91.8 | 88.8 | 78.5 | 83 | 80 |
| Turbidity (NTU) | 4.1 | 5.4 | 8.4 | 6.7 | 7.2 | 9.2 |
| Foam Height (ml) | 223 | 187 | 200 | 253 | 225 | 240 |

The results show that all shampoos display similar clarity, turbidity and foam heights. The shampoos formulated with the cationic polymers obtained by the process of the invention display-higher viscosity than the shampoos formulated with the commercially available cationic guar Jaguar™ Excel or a shampoo formulated without cationic polygalactomannans.

Wet and dry combing Analysis

Bleached hair tresses were, washed one time with 1 gram of shampoo for 30 seconds. The shampoo was left on the hair for about 3 minutes then the shampoo was rinsed off the tress under warm water for about one minute. The work to wet comb (in N·mm) after one wash is recorded with a texture analyzer from Stable Micro Systems, type TA XT2i, by running each hair tress through a comb at 20 mm/s ten times. The data presented is the average of 5 tresses with 10 pulls each. The experiment is repeated after 5 consecutive washes and 10 consecutive washes.

| Formulation | Work to wet comb (N · mm) | | |
|---|---|---|---|
| | 1 wash | 5 washes | 10 washes |
| Comparative 1 | 252.8 ± 127.5 | 301.1 ± 65.1 | 369.4 ± 112.4 |
| Comparative 2 | 227.0 ± 68.5 | 177.8 ± 63.1 | 243.9 ± 49.4 |
| Example 1A | 186.0 ± 51.6 | 186.6 ± 51.3 | 149.5 ± 30.9 |

The results show that a decrease in the work for wet combing is obtained when the formulation contains a cationic polygalactomanan, with cationic *cassia* performing better than commercial Jaguar™ Excel.

A percentage change in the wet combing can also be calculated from 1 to 5 washes and from 1 to 10 washes. The results are tabulated below:

| Formulation | % change from 1 wash to 5 washes | % changes from 1 wash to 10 washes |
|---|---|---|
| Comparative 1 | +27.4 ± 102.0% | +51.4 ± 60.9% |
| Comparative 2 | −20.8 ± 15.8% | +14.5 ± 38.5% |
| Example 1A | −0.4 ± 22.7% | −19.4 ± 15.7% |

The results seem to indicate that less build-up after 10 washes was observed in the cationic *cassia*-containing shampoo compared to the others, as observed by the reduction in the wet work force after 10 washes.

Work to dry comb was also measured on the tresses after the 10 washes. The results are summarized below:

| Formulation | Work to dry comb after 10 washes (N · mm) |
|---|---|
| Comparative 1 | 13.5 ± 0.5 |
| Comparative 2 | 12.1 ± 1.0 |
| Example 1A | 12.7 ± 1.1 |

The results show that both formulations containing the cationic polymers (guar or *cassia*) performs similarly in dry combing measurements after 10 washes.

What is claimed is:

1. A shampoo composition comprising:
   a) at least one minced cassia polygalactomannan derivatized with a cationic substituent;
   b) a cleansing surfactant selected from anionic, cationic, amphoteric, and zwitterionic detersive surfactants, and mixtures thereof;
   c) a water soluble silicone compound;
   d) water;

wherein said water soluble silicone is selected from one or more compounds represented by the formula:

$$\text{R'}-\underset{\underset{\text{Me}}{|}}{\overset{\overset{\text{Me}}{|}}{\text{Si}}}-\left[\text{O}-\underset{\underset{\text{R}}{|}}{\overset{\overset{\text{Me}}{|}}{\text{Si}}}\right]_o-\left[\text{O}-\underset{\underset{|}{|}}{\overset{\overset{\text{Me}}{|}}{\text{Si}}}\right]_p-\left[\text{O}-\underset{\underset{\text{R1}}{|}}{\overset{\overset{\text{Me}}{|}}{\text{Si}}}\right]_q-\text{O}-\underset{\underset{\text{Me}}{|}}{\overset{\overset{\text{Me}}{|}}{\text{Si}}}-\text{R'} \quad (I)$$

$$(CH_2)_3O(EO)_a(PO)_b(EO)_c\text{—}R8$$

wherein:
Me is methyl;
R and $R^1$ are independently selected from methyl, —OH, $-R^7$, and $-R^9$-A' or —$(CH_2)_3$—O-$(EO)_a$-$(PO)_b$-$(EO)_c$-G with the proviso that both R and R' are not methyl, —H or $R^7$;
$R^1$ is selected from lower alkyl $CH_3(CH_2)_n$— or phenyl where n is an integer from 0 to 22;
a, b, and c are integers independently ranging from 0 to 100;
EO is —$(CH_2CH_2O)$—;
PO is —$(CH_2CH(CH_3)O)$—;
o is an integer ranging from 1 to 200;
q is an integer ranging from 0 to 1000;
p is an integer ranging from 0 to 200;
$R^7$ is aryl, alkyl, aralkyl, alkaryl, or alkenyl group of 1-40 carbons;
$R^8$ is hydrogen or $R^7$ or C(O)—X wherein X is aryl, alkyl, aralkyl, alkaryl, alkenyl group of 1-40 carbons, or a mixture thereof;
$R^9$ is divalent group selected from alkylene of 1-40 carbons which may be interrupted with an arylene group of 6 to 18 carbons or an alkylene group containing unsaturation of 2 to 8 carbons; A' and G are independently are selected from:

$$-\overset{\overset{O}{\|}}{C}-OH, \quad -\overset{\overset{O}{\|}}{C}-O^-M^+, \quad -\overset{\overset{O}{\|}}{\underset{\underset{O}{\|}}{S}}-OH,$$

$$-\overset{\overset{O}{\|}}{\underset{\underset{O}{\|}}{S}}-O^-M^+, \quad -\overset{\overset{O}{\|}}{\underset{\underset{O}{}}{P}}-(OH)_2, \quad -\overset{\overset{O}{\|}}{\underset{\underset{O}{}}{P}}-(O^-M^+)_2,$$

$$-\overset{\overset{O}{\|}}{C}-R''-\overset{\overset{O}{\|}}{C}-OH, \text{ and } -\overset{\overset{O}{\|}}{C}-R''-\overset{\overset{O}{\|}}{C}-O^-M^+$$

wherein R" is a divalent group selected from alkylene of 1-40 carbons which may be interrupted with an arylene group of 6 to 18 carbons or an alkylene group of 2 to 8 carbons; and M is Na, K, Li, $NH_4$; or an amine containing alkyl, aryl, akenyl, hydroxyalkyl, arylalkyl or alkaryl groups;

$$R14-\underset{\underset{\text{Me}}{|}}{\overset{\overset{\text{Me}}{|}}{\text{Si}}}-\left[O-\underset{\underset{R11}{|}}{\overset{\overset{\text{Me}}{|}}{\text{Si}}}\right]_{a^1}-\left[O-\underset{\underset{R12}{|}}{\overset{\overset{\text{Me}}{|}}{\text{Si}}}\right]_{b^1}-\left[O-\underset{\underset{R13}{|}}{\overset{\overset{\text{Me}}{|}}{\text{Si}}}\right]_{c^1}-O-\underset{\underset{\text{Me}}{|}}{\overset{\overset{\text{Me}}{|}}{\text{Si}}}-R14 \quad (II)$$

wherein $R^{11}$ is selected from lower alkyl having one to eight carbon atoms or phenyl,
$R^{12}$ is —$(CH_2)_3$—O-$(EO)_x$-$(PO)_y$-$(EO)_z$-$SO_3^-M^+$
M is a cation and is selected from Na, K, Li, or $NH_4$;
x, y and z are integers independently ranging from 0 to 100;
$R^{13}$ is —$(CH_2)_3$—O-$(EO)_x$-$(PO)_y$-$(EO)_z$-H
$R^{14}$ is methyl or hydroxyl;
$a^1$ and $c^1$ are independently integers ranging from 0 to 50;
$b^1$ is an integer ranging from 1 to 50;

$$(R^{21}-O)_{e^1}-\overset{\overset{O}{\|}}{P}-(O^-M^+)_{f^1} \quad (III)$$

wherein $R^{21}$ is

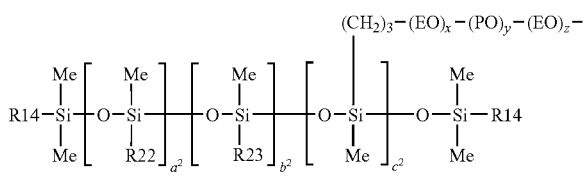

$a^2$ is an integer from 0 to 200;
$b^2$ is an integer from 0 to 200;
$c^2$ is an integer from 1 to 200;
$R^{14}$ is as defined above;
$R^{22}$ is selected from $-(CH_2)_nCH_3$ and phenyl;
n is an integer from 0 to 10;
$R^{23}$ is $-(CH_2)_3-O-(EO)_{x^1}-(PO)_{y^1}-(EO)_{z^1}-H$;
$x^1$, $y^1$ and $z^1$ are integers and are independently selected from 0 to 20;
$e^1$ and $f^1$ are 1 or 2 with the proviso that e+f=3;
M is selected from H, Na, K, Li, or $NH_4$; and (IV)

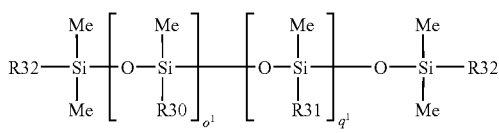

wherein Me is methyl;
$R^{30}$ and $R^{32}$ independently are $-CH_3$ or $-(CH_2)_3-O-(EO)_{a^3}-(PO)_{b^3}-(EO)_{c^3}-C(O)-R^{33}-C(O)-OH$;
with the proviso that both $R^{30}$ and $R^{32}$ are not $-CH_3$;
$R^{33}$ is selected from $-CH_2-CH_2-$; $-CH=CH-$; $-CH_2-CH(R^{37})$;

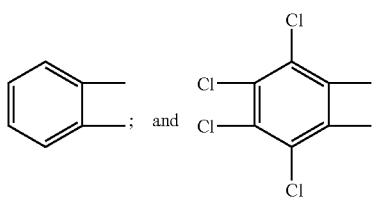

$R^{37}$ is alkyl having from 1 to 22 carbon atoms;
$R^{31}$ is selected from lower alkyl (having 14 carbons), $CH_3(CH)$, 1- and phenyl;
$n^1$ is an integer from 0 to 8;
$a^3$, $b^3$ and $c^3$ are integers independently ranging from 0 to 20;
EO is an ethylene oxide residue $-(CH_2CH_2-O)-$;
PO is a propylene oxide residue $-(CH_2CH(CH_3)-O)-$;
$o^1$ is an integer ranging from 1 to 200;
$q^1$ is an integer ranging from 0 to 500;

$R'CH_2C(O)OR$ (V)

wherein R is

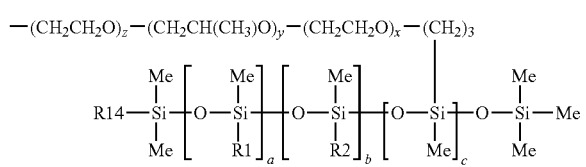

wherein Me is methyl, a is an integer from 0 to 200; b is an integer from 0 to 200; c is an integer from 1 to 200; $R^1$ is selected from $-(CH_2)_nCH_3$ and phenyl; n is an integer from 0 to 10; $R^2$ is $-(CH_2)_3-(OCH_2CH_2)_x-(OCH_2CH(CH_3))_y(OCH_2CH_2)_z-OH$; x, y and z are integers and are independently selected from 0 to 20; R' is represented by the formulae:

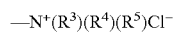

wherein $R^3$, $R^4$, and $R^5$ independently represent alkyl having from 1 to 20 carbon atoms;

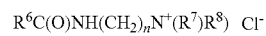

wherein $R^6$ is alkyl having from 6 to 20 carbon atoms, $R^7$ and $R^8$ are independently methyl or ethyl; n is an integer from 1 to 5;

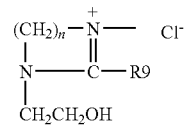

wherein $R^9$ is alkyl having from 6 to 20 carbon atoms, and v is an integer from 1 to 5; and (VI)

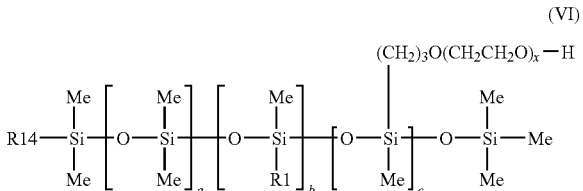

wherein Me is methyl, a is an integer from 0 to 200; b is an integer from 0 to 200; c is an integer from 1 to 200; $R^1$ is selected from $-NH-(CH_2)_2-NH_2$ or $-CH_2)_n-NH_2$; n is an integer from 2 to 6; and x is an integer from 0 to 20.

2. The shampoo composition of claim 1 wherein at least one C-6 hydroxyl group on the polygalactomannan backbone is derivatized with a cationic substituent.

3. The shampoo composition of claim 2 wherein said cationic substituent is represented by the formula $-AR^1$ wherein A is a substituted or unsubstituted alkylene group containing 1 to 6 carbon atoms and $R^1$ is selected from an a quaternary group.

4. The shampoo composition of claim 3 wherein A is substituted with at least one group selected from $C_1$ to $C_3$ alkyl, $C_1$ to $C_3$ haloalkyl, $C_1$ to $C_3$ hydroxyalkyl, hydroxyl, halogen.

5. The shampoo composition of claim 3 wherein said quaternary group is selected from quaternary ammonium compounds, quaternary sulfonium compounds, and quaternary phosphonium compounds.

6. The shampoo composition of claim 5 wherein said quaternary group is represented by the formulae:

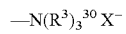

wherein $R^3$ independently represents substituted and unsubstituted $C_1$ to $C_{24}$ alkyl, substituted and unsubstituted benzyl and substituted and unsubstituted phenyl; and X represents any suitable anion that balances the charge on the onium cation.

7. The shampoo composition of claim 6 wherein said anion is selected from bromine, chlorine, fluorine and iodine.

8. The shampoo composition of claim 6 wherein said alkyl, benzyl and phenyl substituents are mono-substituted or multi-substituted with a substituent selected from $C_1$ to $C_3$ alkyl, hydroxyl, halogen, and combinations thereof.

9. The shampoo composition of claim 1 wherein said water soluble silicone has a polysiloxane containing backbone segment represented by the formula:

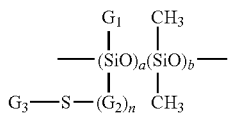

wherein $G_1$ represents hydrogen, $C_1$—$C_{10}$ alkyl and phenyl; $G_2$ represents $C_1$—$C_{10}$ alkylene; $G_3$ represents an anionic group containing polymeric residue obtained from the polymerization of at least one anionic monomer containing ethylenic unsaturation; n is 0 or 1; a is an integer ranging from 1 to 50; and b is an integer from 10 to 350.

10. The shampoo composition of claim 9 wherein said anionic group polymeric residue contains repeat units polymerized from ethylenic unsaturated monomers selected from acrylic acid, methacrylic acid and combinations thereof.

11. The shampoo composition of claim 10 wherein said ethylenic unsaturated monomers further comprise at least one $C_1$ to $C_{20}$ alkyl ester of acrylic and methacrylic acid.

12. The shampoo composition of claim 1 further comprising:
  e) a nonionic surfactant.

13. The shampoo composition of claim 1 further comprising:
  f) an insoluble silicone selected from silicone fluid(s), silicone resin(s), silicone gum(s), and mixtures thereof.

14. The shampoo composition of claim 1 further comprising:
  g) a suspending aid selected from ethylene glycol esters of $C_{12}$ to $C_{22}$ fatty acids, alkanol amides of $C_{12}$ to $C_{22}$ fatty acids, long chain esters of $C_{12}$ to $C_{22}$ fatty acids, long chain esters of long chain alkanol amides, N,N-dihydrocarbyl amido benzoic acid and salts thereof, xanthan gum, carboxyvinyl polymer(s), cellulose ether(s), polyvinyl alcohol, polyvinyl pyrrolidone, palmitamine, stearamine, dipalmitoylamine, di(hydrogenated tallow) amine, di(hydrogenated tallow) phthlaic acid amide, crosslinked maleic anhydride-methyl vinyl ether copolymer, cellulose ethers, and mixtures thereof.

15. The shampoo composition of claim 14 wherein said carboxyvinyl suspending aid contains repeating units polymerized from acrylic acid, methacrylic acid, and mixtures thereof in optional combination with $C_1$ to $C_{10}$ alkyl esters of acrylic acid, $C_1$ to $C_{10}$ alkyl esters of methacrylic acid, and mixtures thereof.

16. The shampoo composition of claim 15 wherein said carboxyvinyl suspending aid is crosslinked.

17. The shampoo composition of claim 1 further comprising:
  h) a fatty acid polyester obtained from the reaction of a polyol with a $C_8$ to $C_{22}$ saturated and/or unsaturated fatty acid, and mixtures thereof.

18. The shampoo composition of claim 1 further comprising:
  i) an optional component selected from anti-static agents, anti-dandruff agents, dyes, coloring agents, organic solvents or diluents, pearlescent agents, foam boosters, pediculocides, pH adjusting agents, perfumes, fragrances, preservatives, antimicrobials, proteins, skin active agents, styling polymers, sunscreens, vitamins, glycerine, polypropylene glycol, chelating agents, antioxidants, sunscreens, amino acids, ceramides, free fatty acids, and mixtures thereof.

19. The shampoo composition of claim 1 wherein said at least one polygalactomannan is obtained from cassia obtusifolia, cassia tora, and combinations thereof.

20. The shampoo composition of claim 1 wherein said polygalactomannan is co-minced with polysaccharide selected from seaweed raw materials, seaweed extract(s), microbiological polysaccharides, cellulose ethers and derivatives thereof, and combinations thereof.

21. The shampoo composition of claim 20 wherein said seaweed extract is selected from carrageenan and alginate.

22. The shampoo composition of claim 1 wherein said polygalactomannan is obtained by a method comprising the steps of:
  (a) swelling said cassia polygalactomannan with a split selected from tamarind, fenugreek, locust bean, tara or guar with water in the presence of a cationic derivatizing agent capable of reacting with the hydroxyl group in the galactose and mannose units in the galactomannan backbone of the split to form a swollen split, optionally followed by dispersing the swollen split in a water/organic solvent mixture, and
  (b) at least one step of wet-mincing the product obtained under (a).

23. The shampoo composition of claim 22 wherein said polygalactomannan is obtained by a method further comprising the steps of:
  (c) adding the minced and swollen split of step (b) to a water/organic solvent mixture; and
  (d) separating the water/organic solvent mixture from said polygalactomannan.

24. The shampoo composition according to claim 22 wherein in step (a) the split of cassia in combination with locust bean, tara or guar is swollen in the presence of a polysaccharide selected from seaweed raw materials, seaweed extracts and xanthan, cellulose and its derivatives, and combinations thereof.

25. The shampoo composition according to claim 1 wherein in step (a) said cassia polygalactomannan is swollen in the presence of a polysaccharide selected from seaweed raw materials, seaweed extracts and xanthan, cellulose and its derivatives, and combinations thereof.

* * * * *